US012649000B2

(12) United States Patent
Tagalakis et al.

(10) Patent No.: US 12,649,000 B2
(45) Date of Patent: Jun. 9, 2026

(54) USE OF ALGINATE OLIGOMERS TO ENHANCE THE TRANSLOCATION OF MICRO/NANOPARTICLES ACROSS MUCUS LAYERS

(71) Applicant: AlgiPharma AS, Sandvika (NO)

(72) Inventors: Aristides Tagalakis, Liverpool (GB); Stephen Hart, London (GB); Are Kristiansen, Vøyenenga (NO); Arne Dessen, Røyken (NO); Philip D. Rye, Eiksmarka (NO)

(73) Assignee: AlgiPharma AS, Sandvika (NO)

( * ) Notice: Subject to any disclaimer, the term of this patent is extended or adjusted under 35 U.S.C. 154(b) by 1050 days.

(21) Appl. No.: 16/982,240

(22) PCT Filed: Mar. 19, 2019

(86) PCT No.: PCT/EP2019/056890

§ 371 (c)(1),
(2) Date: Sep. 18, 2020

(87) PCT Pub. No.: WO2019/180047

PCT Pub. Date: Sep. 29, 2019

(65) Prior Publication Data

US 2021/0030891 A1 Feb. 4, 2021

(30) Foreign Application Priority Data

Mar. 19, 2018 (GR) .............................. 20180100114
Apr. 20, 2018 (GB) ...................................... 1806495

(51) Int. Cl.

| | |
|---|---|
| ***A61K 47/69*** | (2017.01) |
| ***A61K 47/61*** | (2017.01) |
| ***C12N 15/113*** | (2010.01) |
| *A61K 45/06* | (2006.01) |
| *B82Y 5/00* | (2011.01) |

(52) U.S. Cl.

CPC .......... *A61K 47/6929* (2017.08); *A61K 47/61* (2017.08); *C12N 15/1131* (2013.01); *A61K 45/06* (2013.01); *B82Y 5/00* (2013.01); *C12N 2750/14123* (2013.01); *C12N 2750/14143* (2013.01)

(58) Field of Classification Search

CPC .. A61K 47/61; A61K 47/6911; A61K 9/5161; A61K 9/1652

See application file for complete search history.

(56) References Cited

U.S. PATENT DOCUMENTS

| | | | | |
|---|---|---|---|---|
| 5,900,238 | A | 5/1999 | Gombotz et al. | |
| 9,629,813 | B2 | 4/2017 | Ensign et al. | |
| 2004/0013626 | A1* | 1/2004 | Gref | C08B 37/00 424/70.13 |
| 2015/0126467 | A1* | 5/2015 | Onsoyen | A61K 31/506 514/383 |
| 2015/0224202 | A1* | 8/2015 | Stevenson | A61K 9/146 514/185 |
| 2018/0235879 | A1* | 8/2018 | Nyambura | A61K 9/1623 |

FOREIGN PATENT DOCUMENTS

| | | | |
|---|---|---|---|
| EP | 1786441 | A2 | 5/2007 |
| EP | 3006045 | A1 | 4/2016 |
| GB | 2555391 | A | 5/2018 |
| WO | WO 96/15811 | A1 | 5/1996 |
| WO | WO 98/54347 | A1 | 12/1998 |
| WO | WO 00/50050 | A1 | 8/2000 |
| WO | WO 01/92543 | A2 | 12/2001 |
| WO | WO 02/072616 | A2 | 9/2002 |
| WO | WO 03/094974 | A1 | 11/2003 |
| WO | WO 2004/108938 | A2 | 12/2004 |
| WO | WO 2005/117985 | A2 | 12/2005 |
| WO | WO 2006/016115 | A2 | 2/2006 |

(Continued)

OTHER PUBLICATIONS

Lannuccelli et al., Drug Delivery, 2011, 18(1), 26-37 (Year: 2011).*

Brezaniova et al., "Self-assembled chitosan-alginate polyplex nanoparticles containing temporfin," Colloid Polym Sci; 295; 2017; 1259-1270.

D., et al, 2016, "Liposome production by microfluidics: potential and limiting factors," Scientific Reports, 6:25876.

Erdoğan S, et al., 2006, "Thrombus localization by using streptokinase containing vesicular systems," Drug Delivery, vol. 13(4):303-309.

Ermund, A, et al., OligoG CF-5/20 normalizes cystic fibrosis mucus by chelating calcium, Clin Exp Pharmacol Physiol. 2017;44:639-647.

(Continued)

*Primary Examiner* — Kyle A Purdy

(74) *Attorney, Agent, or Firm* — Knobbe, Martens, Olson & Bear, LLP

(57) ABSTRACT

A method for translocating a cationic micro/nanoparticle across a mucus layer, the method including (a) contacting the mucus layer with at least one alginate oligomer, the alginate oligomer having at least 70% mannuronate residues, together with the cationic micro/nanoparticle; or (b)(i) contacting the cationic micro/nanoparticle with an alginate oligomer having at least 70% mannuronate residues thereby forming a micro/nanoparticle carrying the alginate oligomer, and (b)(ii) contacting the mucus layer with the micro/nanoparticle prepared in step (b)(i). There is also provided a method for translocating a molecule of interest across a mucus layer including contacting the mucus layer with a micro/nanoparticle which is formed of self-assembling micro/nanoparticle forming components, wherein at least one is a cationic micro/nanoparticle forming agent and at least one is an alginate oligomer which has at least 70% mannuronate residues, and further comprises the molecule of interest, optionally wherein the molecule of interest is covalently bound to one or more of the self-assembling micro/nanoparticle forming components.

23 Claims, 7 Drawing Sheets

(56) References Cited

FOREIGN PATENT DOCUMENTS

| | | | |
|---|---|---|---|
| WO | WO 2007/039754 | A1 | 4/2007 |
| WO | WO 2007/138324 | A2 | 12/2007 |
| WO | WO 2008/125828 | A2 | 10/2008 |
| WO | WO 2010/109176 | A2 | 9/2010 |
| WO | WO 2010/109180 | A2 | 9/2010 |
| WO | WO 2010/139956 | A1 | 12/2010 |
| WO | WO 2015/128495 | A1 | 9/2015 |
| WO | WO 2016/030524 | A1 | 3/2016 |
| WO | WO 2017/153779 | A1 | 9/2017 |
| WO | WO 2017/220611 | A1 | 12/2017 |
| WO | WO 2018/073448 | A1 | 4/2018 |

OTHER PUBLICATIONS

Guan, S., et al., "Nanotechnologies in delivery of mRNA therapeutics using nonviral vector-based delivery systems;" Gene Therapy (2017) 24, 133-143.

Hart, S., "Multifunctional nanocomplexes for gene transfer and gene therapy;" Cell Biol Toxicol. 2010, 26(1):69-81.

Huang Z, et al., 2014, "Progress involving new techniques for liposome preparation," Asian Journal of Pharmaceutical Sciences, vol. 9(4):176-82.

Jurj, A., et al., "The new era of nanotechnology, an alternative to change cancer treatment," Drug Design, Development and Therapy 2017:11 2871-2890.

Kohane, D.S., "Microparticles and Nanoparticles for Drug Delivery," Biotechnology and Bioengineering, vol. 96, No. 2, 2007. 203-209.

Manunta, Maria D.I., et al. "Airway Deposition of Nebulized Gene Delivery Nanocomplexes Monitored by Radioimaging Agents," Am J Respir Cell Mol Biol, 2013, vol. 49(3), 471-480.

Manunta, Maria D.I., et al., "Delivery of ENAC siRNA to epithelial cells mediated by a targeted nanocomplex: a therapeutic strategy for cystic fibrosis," Scientific Reports | 7: 700 (2017).

Manunta, Maria D.I., et al., "Nebulisation of Receptor-Targeted Nanocomplexes for Gene Delivery to the Airway Epithelium," PLoS ONE, 2011 | vol. 6 | Issue 10 | e26768.

Meng F, et al., 2011, "Polymersomes spanning from nano- to microscales: Advanced vehicles for controlled drug delivery and robust vesicles for virus and cell mimicking," Journal of Physical Chemistry Letters, vol. 2(13):1533-1539.

Nordgard, Catherine Taylor et al., "Alterations in Mucus Barrier Function and Matrix Structure Induced by Guluronate Oligomers," Biomacromolecules 2014, 15, 2294-2300.

Nordgård and Draget, "Oligosaccharides as modulators of rheology in complex mucus systems," Biomacromolecules. 2011 12(8):3084-3090.

Sletmoen, Marit, et al., "Oligoguluronate induced competitive displacement of mucin-alginate interactions: relevance for mucolytic function," Soft Matter, 2012, 8, 8413-8421.

Suk, Jung Soo, et al., "Lung Gene Therapy with Highly Compacted DNA Nanoparticles that Overcome the Mucus Barrier," J Control Release. Mar. 2, 20148; 178: 8-17.

Tagalakis, Aristides, D., et al., "A method for concentrating lipid peptide DNA and siRNA nanocomplexes that retains their structure and transfection efficiency," International Journal of Nanomedicine 2015:10 2673-2683.

Tagalakis, Aristides, D., et al., "A Receptor-targeted Nanocomplex Vector System Optimized for Respiratory Gene Transfer," Molecular Therapy vol. 16 No. 5, 907-915, 2008.

Torchilin, Vladimir P., "Multifunctional nanocarriers," Advanced Drug Delivery Reviews, vol. 64(Suppl.) (2012) 302-315.

Vemuri S., et al., "Preparation and characterization of liposomes as therapeutic delivery systems: a review," (1995) Pharmaceutica Acta Helvetiae, vol. 70(2):95-111.

Vert, Michel, et al., "Terminology for biorelated polymers and applications (IUPAC Recommendations 2012)", Pure Appl. Chem., vol. 84, No. 2, pp. 377-410 (2012).

Yildiz, Hasan M., "Size Selectivity of Intestinal Mucus to Diffusing Particulates is Dependent on Surface Chemistry and Exposure to Lipids," J Drug Target (2015); 23(7-8): 768-774.

International Search Report and Written Opinion, PCT/EP2019/056890, mailed Aug. 20, 2019.

Tagalakis, A., et al., "Alginate enhanced diffusion of cationic nanoparticles through mucosal barrier," Pediatric Pulmonolgy, vol. 53, No. Supplement 2, 242, Sep. 1, 2018, pp. 238-239.

Gombotz, W.R., et al., "Protein Release from Alginate Matrices," Advanced Drug Delivery Reviews, vol. 31, May 4, 1998, pp. 267-285.

Mukhopadhyay, P. et al., "pH-sensitive chitosan/alginate core-shell nanoparticles for efficient and safe oral insulin delivery," International Journal of Biological Macromolecules, vol. 72, 2015, pp. 640-648.

* cited by examiner

| Structure | Activity | Name |
|---|---|---|
|  | potentiator | VRT-532 |
|  | potentiator | PG-01 |
|  | potentiator | SF-03 |
|  | potentiator | UCCF-853 |
|  | potentiator | ΔF508act-02 |
|  | potentiator | Genistein |
|  | potentiator | NS004 |

VRT-422 potentiator

| | | |
|---|---|---|
|  | potentiator | UCCF-029 |
|  | potentiator | UCCF-180 |
|  | potentiator | UCCF-152 |
|  | potentiator | corr-3a |
|  | potentiator | VRT-640 |
|  | potentiator | VRT-325 |
|  | potentiator | corr-4a |
|  | potentiator | felodipine |
|  | potentiator | DHP-229 |
|  | potentiator | DHP-256 |

USE OF ALGINATE OLIGOMERS TO ENHANCE THE TRANSLOCATION OF MICRO/NANOPARTICLES ACROSS MUCUS LAYERS

The present invention relates to the use of alginate oligomers to enhance the translocation of micro/nanoparticles across mucus layers, in particular to enhance the delivery of therapeutically or diagnostically useful molecules when provided in micro/nanoparticulate form or when carried by a micro/nanoparticle to the epithelial cell layers of mucous membranes, thereby enhancing localised delivery and/or systemic uptake of the molecule. In ex vivo and in vitro contexts the delivery of micro/nanoparticles to cultured cells which generate a mucus layer or to tissues carrying a mucous membrane may be enhanced. More specifically, the invention provides a certain class of alginate oligomers, namely mannuronate rich alginate oligomers, to enhance the translocation of cationic micro/nanoparticles or self-assembling micro/nanoparticles formed from cationic components across mucus layers, in particular mucus layers of abnormal viscosity, e.g. the mucus of subjects with cystic fibrous transmembrane receptor dysfunction. The invention has particular utility in the delivery of nucleic acids, e.g. therapeutic nucleic acids, or active agents of limited bioavailability to cells underlying mucus layers, especially in subjects with CFTR dysfunction.

The efficacy of modern precision medicines is often limited by their ability to reach their targets. The mucosal surfaces of the respiratory, intestinal and genitourinary tracts, due to their vascularity and large surface area, are attractive target sites for drug delivery. However, the mucus barrier of such surfaces, a charged and complex polymeric “mesh” of components, including mucins, bacterial and host-derived polysaccharides, bacteria and extracellular DNA, represents one of the major hurdles that dictate the bioavailability, adsorption, and subsequent efficacy of those medicines delivered by respiratory or oral administration or directly to mucosal surfaces. Moreover, in many chronic respiratory and gastrointestinal diseases, e.g. cystic fibrous the production of highly viscous mucus impedes its clearance and prolongs infection and inflammation. This abnormal mucus compounds the challenges of deliver therapies across these mucus barriers in such patients.

Many drugs, including antibiotics, are being developed for inhaled delivery, especially those commonly used in the treatment of cystic fibrosis (CF). Disease modifying therapeutics for CF are also being formulated for oral administration. However, their insolubility in water poses a significant issue for the bioavailability of these drugs.

One promising approach to improving the overall bioavailability of therapeutics or diagnostic agents that are challenging to deliver, e.g. due to poor water solubility, instability or non-specific toxicity, is to incorporate or form such drugs into microparticles or nanoparticles. Such particles include vesicles (e.g. liposomes, polymersomes and niosomes), polymeric particles, metal particles, micelles, viruses, virus like particles, dendrimers, carbon nanotubes and hybrid versions of these entities. Particulate delivery systems are also a common feature of therapies or diagnostic approaches based on nucleic acids as active agents, e.g. gene therapy, gene editing, RNA interference therapy, in vitro transcribed mRNA therapy, antisense therapy and the use of nucleic acids as molecular probes, because of issues associated with the effective delivery of such molecules to target cells.

However, most particle-based drug delivery systems are trapped by mucus layers and subsequently rapidly removed. The efficacy of particulate delivery systems is thereby strongly limited, and is a long-standing challenge in the field.

To date, researchers have employed numerous techniques in an attempt to improve trans-mucosal drug/particle delivery (e.g. mucoadhesive and mucus penetrating particles). None, however, are currently approved for use in chronic respiratory disease due to problems with non-specific binding, mucous clearance and toxicity. There is an urgent unmet need therefore to develop novel delivery strategies that can facilitate the trans-mucosal delivery of drugs and small molecules in the treatment and diagnosis of human disease.

Alginates are naturally occurring polysaccharides that have been found to have a number of uses, both clinical (e.g. in wound dressings, as drug carriers and in anti-heartburn preparations) and non-clinical (e.g. in food preparation). They are linear polymers of (1-4) linked R-D-mannuronic acid (M) and/or its C-5 epimer α-L-guluronic acid (G). The primary structure of alginates can vary greatly. The M and G residues can be organised as homopolymeric blocks of contiguous M or G residues, as blocks of alternating M and G residues and single M or G residues can be found interspacing these block structures. An alginate molecule can comprise some or all of these structures and such structures might not be uniformly distributed throughout the polymer. In the extreme, there exists a homopolymer of guluronic acid (polyguluronate) or a homopolymer of mannuronic acid (polymannuronate).

Alginates have been isolated from marine brown algae (e.g. certain species of *Durvillea, Lessonia* and *Laminaria*) and bacteria such as *Pseudomonas aeruginosa* and *Azotobacter vinelandii*. Other pseudomonads (e.g. *Pseudomonas fluorescens, Pseudomonas putida*, and *Pseudomonas mendocina*) retain the genetic capacity to produce alginates but in the wild they do not produce detectable levels of alginate. By mutation these non-producing pseudomonads can be induced to produce stably large quantities of alginate.

Alginate is synthesised as polymannuronate and G residues are formed by the action of epimerases (specifically C-5 epimerases) on the M residues in the polymer. In the case of alginates extracted from algae, the G residues are predominantly organised as G blocks because the enzymes involved in alginate biosynthesis in algae preferentially introduce the G neighbouring another G, thus converting stretches of M residues into G-blocks. Elucidation of these biosynthetic systems has allowed the production of alginates with specific primary structures (WO 94/09124, Gimmestad, M et al, Journal of Bacteriology, 2003, Vol 185(12) 3515-3523 and WO 2004/011628).

Alginates are typically isolated from natural sources as large high molecular weight polymers (e.g. an average molecular weight in the range 300,000 to 500,000 Daltons). It is known, however, that such large alginate polymers may be degraded, or broken down, e.g. by chemical or enzymatic hydrolysis to produce alginate structures of lower molecular weight. Alginates that are used industrially typically have an average molecular weight in the range of 100,000 to 300,000 Daltons (such alginates are still considered to be large polymers) although alginates of an average molecular weight of approximately 35,000 Daltons have been used as excipients in pharmaceuticals.

WO2007/039754, WO2008/125828 and WO2010/109180 describe certain effects of oligoguluronates (alginate oligomers with a high proportion of G residues) on the viscosity of mucus and the diffusion of polymeric biological/ macromolecular drugs and anionic nanoparticles through mucus. WO2010/109176 also describes certain effects oligoguluronates have on the transfection properties of nucleic acid carrying cationic liposome nanoparticles. WO2015/128495 describes the ability of certain alginate G residue containing alginate oligomers to normalise the properties of mucus in patients with CFTR dysfunction, e.g. cystic fibrous patients.

It has now been found surprisingly that alginate oligomers rich in mannuronate, but not alginate oligomers rich in guluronate, enhance the translocation of cationic micro/nanoparticles, but not anionic micro/nanoparticles, across mucus layers. Such alginate oligomers may also be incorporated into self-assembling micro/nanoparticles together with cationic micro/nanoparticle forming components and such micro/nanoparticles would be expected to translocate across mucus layers with enhanced efficiency as compared to equivalent micro/nanoparticles formed in the absence of such alginate oligomers. It has also been found that oligomers rich in mannuronate, but not alginate oligomers rich in guluronate, reduce cytotoxicity associated with cationic micro/nanoparticles and micro/nanoparticles comprising cationic micro/nanoparticle forming components.

Without wishing to be bound by theory it is believed that mannuronate rich alginate oligomers have these particular properties, but guluronate rich alginate oligomers do not, on account of their negative charge and their flexible structure.

The various components of mucus are such that the substance carries an overall negative charge. In airway mucus secretions MUC5AC and MUC5B are the predominant mucins in the viscoelastic gel. These mucins consist of long tandem repeats rich in proline, threonine, serine (PTS domains) that are glycosylated on most threonines and serines. Many of these glycans terminate in negatively charged carboxyl or sulphate groups, conferring high negative charge on PTS domains. This negative charge promotes electrostatic adhesive trapping of cationic particulates. In subjects with chronic airway inflammation, e.g. as seen in CF, mucin hypersecretion takes place. This causes the mucin content to increase, conferring higher negative charge and viscoelasticity on CF mucus. Increased mucin content also reduces CF mucus mesh pore sizes. Other biomacromolecules, including chromosomal DNA and F-actin microfilaments, predominate in the airway mucus secretions of subjects with chronic airway inflammation and such increased DNA levels also confer higher negative charge on CF mucus and reduced mucus mesh pore sizes. This increased negative charge and reduce mesh pore size results in even more pronounced adhesive trapping of cationic particulates, e.g. micro/nanoparticles, in such subjects.

Alginate oligomers are negatively charged molecules and when applied to the mucus and/or the cationic micro/nanoparticles or incorporated together with cationic micro/nanoparticle forming components are believed to result in a reduced positive charge or even a negative charge on the particle and this in turn reduces or negates the hindering effects arising from the overall negative charge of the mucus. However, it is believed that mannuronate rich alginate oligomers, but not guluronate rich alginate oligomers, are capable of enhancing translocation of cationic micro/nanoparticles because of the relative flexibility of each type of oligomer. Guluronate residues bind neighbouring guluronate residues diaxially and this results in hindered rotation about the glycosidic bond and a stiff and extended uronate chain. On the other hand, mannuronate residues bind neighbouring mannuronate residues diequatorially, which is a less hindered arrangement, and this gives rise to a much more flexible chain. It is believed that the flexibility of mannuronate rich alginate oligomers means that these molecules are less of a physical hindrance for the micro/nanoparticles as they pass through the mucin mesh pores of mucus, whereas the stiff and inflexible guluronate oligomers are more likely to caught in the complex network of mucus components.

These findings are of particular note because cationic micro/nanoparticles and micro/nanoparticles comprising cationic micro/nanoparticle forming components have certain advantages over anionic micro/nanoparticles, including superior cell transfection efficiencies and superior packaging efficiencies of anionic drugs (e.g. nucleic acids), but face significant delivery obstacles in certain applications and are recognised to have cytotoxic effects. The present invention therefore facilitates the use of certain types of highly advantageous micro/nanoparticles in the context of delivery sites below mucus layers by mitigating the barrier effect of the mucus and, in certain embodiments, reducing cytotoxic effects of such particles.

In a first aspect the invention therefore provides a method for translocating a cationic micro/nanoparticle across a mucus layer said method comprising (a) contacting the mucus layer with at least one alginate oligomer, said alginate oligomer having at least 70% mannuronate residues, together with the cationic micro/nanoparticle; or (b)(i) contacting the cationic micro/nanoparticle with an alginate oligomer having at least 70% mannuronate residues thereby forming a micro/nanoparticle carrying said alginate oligomer, and (b)(ii) contacting the mucus layer with the micro/nanoparticle prepared in step (b)(i).

The invention further provides a method for enhancing the translocation of a cationic micro/nanoparticle across a mucus layer said method comprising (a) contacting the mucus layer with at least one alginate oligomer, said alginate oligomer having at least 70% mannuronate residues, together with the cationic micro/nanoparticle; or (b)(i) contacting the cationic micro/nanoparticle with at least one alginate oligomer having at least 70% mannuronate residues thereby forming a micro/nanoparticle carrying said alginate oligomer, and (b)(ii) contacting the mucus layer with the micro/nanoparticle prepared in step (b)(i).

The invention may be considered to further provide a method for delivering a molecule of interest to an epithelial cell of a mucosal surface, said method comprising (a) contacting the mucus layer of the mucosal surface with at least one alginate oligomer, said alginate oligomer having at least 70% mannuronate residues, together with a cationic micro/nanoparticle comprising said molecule of interest; or (b)(i) contacting a cationic micro/nanoparticle comprising said molecule with at least one alginate oligomer, said alginate oligomer having at least 70% mannuronate residues thereby forming a micro/nanoparticle carrying said alginate oligomer, and (b)(ii) contacting the mucus layer of the mucosal surface with the micro/nanoparticle prepared in step (b)(i).

The invention further provides a method for enhancing the delivery of a molecule of interest to an epithelial cell of a mucosal surface by cationic micro/nanoparticle, said method comprising (a) contacting the mucus layer of the mucosal surface with at least one alginate oligomer, said alginate oligomer having at least 70% mannuronate residues, together with a cationic micro/nanoparticle comprising said molecule of interest; or (b)(i) contacting a cationic micro/nanoparticle comprising said molecule with at least one alginate oligomer, said alginate oligomer having at least 70% mannuronate residues thereby forming a micro/nanoparticle carrying said alginate oligomer, and (b)(ii) contacting the mucus layer of the mucosal surface with the micro/nanoparticle prepared in step (b)(i).

In these aspects the micro/nanoparticle may, for instance, carry the molecule of interest or said molecule may be provided in a micro/nanoparticulate form thereof. More specifically, the molecule of interest may be covalently bound to another component, e.g. a self-assembling component, of the micro/nanoparticle or may be distinct from other components of the micro/nanoparticle. The molecule of interest may be carried in or on any part of the micro/nanoparticle, e.g. on the surface, in an interior void or in or on one or more layers of the particle, or a combination thereof. Thus, the molecule may be present inside a lamellar phase (layer), traversing a lamellar phase and/or associated with (e.g. bound to) the external face of a lamellar phase or may be encapsulated by a lamellar phase, i.e. the molecule is found free in an internal phase of a hollow micro/nanoparticle and/or associated with (e.g. bound to) the internal face of a lamellar phase of the micro/nanoparticle, but is not found inside the lamellar phase, traversing the lamellar phase or associated with (e.g. bound to) the external face of the lamellar phase. In other words, in such embodiments, essentially no part of the molecule of interest is exposed to the external phase. Such arrangements might be particular utility in embodiments in which the molecule of interest may be toxic, may have deleterious effects in off-target locations, may induce a deleterious immune response, or is poorly water soluble.

The invention further provides a method for translocating a molecule of interest across a mucus layer said method comprising contacting the mucus layer with a micro/nanoparticle which is (i) formed of self-assembling micro/nanoparticle forming components, wherein at least one is a cationic micro/nanoparticle forming agent and at least one is an alginate oligomer which has at least 70% mannuronate residues, and (ii) further comprises said molecule of interest, optionally wherein the molecule of interest is covalently bound to one or more of the self-assembling micro/nanoparticle forming components.

The invention further provides a method for delivering a molecule of interest to an epithelial cell of a mucosal surface, said method comprising contacting the mucus layer of the mucosal surface with a micro/nanoparticle which is (i) formed of self-assembling micro/nanoparticle forming components, wherein at least one is a cationic micro/nanoparticle forming component and at least one is an alginate oligomer which has at least 70% mannuronate residues, and (ii) further comprises said molecule of interest, optionally wherein the molecule of interest is covalently bound to one or more of the self-assembling micro/nanoparticle forming components.

The invention further provides a micro/nanoparticle formed of self-assembling micro/nanoparticle forming components, wherein (i) at least one self-assembling micro/nanoparticle forming component is a cationic micro/nanoparticle forming component and at least one is an alginate oligomer which has at least 70% mannuronate residues, and (ii) said micro/nanoparticle further comprises a molecule of interest, optionally wherein the molecule of interest is covalently bound to one or more of the self-assembling micro/nanoparticle forming components.

A molecule of interest is a molecule for which a skilled user has a particular predetermined utility. For instance, it may be a molecule the skilled person wishes to be delivered to a target site in order to perform a function or to exert an effect, directly or indirectly, at the target site or elsewhere, or a molecule which may provide information, directly or indirectly, on a target site or processes occurring at that target site or elsewhere. Thus the identity of such molecules is essentially limited only by the objectives of the skilled person in the particular context in which the micro/nanoparticles of use in the invention are used. In certain specific embodiments the molecule may be a molecule of therapeutic and/or diagnostic utility, e.g. a pharmaceutical (drug) or diagnostic agent, and in these embodiments the micro/nanoparticle may be considered a therapeutic/diagnostic micro/nanoparticle as appropriate. The term molecule of interest may be taken to extend to an arrangement of molecules.

It will immediately be appreciated that a molecule of interest in accordance with the invention is not a mannuronate rich alginate oligomer of use in the invention as defined herein, e.g. an alginate which has at least 70% mannuronate residues or any other alginate oligomer defined herein. In other embodiments a molecule of interest in accordance with the invention is not a cationic micro/nanoparticle forming component of use in the invention as defined herein. In other embodiments the molecule of interest is not an essential structural component of the micro/nanoparticle in question, e.g. a self-assembling micro/nanoparticle forming component.

In these aspects the molecule of interest may be covalently bound to a self-assembling component of the micro/nanoparticle or may be distinct from (not associated with or bound to, or at least only transiently associated with or bound to) a self-assembling component of the micro/nanoparticle. The molecule of interest may be carried in or on any part of the micro/nanoparticle, e.g. on the surface, in an interior void or in one or more layers of the particle, or a combination thereof. The above discussion in this regard applies mutatis mutandis to this section.

Self-assembling micro/nanoparticle forming components are compounds which alone and/or together with other self-assembling micro/nanoparticle forming compounds may arrange, e.g. spontaneously, into micro/nanoparticles under suitable physical and/or chemical conditions. In certain embodiments self-assembling micro/nanoparticle forming components of use in the invention may be amphiphilic compounds which are capable of arranging into micro/nanovesicles and/or micro/nanomicelles, e.g. those amphiphilic self-assembling micro/nanoparticle forming compounds described in more detail below. In other embodiments self-assembling micro/nanoparticle forming components of use in the invention may be the structural components of viruses or virus-like particles, e.g. those discussed in greater detail below. In certain embodiments the cationic micro/nanoparticle forming component and the alginate oligomer are covalently linked.

The above-mentioned micro/nanoparticle, in particular those comprising a molecule of interest which is a therapeutic or diagnostic molecule, may be provided for use in therapy.

The invention further provides an alginate oligomer, wherein said alginate oligomer has at least 70% mannuronate residues, for use in a method for translocating a therapeutic or diagnostic cationic micro/nanoparticle across a mucus layer of a subject said method comprising (a) contacting the mucus layer with at least one alginate oligomer, said alginate oligomer having at least 70% mannuronate residues, together with the cationic micro/nanoparticle; or (b)(i) contacting the cationic micro/nanoparticle with an alginate oligomer having at least 70% mannuronate residues thereby forming a micro/nanoparticle carrying said alginate oligomer, and (b)(ii) contacting the mucus layer with the micro/nanoparticle prepared in step (b)(i).

The invention further provides an alginate oligomer, wherein said alginate oligomer has at least 70% mannuronate residues, for use in a method for delivering a therapeutic or diagnostic molecule of interest to an epithelial cell of a mucosal surface of a subject, said method comprising (a) contacting the mucus layer of the mucosal surface with at least one alginate oligomer, said alginate oligomer having at least 70% mannuronate residues, together with a cationic micro/nanoparticle comprising said therapeutic or diagnostic molecule of interest; or (b)(i) contacting a cationic micro/nanoparticle comprising said therapeutic or diagnostic molecule of interest with at least one alginate oligomer, said alginate oligomer having at least 70% mannuronate residues thereby forming a micro/nanoparticle carrying said alginate oligomer, and (b)(ii) contacting the mucus layer of the mucosal surface with the micro/nanoparticle prepared in step (b)(i).

The invention also provides an alginate oligomer, wherein said alginate oligomer has at least 70% mannuronate residues, for use in a method for translocating a therapeutic or diagnostic molecule of interest across a mucus layer of a subject, said method comprising (a) preparing a micro/nanoparticle formed of self-assembling micro/nanoparticle forming components, wherein at least one self-assembling micro/nanoparticle forming component is a cationic micro/nanoparticle forming component and at least one is said alginate oligomer, said micro/nanoparticle further comprising the therapeutic or diagnostic molecule of interest, optionally wherein the therapeutic or diagnostic molecule is covalently bound to one or more of the self-assembling micro/nanoparticle forming components and (b) contacting the mucus layer with the micro/nanoparticle prepared in step (a).

The invention also provides an alginate oligomer, wherein said alginate oligomer has at least 70% mannuronate residues, for use in a method for delivering a therapeutic or diagnostic molecule of interest to an epithelial cell of a mucosal surface of a subject, said method comprising (a) preparing a micro/nanoparticle formed of self-assembling micro/nanoparticle forming components, wherein at least one self-assembling micro/nanoparticle forming component is a cationic micro/nanoparticle forming component and at least one is said alginate oligomer, said micro/nanoparticle further comprising said the therapeutic or diagnostic molecule of interest, optionally wherein the therapeutic or diagnostic molecule is covalently bound to one or more of the self-assembling micro/nanoparticle forming components and (b) contacting the mucus layer of the mucosal surface with the micro/nanoparticle prepared in step (a).

In these aspects said translocation or said delivery may be considered to be enhanced.

In certain embodiments the methods and uses of the invention involving a micro/nanoparticle formed of self-assembling micro/nanoparticle forming compounds may comprise a further step in which the micro/nanoparticle is prepared, e.g. as described in more detail below.

The invention still further provides the use of an alginate oligomer, wherein said alginate oligomer has at least 70% mannuronate residues, in the manufacture of a medicament for use in the above described methods. In certain embodiments, the medicament may be a micro/nanoparticle carrying an alginate oligomer or a micro/nanoparticle formed of self-assembling micro/nanoparticle forming compounds described herein.

The invention still further provides the use of a therapeutic or diagnostic cationic micro/nanoparticle, e.g as defined herein, in the manufacture of a medicament for use in the above described methods. In certain embodiments, the medicament may be a micro/nanoparticle carrying an alginate oligomer or a micro/nanoparticle formed of self-assembling micro/nanoparticle forming compounds described herein.

In certain embodiments in which the alginate oligomer is contacted with a mucus layer together with a therapeutic or diagnostic cationic micro/nanoparticle, or embodiments in which the alginate oligomer is contacted with the therapeutic or diagnostic micro/nanoparticle prior to contacting the micro/nanoparticle so formed with a mucus layer, the medicament may further comprise the therapeutic or diagnostic cationic micro/nanoparticle.

The medicament may be in the form of a single composition or formulation comprising the alginate oligomer and cationic micro/nanoparticle or separate compositions or formulations may be prepared and used, each containing the alginate oligomer or the cationic micro/nanoparticle respectively.

Thus, the present invention provides the use of an alginate oligomer having at least 70% mannuronate residues and a therapeutic or diagnostic cationic micro/nanoparticle in the manufacture of a medicament for use in embodiments of the above described methods in which a mucus layer is contacted with at least one alginate oligomer having at least 70% mannuronate residues together with a therapeutic or diagnostic cationic micro/nanoparticle, or embodiments in which at least one alginate oligomer having at least 70% mannuronate residues is contacted with a therapeutic or diagnostic micro/nanoparticle prior to contacting the micro/nanoparticle so formed with a mucus layer.

As noted above, the micro/nanoparticle may be applied or administered separately from the alginate oligomer. Consistent with this, a still further aspect of the present invention provides a product containing an alginate oligomer having at least 70% mannuronate residues and a cationic micro/nanoparticle (e.g. as defined herein) as a combined preparation, especially for separate, simultaneous or sequential use in the methods defined herein, in particular embodiments of the above described methods in which a mucus layer is contacted with at least one alginate oligomer having at least 70% mannuronate residues together with a therapeutic or diagnostic cationic micro/nanoparticle, or embodiments in which at least one alginate oligomer having at least 70% mannuronate residues is contacted with a therapeutic or diagnostic micro/nanoparticle prior to contacting the micro/nanoparticle so formed with a mucus layer. The product may be viewed as a pharmaceutical product or combination product, or as a kit, comprising the alginate oligomer and the cationic micro/nanoparticle.

The term "contacting the mucus layer" encompasses any means of delivering an entity (e.g. alginate oligomer and/or micro/nanoparticle) to a mucus layer, whether directly or indirectly, and thus any means of applying or administering the entity to the mucus layer, or exposing the mucus layer to the entity, e.g. applying the entity directly to the mucus layer is encompassed. In particular, the step of contacting the mucus layer with the entity (administering the entity to the mucus layer) may include administering the entity to a subject, and in particular to a subject in need of such treatment with a therapeutic and/or diagnostic micro/nanoparticle. It will be appreciated therefore that both medical and non-medical methods are included, e.g. in vitro and ex vivo methods are included as well as in vivo methods. Thus, expressly included within the scope of the invention are methods which are not carried out in or on the human or non-human animal body, or in relation to, a mucus layer in or on the human or non-human animal body, but in other embodiments the subject may be any human or non-human animal subject, e.g. any mammalian subject, but will typically be a human subject, or patient. In these contexts the contacting step will be achieved by administering the entity to the subject, e.g. in the compositions described below.

By "contacting together" it is meant that the cationic micro/nanoparticle and the alginate oligomer are used in combination to achieve (enhanced) translocation/delivery of the cationic micro/nanoparticle. It is particularly meant that an effective amount of the alginate oligomer is administered at the same or substantially the same time as or prior to administering an effective amount of the cationic micro/nanoparticle. In other embodiments an effective amount of the oligomer is administered separately to and after the cationic micro/nanoparticle. The skilled man would readily be able to design a dosage regimen to maximise the effect of the alginate oligomer on the translocation/delivery of the cationic micro/nanoparticle. He would also be able to select optimal combinations of the two active agents depending on the particular situation he is working with. An effective amount may be an amount sufficient to impart a negative surface charge to the cationic micro/nanoparticle, e.g. a surface charge of an anionic micro/nanoparticle as defined herein, e.g. as may be measured in vitro in water with a dynamic light scattering method or instrument (e.g. Malvern Nano ZS Zetasizer)

"Use together" does not imply that the respective agents are present in the same formulation or composition, and accordingly even if used, or administered, at the same or substantially the same time, the alginate oligomer and micro/nanoparticle need not be present in the same composition or formulation, but may be administered separately. Thus "separate" use/administration includes use/administration at the same or substantially the same time, or at different times, e.g. sequentially, or at different time intervals according to the desired dosage or usage regime. "Simultaneous" administration accordingly includes administration of the alginate oligomer and micro/nanoparticle within the same composition or formulation, or within separate compositions/formulations administered at the same or substantially the same time. In certain embodiments the alginate oligomer may be carried by the cationic micro/nanoparticle, e.g. as a coating or external layer or shell.

The cationic micro/nanoparticle may thus be applied or administered simultaneously with the alginate oligomer or sequentially. As noted above, in one embodiment the cationic micro/nanoparticle is administered at the same or substantially the same time as the alginate oligomer, and in another embodiment it is administered after the alginate oligomer or before the alginate oligomer. Thus, in other embodiments the oligomer is administered separately to, either before or after the cationic micro/nanoparticle. Included within the scope of "substantially the same time" is application or administration of the cationic micro/nanoparticle immediately or almost immediately before or after the alginate oligomer. The term "almost immediately" may be read as including application or administration within one hour of the previous application or administration, preferably within 30 minutes. However the cationic micro/nanoparticle may be applied or administered at least 1 hour, at least 3 hours, or at least 6 hours or more after the alginate oligomer. In these embodiments the cationic micro/nanoparticle can be applied or administered with or without a further application of an alginate oligomer. The alginate oligomer can be applied or administered in a plurality of applications prior to or with the cationic micro/nanoparticle, including as noted above, an application or administration immediately or almost immediately before the cationic micro/nanoparticle. In other embodiments the cationic micro/nanoparticle may conveniently be applied or administered before the alginate oligomer, e.g. at least 1 hour, at least 3 hours, at least 6 hours before the alginate oligomer. In these embodiments the alginate oligomer can be applied or administered with or without a further application of the cationic micro/nanoparticle. The cationic micro/nanoparticle can be applied or administered in a plurality of applications prior to or with the alginate oligomer.

Steps within the methods of the invention which comprise contacting a micro/nanoparticle with an alginate oligomer encompasses any means of delivering the alginate oligomer to a micro/nanoparticle, whether directly or indirectly, and thus any means of applying the alginate oligomer to the micro/nanoparticle, or exposing the micro/nanoparticle to the alginate oligomer, e.g. applying the alginate oligomer directly to the micro/nanoparticle is encompassed. In particular, the step of contacting the micro/nanoparticle with the alginate oligomer may include administering both entities to a subject, and in particular to a subject in need of such treatment with a therapeutic and/or diagnostic micro/nanoparticle, in such a way as to effect contact. In other embodiments, contact is performed in vitro, e.g. prior to the administration of the treated micro/nanoparticle to a subject or directly to a mucus layer. The contacting step results in the micro/nanoparticle carrying the alginate oligomer. The exact nature of this physical relationship is not limited and may be any form of non-covalent or covalent physical interaction, typically non-covalent (e.g. ionic, hydrogen and/or electrostatic bonding), that causes the alginate oligomer to persist on or at the surface of the micro/nanoparticle. This may be in amounts which may be considered as a coating or external layer or shell, or may be a sparser distribution. In certain embodiments the alginate oligomer will bind to the micro/nanoparticle ionically and/or electrostatically, i.e. via an ionic and/or electrostatic interaction, or a hydrogen bond.

In these embodiments, the micro/nanoparticle is contacted with an amount of alginate oligomer sufficient to form a micro/nanoparticle carrying an amount of alginate oligomer effective to achieve (enhanced) translocation/delivery. An effective amount may be an amount sufficient to impart a negative surface charge to the micro/nanoparticle, e.g. a surface charge of an anionic micro/nanoparticle as defined herein.

A mucosal surface is defined herein as any surface of an animal body, both internal or external, that secretes, has, carries or is to any extent coated with mucus (i.e. a mucus layer). More specifically a mucosal surface is a tissue lining comprising epithelial cells, typically arranged as an epithelial cell layer (an epithelium), that secretes, has, carries or is to any extent coated with mucus. It will be recognised that the terms "mucous membrane" and "mucosa" may alternatively be used to refer to a mucosal surface. This definition is considered to extend to artificially cultured versions of said surfaces or models of said surfaces. Thus included are the mucus coated surfaces of tissues or organs undergoing tissue/organ culture or cultures of cells which generate a mucus layer/coating.

In certain embodiments the methods of the invention may be applied to a mucosal surface affected by CFTR dysfunction and so will secrete, have, carry or be to any extent coated with the abnormal mucus characteristic of CF (mucus that is dense, intractable and in some instances at least partially attached to the underlying epithelium). It is believed that such mucus poses particular problems for micro/nanoparticle translocation and the invention is particularly suited to addressing such problems.

The mucosal surface may be in the respiratory system, e.g. the upper respiratory tract (nose, nasal passages, pharynx larynx and trachea), the paranasal sinuses and the bronchi (primary, secondary and tertiary) and bronchioles of the lower respiratory tract. Preferably the mucosal surface will be in the respiratory tract, preferably the trachea, bronchi and bronchioles.

The mucosal surface may be in the gastrointestinal tract, e.g. the mouth, the pharynx, the oesophagus, the duodenum and the small intestine (the jejunum and the ileum). The upper GI tract consists of the mouth, pharynx, oesophagus, stomach, and duodenum, and the lower GI tract, consists of the small intestine, the large intestine (the cecum, the colon and the rectum) and the anus.

The mucosal surface may be in the pancreatic and/or bile ducts.

The mucosal surface may be in the female reproductive system, e.g. the vagina, the cervix, the uterus, the fallopian tubes and the ovaries, preferably the cervix, uterus and the fallopian tubes.

The mucosal surface may be in the male reproductive system, e.g. the testes, the epididymis, the vas deferens, the accessory glands, the seminal vesicles, the prostate gland and the bulbourethral gland.

In accordance with the present invention, translocation across a mucus layer refers to the act of a micro/nanoparticle moving from one face of a mucus layer to the other across the depth of the layer, more specifically from the apical face (also referred to as the mucosal surface or the mucus/lumen interface) to the basal face (also referred to mucus/epithelial cell interface). In will be appreciated that, in practice, translocation is driven by diffusion along concentration gradients and as such may be viewed as the diffusion of a micro/nanoparticle, or population thereof, through a mucus layer.

Translocation across a mucus layer (diffusion through a mucus layer) may be expressed in terms of the absolute amount of micro/nanoparticles which move from one face of the mucus layer to the other, usually in a set period of time (e.g. as the cumulative concentration at the basal face of the layer) or in terms of the proportion of a population of micro/nanoparticles which move from one face of the mucus layer to the other, usually over a set time (translocation efficiency or percentage translocation). A rate of translocation may be calculated therefrom.

"Delivering a molecule of interest to an epithelial cell of a mucosal surface" refers to the act of bringing the molecule of interest into close proximity to epithelial cell underlying a mucus layer, specifically the apical surface of the epithelial cell. In certain embodiments this may involve achieving contact between an epithelial cell underlying a mucus layer, specifically the apical surface of the epithelial cell, and the molecule of interest. In certain embodiments said contact involves interaction between the molecule of interest and receptors, e.g. specific receptors, for said molecule present on the surface (apical surface) of the epithelial cell. In certain embodiments said delivery may involve uptake of the molecule of interest or the micro/nanoparticle comprising said molecule by the epithelial cell, e.g. by endocytosis (pinocytosis, receptor mediated endocytosis, phagocytosis and caveolar endocytosis) or membrane fusion.

Enhanced translocation encompasses any positive effect on this process. This may be seen as an increase in the total amount of micro/nanoparticle translocated or an increase in the proportion of a population of micro/nanoparticles translocated (translocation efficiency). It may be seen as an increase in the rate (velocity) at which a micro/nanoparticle is translocated. It may be seen as a reduction in the resistance to translocation caused by the mucus (e.g. impedance) or an increase in permeability of the mucus to the micro/nanoparticle (e.g. diffusion coefficient expressed as diffusion in mucus over diffusion in water). It may be seen in a reduction translocation/diffusion back to the apical face of the mucus layer. The Examples describe a number of techniques to assess these characteristics.

Enhanced delivery of a molecule of interest encompasses any positive effect on this process. This may be seen as an increase in the total amount of molecule delivered or an increase in the proportion of the amount of molecule applied to the mucus layer which is delivered to the epithelial cell (delivery efficiency). It may be seen as an increase in the rate (velocity) at which a molecule of interest is delivered. It may be seen as a reduction in the resistance to delivery caused by the mucus (impedance) or an increase in permeability of the mucus to the micro/nanoparticle carrying the molecule (e.g. diffusion coefficient expressed as diffusion in mucus over diffusion in water). It may be seen in a reduction in the return of the micro/nanoparticle carrying the molecule to the apical face of the mucus layer. The Examples describe a number of techniques to assess these characteristics.

Techniques for monitoring the translocation of micro/nanoparticles across mucus layers and the delivery of molecules of interest to epithelial cells underlying a mucus layer are well-established and widely described in the literature. For instance, a convenient technique is the transwell mucus penetration assay, which uses mucus layers formed in transwells as a model representing the mucus layer of a mucosal surface, e.g. as described in the Examples. Similarly, monolayers of mucus secreting cells (e.g. 16HBE41o-cells (immortalized human bronchial epithelial cells)), or tissue sections having a mucosal surface, may be used as the model surface. Information obtained from such assays would be considered representative of what would occur in in vivo contexts. More directly, translocation/delivery may, for instance, be monitored in vivo using micro/nanoparticles and/or molecules of interest carried thereby which are labelled with fluorescent, radioactive, radiocontrast or MRI contrast agents together with appropriate microscopy or other imagining techniques. In other approaches translocation/delivery may be monitored indirectly by following the expression products of and/or the effects on target cells of nucleic acids carried by the micro/nanoparticle. In other embodiments translocation/delivery may be monitored indirectly by following the pharmaceutical/physiological effects of the pharmaceutical molecule of interests or signal from the diagnostic molecule of interest.

As shown in the Examples, alginate oligomers which have at least 70% mannuronate residues are able to reduce the cytotoxicity of cationic micro/nanoparticles and micro/nanoparticles formed of cationic micro/nanoparticle forming components. Thus, in certain embodiments "enhanced translocation of a micro/nanoparticle" or "enhanced delivery of a molecule of interest" in accordance with the invention may be considered to be, or also be, translocation or a micro/nanoparticle or delivery of a molecule with reduced, or less, cytotoxicity as compared to when performed with an equivalent micro/nanoparticle in the absence of an alginate oligomer which has at least 70% mannuronate residues. In these embodiments the relevant cytotoxicity is that of the cells immediately underlying the mucus layer, or region thereof, contacted with the micro/nanoparticle.

In accordance with the invention microparticles may be considered any particle with a particle size in the micrometre range, i.e. from about 1 μm to about 500 μm, e.g. about 1 μm to about 400 μm, 300 μm, 200 μm, 100 μm, 50 μm, 40 μm, 30 μm, 20 μm, 10 μm, or 5 μm, or from about 1 μm, 5 μm, 10 μm, 20 μm, 30 μm, 40 μm, 50 μm, 100 μm, 200 μm, 300 μm, or 400 μm, to about 500 μm. The vesicle may be of particle size of about 5 μm to about 100 μm, e.g. about 5 μm to about 50 μm, 40 μm, 30 μm, 20 μm, or 10 μm or about 10 μm, 20 μm, 30 μm, 40 μm, 50 μm to about 100 μm. The vesicle may be of particle size of about 10 μm to about 200 μm, e.g. about 10 μm to about 100 μm, 50 μm, 40 μm, 30 μm, or 20 μm, or about 20 μm, 30 μm, 40 μm, 50 μm or 100 μm to about 200 μm. Any ranges with endpoints which may be formed from any of the above values are expressly disclosed.

Nanoparticles may be considered any particle with a particle size in the nanometre range, i.e. from about 1 nm to about 1000 nm, e.g. about 1 nm to about 900 nm, 800 nm, 700 nm, 600 nm, 500 nm, 400 nm, 300 nm, 200 nm, 100 nm or 50 nm, or from about 50 nm, 100 nm, 200 nm, 300 nm, 400 nm, 500 nm, 600 nm, 700 nm, 800 nm or 900 nm to about 1000 nm. The vesicle may be of particle size of about 30 nm to about 400 nm, e.g. about 30 nm to about 350 nm, 300 nm, 250 nm, 200 nm, 150 nm, 100 nm, or 50 nm, or about 50 nm, 100 nm, 150 nm, 200 nm, 250 nm, 300 nm or 350 nm to about 400 nm. The vesicle may be of particle size of about 100 nm to about 400 nm, e.g. about 100 nm to about 350 nm, 300 nm, 250 nm, 200 nm, or 150 nm, or about 150 nm, 200 nm, 250 nm, 300 nm, or 350 nm to about 400 nm. The vesicle may be of particle size of about 1 nm to about 50 nm, e.g. about 1 nm to about 40 nm, 35 nm, 30 nm, 25 nm, 20 nm, 15 nm, 10 nm, or 5 nm, or about 5 nm, 10 nm, 15 nm, 20 nm, 25 nm, 30 nm or 35 nm to about 40 nm. Any ranges with endpoints which may be formed from any of the above values are expressly disclosed.

In the context of nanoparticles, the term "particle size" refers to the size of a particle as measured using a dynamic light scattering method (e.g., quasi-elastic light scattering method). For example, particle sizes can be measured using dynamic light scattering instruments (e.g. Zetasizer Nano ZS model manufactured by Malvern Instruments Ltd. and ELS-8000 manufactured by Otsuka Electronics Co., Ltd.). The instruments measure Brownian motion of the particles and particle size is determined based on established dynamic light scattering methodological theory. In the context of microparticles, the term "particle size" refers to the size of a particle as measured using laser diffraction spectroscopy method. Commercial instruments are available and include the Mastersizer 3000 instrument manufactured by Malvern Instruments Ltd.

In contexts in which a population of micro/nanoparticles are considered, the population may have a mode particle size (diameter) of the above-mentioned values or ranges thereof.

In accordance with the invention a cationic micro/nanoparticle is a micro/nanoparticle having a net positive surface charge at physiological pH, i.e. from about pH 6 to about pH 8, e.g. from about pH 6.5 to about pH 7.8, or from about pH 6.8 to about pH 7.5 or from about pH 7.0 to about pH 7.3, or about pH 7.2, and physiological osmolarity.

In accordance with the invention an anionic micro/nanoparticle is a micro/nanoparticle having a net negative surface charge at physiological pH, i.e. from about pH 6 to about pH 8, e.g. from about pH 6.5 to about pH 7.8, or from about pH 6.8 to about pH 7.5 or from about pH 7.0 to about pH 7.3, or about pH 7.2, and physiological osmolarity.

The surface charge of a micro/nanoparticle may be expressed in terms of its zeta potential. Zeta potential may be calculated by analysing dynamic light scattering and so such calculations may, for instance, be performed using the dynamic light scattering instruments mentioned above. A cationic micro/nanoparticle will therefore have a positive zeta potential at physiological osmolarity and pH, e.g. a positive zeta potential of at least about 10 mV, e.g. at least about 20 mV, 25 mV, 30 mV, 35 mV, 40 mV, 45 mV, 50 mV, 55 mV, 60 mV, 65 mV, 70 mV, 75 mV, 80 mV, 85 mV, 90 mV or 95 mV. In other embodiments a cationic micro/nanoparticle may have a zeta potential of less than 20 mV, 25 mV, 30 mV, 35 mV, 40 mV, 45 mV, 50 mV, 55 mV, 60 mV, 65 mV, 70 mV, 75 mV, 80 mV, 85 mV, 90 mV or 95 mV. Any ranges with endpoints which may be formed from any of the above values are expressly disclosed. An anionic micro/nanoparticle will therefore have a negative zeta potential at physiological osmolarity and pH, e.g. a negative zeta potential of at least about (i.e. more negative than) −10 mV, e.g. at least about −20 mV, −25 mV, −30 mV, −35 mV, −40 mV, −45 mV, −50 mV, −55 mV, −60 mV, −65 mV, −70 mV, −75 mV, −80 mV, −85 mV, −90 mV or −95 mV. In certain embodiments an anionic micro/nanoparticle may have a negative zeta potential of no greater than (i.e. less negative than) about −20 mV, −25 mV, −30 mV, −35 mV, −40 mV, −45 mV, −50 mV, −55 mV, −60 mV, −65 mV, −70 mV, −75 mV, −80 mV, −85 mV, −90 mV or −95 mV. Any ranges with endpoints which may be formed from any of the above values are expressly disclosed.

A micro/nanoparticle may have an interior which has a different charge to the surface, e.g. a cationic micro/nanoparticle might have an interior or core which is negatively charged (e.g. containing predominantly of negatively charged components). Thus, in some embodiments the cationic micro/nanoparticle of use in the invention may be a neutral or anionic core coated with a cationic layer (e.g. a layer containing predominantly charged components).

The micro/nanoparticle may be a vesicle (e.g. a liposome (lipoplex), polymersome, noisome, or hybrids thereof (e.g. lipopolyplex)), micelle, virus, virus like particle, dendrimer, metal/metallic particle (e.g. nanocage, nanoshell, nanostar), carbon nanotubes, silica particles, polymeric particles.

Micro/nanoparticles may be solid or hollow, i.e. comprise at least one internal, usually liquid-filled, volume (void). In some arrangements such volumes are entirely surrounded by a lamellar phase. Examples of hollow micro/nanoparticles are vesicles, micelles, viruses, virus like particles, dendrimers, carbon nanotubes, metal/metallic nanocages and metal/metallic nanoshells.

The term "vesicle" is used herein in its broadest sense, i.e. a molecular arrangement of a lamellar phase of amphiphilic vesicle forming compounds fully enclosing and separating an aqueous internal phase from an aqueous external phase. The lamellar phase is a layer, typically a bilayer, formed of amphiphilic compounds, said layer having hydrophilic outer surfaces and at least one a hydrophobic region between said outer surfaces. Vesicles may have a single lamellar phase (unilamellar), multiple concentric lamellar phases (multilamellar) or multiple non-concentric lamellar phases (multivesicular).

In this context the term "formed of amphiphilic vesicle forming compounds" is intended to convey that the one or more amphiphilic compounds are present in the vesicle in amounts effective to form a functional lamellar phase. Thus, the presence of other compounds, e.g. alginate oligomers, within the lamellar phase is not excluded and may themselves be considered vesicle forming compounds in this context. In certain embodiments the one or more amphiphilic vesicle forming compounds will be the predominant component of the lamellar phase, but there might also be embodiments in which said compounds can effect a functional lamellar phase of a vesicle without being the predominant component thereof. Nevertheless, in certain embodiments the lamellar phase will consist substantially, e.g. consist essentially, of said one or more amphiphilic vesicle forming compounds. Expressed numerically at least 50%, 60%, 70%, 80%, 90%, 95%, 99% or 100% (w/w) of the lamellar phase of a vesicle may be the one or more amphiphilic vesicle forming compounds. In certain embodiments the remaining components (e.g. less than 50%, 40%, 30%, 20%, 10% or 5% w/w) of the vesicle are alginate oligomers having at least 70% M residues, but other components may also be present as discussed below.

In a vesicle, the lamellar phase typically encloses an aqueous phase and separates that phase from an aqueous external phase, by which it is meant that the lamellar phase acts as a membrane which inhibits or prevents the diffusion of certain, e.g. hydrophilic, molecules from the internal phase to the external phase and vice versa. The lamellar phase may therefore be described as a partially (e.g. selectively) permeable membrane.

The vesicle may be a liposome, in which case the lamellar phase is a lipid bilayer formed from at least one amphiphilic lipid. Other forms of vesicles include, but are not limited to, polymersomes (amphiphilic block copolymer based lamellar phase) and niosomes (non-ionic surfactant based lamellar phase) and hybrid forms of liposomes, polymersomes and niosomes. Liposomes are a preferred form of vesicle of use in the invention.

The amphiphilic lipids of use in the preparation of liposomes may be any lipid composed of a hydrophilic portion and a hydrophobic portion (typically a hydrophilic head and a hydrophobic tail) that can spontaneously assemble into a bilayer in an aqueous solution. This may include representatives from the cationic lipids, zwitterionic lipids, neutral lipids, or anionic lipids. The use of cationic lipids may provide or at least contribute to the positive charge required to make the micro/nanoparticle cationic in accordance with the invention. In other embodiments non-amphiphilic liposome forming components may provide, or at least contribute to, the positive charge required to make the micro/nanoparticle cationic in accordance with the invention. In certain embodiments the liposomes of use in the present invention are formed from cationic lipids in combination with non-cationic lipids, e.g. neutral lipids, and optionally other liposome forming components.

The hydrophilic portion of useful amphiphilic lipids may comprise polar or charged groups such as carbohydrates, phosphate, carboxylic, sulfato, amino, sulfhydryl, nitro, hydroxy and other like groups. The hydrophobic portion may comprise apolar groups that include without limitation long chain saturated and unsaturated aliphatic hydrocarbon groups and groups substituted by one or more aromatic, cyclo-aliphatic or heterocyclic group(s). Examples of amphipathic lipid compounds include, but are not limited to, phospholipids, aminolipids, glycolipids and sphingolipids.

Cationic lipids contain positively charged functional groups under physiological conditions, e.g. pH. Cationic lipids include, but are not limited to, N,N-dioleyl-N,N-dimethylammonium chloride (DODAC), N,N-distearyl-N,N-dimethylammonium bromide (DDAB), 2,3-dioleoyloxy trimethylammonium propane (DOTAP), 2,3-di-(oleyloxy) propyl trimethyl ammonium (DOTMA), N-[1-(2,3,-ditetradecyloxy)propyl]-N,N-dimethyl-N-hydroxyethylammonium bromide (DMRIE), N-[1-(2,3,dioleyloxy)propyl]-N,N-dimethyl-N-hydroxy ethylammonium bromide (DORIE), 3p-[N—(N',N'-dimethylaminoethane) carbamoyl]cholesterol (DC-Choi), dimethyldioctadecylammonium (DDAB), dioctadecylamidoglycyl spermine (DOGS) and N,N-dimethyl-2,3-dioleyloxy)propylamine (DODMA).

In certain embodiments, the lipids of the liposomes of use in the invention may include anionic or neutral (including zwitterionic and polar) lipids, e.g. anionic or neutral phospholipids. Neutral lipids exist in an uncharged or neutral zwitterionic form at a selected pH. At physiological pH, such lipids include, for example, dioleoylphosphatidylglycerol (DOPG), diacylphosphatidylcholine, diacylphosphatidylethanolamine, ceramide, sphingomyelin, cephalin, cholesterol, cerebrosides and diacyl glycerols. Suitable zwitterionic lipids include, without limitation, dioleoylphosphatidylcholine (DOPC), dimyristoylphosphatidylcholine (DMPC), and dioleoylphosphatidylserine (DOPS). An anionic lipid is a lipid that is negatively charged at physiological pH. These lipids include, without limitation, phosphatidylglycerol, cardiolipin, diacylphosphatidylserine, diacylphosphatidic acid, N-dode-canoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

Anionic and neutral lipids may be referred to herein as non-cationic lipids. Such lipids may contain phosphorus. Examples of non-cationic lipids of use in the liposomes of use in the invention include lecithin, lysolecithin, phosphatidylethanolamine, lysophosphatidylethanolamine, dioleoylphosphatidylethanolamine (DOPE), dipalmitoyl phosphatidylethanolamine (DPPE), dimyristoylphosphoethanolamine (DMPE), distearoylphosphatidy 1-ethanolamine (DSPE), palmitoyloleoylphosphatidylethanolamine (POPE), palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), palmitoyloleyolphosphatidylglycerol (POPG), 16-O-monomethyl PE, 16-O-dimethyl PE, 18-1-trans PE, palmitoyloleoylphosphatidylethanolamine (POPE), 1-stearoyl-2-oleoylphosphatidyethanolamine (SOPE), phosphatidylserine, phosphatidylinositol, sphingomyelin, cephalin, cardiolipin, phosphatidic acid, cerebrosides, dicetylphosphate, and cholesterol.

In other embodiments the amphiphilic lipid may be selected from phosphatidylcholines, e.g. 1,2-dioleoyl-phosphatidylcholine, 1,2-dipalmitoylphosphatidylcholine, 1,2-dimyristoyl-phosphatidylcholine, 1,2-distearoylphosphatidylcholine, 1-oleoyl-2-palmitoyl-phosphatidylcholine, 1-oleoyl-2-stearoyl-phosphatidylcholine, 1-palmitoyl-2-oleoyl-phosphatidylcholine and 1-stearoyl-2-oleoyl-phosphatidylcholine; phosphatidylethanolamines, e.g. 1,2-dioleoylphosphatidylethanolamine, 1,2-dipalmitoylphosphatidylethanolamine, 1,2-dimyristoylphosphatidylethanolamine, 1,2-distearoylphosphatidylethanolamine, 1-oleoyl-2-palmitoyl-phosphatidylethanolamine, 1-oleoyl-2-stearoyl-phosphatidylethanolamine, 1-palmitoyl-2-oleoyl-phosphatidylethanolamine, 1-stearoyl-2-oleoyl-phosphatidylethanolamine and N-succinyl-dioleoylphosphatidylethanolamine; phosphatidylserines, e.g. 1,2-dioleoylphosphatidylserine, 1,2-dipalmitoyl-phosphatidylserine, 1,2-dimyristoyl-phosphatidylserine, 1,2-distearoyl-phosphatidylserine, 1-oleoyl-2-palmitoyl-phosphatidylserine, 1-oleoyl-2-stearoyl-phosphatidylserine, 1-palmitoyl-2-oleoyl-phosphatidylserine and 1-stearoyl-2-oleoyl-phosphatidylserine; phosphatidylglycerols, e.g. 1,2-dioleoyl-phosphatidylglycerol, 1,2-dipalmitoylphosphatidylglycerol, 1,2-dimyristoyl-phosphatidylglycerol, 1,2-distearoyl-phosphatidylglycerol, 1-oleoyl-2-palmitoyl-phosphatidylglycerol, 1-oleoyl-2-stearoyl-phosphatidylglycerol, 1-palmitoyl-2-oleoyl-phosphatidylglycerol and 1-stearoyl-2-oleoyl-phosphatidylglycerol; pegylated lipids; pegylated phospoholipids, e.g. phophatidylethanolamine-N-[methoxy (polyethyleneglycol)-1000], phophatidylethanolamine-N-[methoxy(polyethyleneglycol)-2000], phophatidylethanolamine-N-[methoxy(polyethylene glycol)-3000], phophatidylethanolamine-N-[methoxy(polyethyleneglycol)-5000]; pegylated ceramides, e.g. N-octanoyl-sphingosine-1-{succinyl[methoxy(polyethyleneglycol)1000]}, N-octanoyl-sphingosine-1-{succinyl[methoxy(polyethylene glycol)2000]}, N-octanoyl-sphingosine-1-{succinyl [methoxy(polyethyleneglycol)3000]}, N-octanoyl-sphingosine-1-{succinyl[methoxy(polyethyleneglycol)5000]}; lyso-phosphatidylcholines, lyso-phosphatidylethanolamines, lyso-phosphatidylglycerols, lyso-phosphatidylserines, ceramides; sphingolipids; glycolipids, e.g. ganglioside GM1; glucolipids; sulphatides; phosphatidic acids, e.g. di-palmitoyl-glycerophosphatidic acid; palmitic fatty acids; stearic fatty acids; arachidonic fatty acids; lauric fatty acids; myristic fatty acids; lauroleic fatty acids; physeteric fatty acids; myristoleic fatty acids; palmitoleic fatty acids; petroselinic fatty acids; oleic fatty acids; isolauric fatty acids; isomyristic fatty acids; isostearic fatty acids; sterol and sterol derivatives such as cholesterol, cholesterol hemisuccinate, cholesterol sulphate, and cholesteryl-(4-trimethylammonio)-butanoate, ergosterol, lanosterol; polyoxyethylene fatty acids esters and polyoxyethylene fatty acids alcohols; polyoxyethylene fatty acids alcohol ethers; polyoxyethylated sorbitan fatty acid esters, glycerol polyethylene glycol oxy-stearate; glycerol polyethylene glycol ricinoleate; ethoxylated soybean sterols; ethoxylated castor oil; polyoxyethylene polyoxypropylene fatty acid polymers; polyoxyethylene fatty acid stearates; di-oleoyl-sn-glycerol; dipalmitoyl-succinylglycerol; 1,3-dipalmitoyl-2-succinylglycerol; 1-alkyl-2-acyl-phosphatidylcholines, e.g. 1-hexadecyl-2-palmitoyl-phosphatidylcholine; 1-alkyl-2-acyl-phosphatidylethanolamines such as 1-hexadecyl-2-palmitoyl-phosphatidylethanolamine; 1-alkyl-2-acyl-phosphatidylserines, e.g. 1-hexadecyl-2-palmitoyl-phosphatidylserine; 1-alkyl-2-acyl-phosphatidylglycerols, e.g. 1-hexadecyl-2-palmitoyl-phosphatidylglycerol; 1-alkyl-2-alkyl-phosphatidylcholines, e.g. 1-hexadecyl-2-hexadecyl-phosphatidylcholine; 1-alkyl-2-alkyl-phosphatidylethanolamines, e.g. 1-hexadecyl-2-hexadecyl-phosphatidylethanolamine; 1-alkyl-2-alkyl-phosphatidylserines, e.g. 1-hexadecyl-2-hexadecyl-phosphatidylserine; 1-alkyl-2-alkyl-phosphatidylglycerols, e.g. 1-hexadecyl-2-hexadecyl-phosphatidylglycerol; N-Succinyl-dioctadecylamine; palmitoylhomocysteine; lauryltrimethylammonium bromide; cetyltrimethyl-ammonium bromide; myristyltrimethylammonium bromide; DOTMA; DOTAP; 1,2-dioleoyl-c-(4'-trimethylammonium)-butanoyl-sn-glycerol (DOTB); 1,2-distearoyl-sn-glycero-3-phosphoethanolamine-N-[amino(polyethylene glycol)-2000]; 1,2-distearoyl-sn-glycero-3-phosphoethanolamine-N-[methoxy (polyethylene glycol)-2000] (DSPE-PEG-2000); DSPE-PEG2000-TATE (1,2-distearoyl-sn-glycero-3-phosphoethanolamine-N-[methoxy (polyethylene glycol)-2000]-TATE); and 1-tetradecanoyl-2-octadecanoyl-sn-glycero-3-phosphocholine (MSPC).

Other lipids which may be used may be selected from those disclosed in WO2017/153779, WO2005/117985 and WO03/094974.

In certain embodiments the lipids may be selected from 2,3-di-(oleyloxy)propyl trimethyl ammonium (DOTMA), DHDTMA, DOSEP3, GL67 and 1,2-dioleoyl-sn-glycero-3-phosphoethanolamine (DOPE).

In particular embodiments the lamellar phase may comprise DOPE and DOTMA, e.g. in a weight ratio of (1:1), or DOPE and DHDTMA, e.g. in a weight ratio of (1:1), or DOPE and DOSEP3, e.g. in a weight ratio of (1:1).

The amphiphilic block copolymers of use in the preparation of polymersomes may be any copolymer composed of a hydrophilic polymer and a hydrophobic polymer that can spontaneously assemble into at least a monolayer, typically a bilayer, having hydrophilic outer surfaces and at least one hydrophobic region between said outer surfaces in an aqueous solution. In a preferred embodiment, the amphiphilic block copolymer is a diblock copolymer that has one hydrophilic polymeric region and one hydrophobic polymeric region. In another preferred embodiment, the copolymer is a triblock copolymer that has a hydrophobic polymeric region between a first hydrophilic polymeric region, and a second hydrophilic polymeric region. In polymersomes containing such triblock copolymers, one triblock copolymer substitutes for two diblock copolymers and spans the lamellar phase, thereby forming a monolayer having hydrophilic outer surfaces and a hydrophobic region between said outer surfaces. Block polymers comprising greater numbers of repeating hydrophilic and hydrophobic regions may be used analogously thus forming multi-layered lamellar phases.

In a preferred embodiment, the block copolymer is non-toxic. In a preferred embodiment, the block copolymer is biodegradable. In a preferred embodiment, the block copolymer has a hydrophilic fraction ($f_{EO}$) that supports polymersome formation. For example, the copolymer may have a $f_{EO}$ of equal to or greater than 50%, 40%, 30%, 20%, 10%, or 5%. The hydrophilic region may contain polyethylene glycol, polyethylene oxide, poly(isocyano-L-alanine-L-alanine), polyacrylic acid, poly(methyloxazoline), poly(4-vinyl pyridine), poly-L-glutamic acid, poly(Ne-2-(2-(2-methoxyethoxyl)ethoxy)acetyl-L-lysine, poly(γ-benzyl L-glutamate), or dextran. The polyethylene glycol may be methoxy-poly(ethelyne glycol)$_{5000}$. The hydrophobic region may contain polylactide, poly(lactic acid), poly(ethylethylene), polybutadiene, polycaprolactone, polypropylene sulfide, polystyrene, poly-L-eucine, polyester, poly(butylene oxide), poly(isobutylene), polystyrene-b-poly(isocyanoalanine(2-thiophene-3-ylethyl)amide, poly(2-nitrophenylalanine), poly(γ-methyl-L-caprolactone), or poly(trimethylene carbonate) or hyaluronan. Polymersomes may be rendered cationic, at least in part, by the inclusion of cationic block copolymers, e.g. poly([dimethylamino] ethyl methacrylate). In other embodiments non-amphiphilic polymersome forming components may provide, or at least contribute to, the positive charge required to make the micro/nanoparticle cationic in accordance with the invention. For polymers of chiral molecules, the polymer may contain the D-form, the L-form, or a mixture of the D- and L-forms. For example, the poly(lactic acid) may be poly(D)-(L)-lactic acid. The poly(D)-(L)-lactic acid may have relative percentages of D and L stereoisomers of 10%/90%, 20%/80%, 30%/70%, 40%/60%, 50%/50%, 60%/40%, 70%/30%, 80%/20%, or 90%/10%.

Amphiphilic non-ionic surfactants of use in the preparation of niosomes may be any non-ionic surfactant composed of a hydrophilic portion and a hydrophobic portion that can spontaneously assemble into a bilayer in an aqueous solution. Mixtures of a non-ionic surfactant and a cholesterol or triacylglycerol may also be used. As the non-ionic surfactant, polyoxyethylene sorbitan fatty acid esters, sorbitan fatty acid esters, polyoxyethylene polyoxypropylene copolymers, and the like can be used either individually or in combination. Specific examples of the non-ionic surfactant may include Tween-61, Tween-80, and Span 80, Pluronic F-88 (F88). Specific examples of the cholesterol may include cholesterol, α-cholestanol, β-cholestanol, cholestane, desmosterol (5,24-cholestadiene-3β-ol), sodium cholate, and cholecalciferol. Niosomes may be rendered cationic, at least in part, by the inclusion of cationic lipids, e.g. 2,3-di(tetradecyloxy)propan-1-amine or didodecyldimethylammonium bromide. In other embodiments non-amphiphilic niosome forming components may provide, or at least contribute to, the positive charge required to make the micro/nanoparticle cationic in accordance with the invention.

The vesicle can also contain functionalised vesicle forming compounds. Representative, non-limiting examples of functionalised vesicle forming compounds include sialic acid derivatives, glucuronic acid derivatives; glutaminic acid derivatives; polyglycerin derivatives; polyethylene glycol derivatives (including methoxypolyethylene glycol condensates, etc.), e.g. N-[carbonyl-methoxy polyethylene glycol-2000]-1,2-dipalmitoyl-sn-glycero-3-phosphoethanolamine, N-[carbonyl-methoxy polyethylene glycol-5000]-1,2-dipalmitoyl-sn-glycero-3-phosphoethanolamine, N-[carbonyl-methoxy polyethylene glycol-750]-1,2-distearoyl-sn glycero-3-phosphoethanolamine, N-[carbonyl-methoxy polyethylene glycol-2000]-1,2-distearoyl-sn-glycero-3-phosphoethanolamine (MPEG 2000-distearoyl phosphatidylethanolamine), N-[carbonyl-methoxy polyethylene glycol-5000]-1,2-distearoyl-sn-glycero-3-phosphoethanolamine, DSPE-PEG-2000 and DSPE-PEG2000-TATE.

Any of the above vesicle forming compounds may be derivatised with receptor affinity molecules to assist in the targeting of the vesicle to a chosen target site. Such affinity molecules include receptor specific polypeptides, nucleic acids and carbohydrates, e.g. antibodies, antibody fragments, peptide growth factors, DNA and RNA. Said receptors may be polypeptides (e.g. integrins, cadherins, selectins, ICAM-1), nucleic acids or carbohydrates. A plethora of receptor-ligand pairs are known to the skilled person and may be identified without undue burden and any of these pair could provide the basis of the choice of receptor affinity molecule for use in the invention. Examples include the peptide ligands described in WO96/15811, WO98/54347, WO01/92543, WO02/072616, WO2004108938, and WO2007/138324. Receptor ligand derivatised liposome forming compounds may include those described in WO2007/138324. In certain embodiments the receptor affinity molecule is not a molecule of interest, not an alginate oligomer or is not itself (i.e. when not coupled to another chemical entity) a self-assembling micro/nanoparticle forming agent.

Techniques for preparing the vesicles of use in the invention are well known and well established and thus entirely routine. Discussion of the technology may be found in Huang Z, et al., 2014, Progress involving new techniques for liposome preparation, Asian Journal of Pharmaceutical Sciences, Vol 9(4):176-82; Torchilin V P., 2012, Multifunctional nanocarriers, Advanced Drug Delivery Reviews, Vol 64(SUPPL.):302-15; Vemuri S, et al, 1995, Preparation and characterization of liposomes as therapeutic delivery systems: a review, Pharmaceutica Acta Helvetiae, Vol 70(2): 95-111; Carugo, D., et al, 2016, Liposome production by microfluidics: potential and limiting factors, Scientific Reports, 6:25876; Erdoyan S, et al, 2006, Thrombus localization by using streptokinase containing vesicular systems, Drug Delivery, Vol 13(4):303-9; and Meng F, et al, 2011, Polymersomes spanning from nano- to microscales: Advanced vehicles for controlled drug delivery and robust vesicles for virus and cell mimicking, Journal of Physical Chemistry Letters, Vol 2(13):1533-9 the contents of which are incorporated herein by reference.

In broad terms vesicular micro/nanoparticles may be prepared using batch techniques that give rise to a heterogeneous population of vesicles within a macroscale environment or by using microfluidic methods in which vesicle formation takes place in a confined microenvironment and as such may give rise to a more homogenous population of vesicles on account of the greater control which may be exerted on the physical parameters of the microenvironment in which the vesicles form.

The bulk methods may be sub-classified into those methods based on the swelling of initially dried preorganised films of vesicle forming compounds (i.e. rehydration methods), followed by the mechanical manipulation of the dispersed bilayers and those methods involving the use of: (i) a cosolvent in which the vesicle forming compounds are soluble, (ii) an additional non-bilayer-forming "coamphiphile", or (iii) specific ionic species that influence the supramolecular aggregation of the vesicle forming compounds.

Microfluidic methods are described widely in the literature and include those referred to as electroformation and hydration, extrusion, pulsed jetting, double emulsion templating, ice droplet hydration, transient membrane ejection, droplet emulsion transfer, hydrodynamic pinch-off and hydrodynamic focusing. Microfluidic hydrodynamic focusing may be used advantageously in accordance with the invention.

Thus, in accordance with the invention the micro/nanoparticles formed of amphiphilic self-assembling micro/nanoparticle forming compounds may be prepared by any of the methods described herein for the formation of vesicular micro/nanoparticles, in particular a bulk production method or a microfluidic production method (e.g. electroformation and hydration, extrusion, pulsed jetting, double emulsion templating, ice droplet hydration, transient membrane ejection, droplet emulsion transfer, hydrodynamic pinch-off and hydrodynamic focusing).

Thus, in certain embodiments the methods of the invention involving a micro/nanoparticle formed of amphiphilic self-assembling micro/nanoparticle forming compounds may comprise a further step in which the micro/nanoparticle is prepared, e.g. by any of the methods described herein for the formation of vesicular micro/nanoparticles, in particular a bulk production method or a microfluidic production method.

The micro/nanoparticles of use in the invention may be micelles. Micelles are spherical self-assembling supramolecular assemblies of amphiphilic compounds in which hydrophilic regions contact the surrounding aqueous phase as an outer shell and hydrophobic regions sequester in the micelle's centre forming a continuous hydrophobic core. Any of the above mentioned amphiphilic compounds may be formed into micelles, e.g. by providing said compounds in an aqueous solution above the critical micelle concentration for the compound or combination thereof which is used. The presence of other components in the micelle and/or functionalised amphiphilic compounds as described above for vesicle micro/nanoparticles may be used in the context of micelle micro/nanoparticles. Micelles may be rendered cationic, at least in part, by the inclusion of cationic amphiphilic compounds, e.g. as described above. In other embodiments non-amphiphilic micelle forming components may provide, or at least contribute to, the positive charge required to make the micro/nanoparticle cationic in accordance with the invention.

The micro/nanoparticles of use in the invention may be viruses, in particular a virus carrying a nucleic acid vector or a heterologous peptide (a peptide not present in the wild type virus). Such viruses may conveniently be used to deliver therapeutic or diagnostic peptides or vectors comprising therapeutic or diagnostic nucleic acids to the epithelial cells of a target mucosal surface, e.g. the surfaces of the respiratory tract, the GI tract and the reproductive tract. More generally, viruses themselves may be active components for vaccines against the virus, and/or may deliver heterologous peptide antigens carried by the virus or expressed from nucleic acid vectors carried by the virus. Viruses, e.g. virus vectors, of use in accordance with the invention include retroviruses, adenoviruses, adeno-associated viruses, lentiviruses, pox viruses, alphaviruses, and herpes viruses and hybrids thereof. In other embodiments the virus may be an oncolytic virus, i.e. a virus that preferentially infects and kills cancer cells. Oncolytic viruses may, for example, be selected from oncolytic forms of adenovirus, reovirus, measles virus, herpes simplex virus, vesicular stomatitis virus, poliovirus, Newcastle disease virus, Semliki Forest virus, vaccinia, senecavirus, maraba virus and enterovirus.

Virus like particles are non-pathogenic micro/nanoparticles which form by self-assembly when structural virus proteins are expressed in suitable host cells. Viral nucleic acid is not packaged into the particles during self-assembly. Such particles may act as vaccine antigens and/or may be engineered to carry molecules of interest in accordance with the invention by covalently linking such molecules of the structural virus protein or by having self-assembly take place in the presence of the molecule of interest. Virus like particles may be formed from the structural proteins of retroviruses, adenoviruses, adeno-associated viruses, lentiviruses, pox viruses, alphaviruses, herpes viruses and hepatitis virus.

Carbon nanotubes are allotropes of carbon with a cylindrical structure in the nanometre or micrometre range. The cylindrical structure may be a single layer (single walled nanotube) or multiple layer (multi-walled nanotube). These structures may be prepared in a number of ways well-described in the literature, e.g. chemical vapour deposition, arc discharge, high-pressure carbon monoxide disproportionation, and laser ablation. Carbon nanotubes may be rendered cationic by surface functionalization or by the inclusion of cationic components in or on the micro/nanoparticle.

Dendrimers are highly branched, star-shaped macromolecules with nanometer-scale dimensions. Dendrimers are defined by three components: a central core, an interior dendritic structure (the branches), and an exterior surface with functional surface groups. By varying the combination of these components dendrimers of different shapes and sizes with shielded interior cores and particular surface characteristics, e.g. positive surface charge. Dendrimers are synthesized by step-wise chemical methods to give distinct generations (G0, G1, G2, . . . ) of molecules with narrow molecular weight distribution, uniform size and shape, and multiple (multivalent) surface groups. Dendrimers of use in accordance with the invention may include polyamidoamine (PAMAM) dendrimers, polypropylenimine dendrimers, thiophosphoryl dendrimers, cyclotriphosphazene dendrimers, and 2,2-bis(hydroxymethyl)propionic acid (bis-MPA) dendrimers. Dendrimers may be rendered cationic, at least in part, by the use of cationic structural components and/or by the use of cationic functional surface groups and/or the inclusion of other cationic components in or on the micro/nanoparticle.

Examples of solid micro/nanoparticles include polymeric micro/nanoparticles, silica micro/nanoparticles and metal micro/nanoparticles.

Polymeric micro/nanoparticles may be formed (including by self-assembly (polyplexes), layer-by-layer assembly or by gelation, e.g. hydrogelation) from/of any suitable polymer, e.g. polystyrene, polylactic acid, polyacrylamide, melamine, poly(D-L-lactide), poly-D-L-glycolide, polyalkylcyanoacrylate, poly(lactide-co-glycolide) PLA, polycaprolactone, chitosan, gelatine, albumin, dextran, agarose, poly-L-glutamic acid, poly L-lysine. Polymeric micro/nanoparticles may be rendered cationic, at least in part, by the inclusion of cationic polymers, e.g. poly L-lysine, and/or by surface functionalization or the inclusion of other cationic components in or on the micro/nanoparticle.

Metal and metallic micro/nanoparticles may be formed from/of the following metals and their isotopes: gold (e.g. $^{198}$Au, $^{199}$Au), silver (e.g. $^{107}$Ag and $^{109}$Ag), platinum (e.g. $^{195m}$Pt), iron (e.g. $^{59}$Fe), copper (e.g. $^{61}$Cu, $^{64}$Cu, and $^{67}$Cu), gadolinium (e.g. $^{149}$Gd, $^{151}$Gd), indium (e.g. $^{111}$In), technetium (e.g. $^{99m}$Tc), gallium (e.g. $^{67}$Ga, $^{68}$Ga), rhenium (e.g. $^{188}$Re, $^{186}$Re), lutetium (e.g. $^{177}$Lu), actinium (e.g. $^{225}$Ac), yttrium (e.g. $^{90}$Y), antimony (e.g. $^{119}$Sb), tin (e.g. $^{117}$Sn, $^{13}$Sn), dysprosium (e.g. $^{159}$Dy), cobalt (e.g. $^{56}$Co, $^{60}$Co), ruthenium (e.g. $^{97}$Ru, $^{103}$Ru, $^{106}$Ru), palladium (e.g. $^{103}$Pd), cadmium (e.g. $^{15}$Cd), tellurium (e.g. $^{118}$Te, $^{123}$Te), barium (e.g. $^{131}$Ba, $^{140}$Ba), terbium (e.g. $^{160}$Tb), lanthanum (e.g. $^{140}$La), radium (e.g. $^{223}$Ra, $^{224}$Ra), strontium (e.g. $^{89}$Sr), samarium (e.g. $^{153}$Sm), ytterbium (e.g. $^{169}$Yb), thallium (e.g. $^{201}$T), caesium (e.g. $^{137}$Cs), iridium (e.g. $^{192}$Ir) and rubidium (e.g. $^{82}$Rb). The metal may appear in any of the existing oxidation states for the metal. These oxidation states include monovalent cations, divalent cations, trivalent cations, tetravalent cations, pentavalent cations, hexavalent cations and heptavalent cations. Functionalization of the particles, e.g.

with ammonium-based species (arginine, polyethylene imine, etc.) or phosphonium-based species (phosphonioalkylthiosulfate, phosphonioalkylthioacetate) may provide a cationic surface charge. The metal/metallic micro/nanoparticles may be a micro/nanosphere, a micro/nanostar, micro/nanocage or micro/nanoshell.

The silica micro/nanoparticles may be mesoporous silica.

In certain embodiments the micro/nanoparticles of use in the invention may further comprise components which are or which carry receptor affinity molecules to assist in the targeting of the micro/nanoparticle to a chosen target site. Such affinity molecules include receptor specific polypeptides, nucleic acids and carbohydrates, e.g. antibodies, antibody fragments, peptide growth factors, DNA and RNA. Said receptors may be polypeptides (e.g. integrins, cadherins, selectins, ICAM-1), nucleic acids or carbohydrates. A plethora of receptor-ligand pairs are known to the skilled person and may be identified without undue burden and any of these pair could provide the basis of the choice of receptor affinity molecule for use in the invention. Examples include the peptide ligands described in WO96/15811, WO98/54347, WO01/92543, WO02/072616, WO2004108938, and WO2007/138324. Receptor affinity molecules may include those described in WO2007/138324 in the context of receptor affinity molecule derivatised liposome forming compounds. In certain embodiments the receptor affinity molecule is not a molecule of interest, not an alginate oligomer or is not itself (i.e. when not coupled to another chemical entity) a self-assembling micro/nanoparticle forming agent.

As discussed above, in certain embodiments the micro/nanoparticles of use in the invention carry a molecule of interest, in particular a molecule to be delivered to an epithelial cell of a mucosal surface. Such molecules may include therapeutically active agents (pharmaceuticals/drugs), diagnostic or imaging agents or agents for engineering the properties of the cell or products the cell produces (for instance, enzymes, cofactors, precursor substances, substrates). The therapeutic agent may in particular be a small molecule pharmaceutical, a biological therapeutic or a radiopharmaceutical (e.g. a radionuclide or a radioimmunotherapeutic). Biological therapeutics include, but are not limited to antibodies, peptide hormones, cytokines, peptide growth factors, peptide antigens and nucleic acids (e.g. nucleic acids for use in gene therapy, gene editing, RNA interference therapy (e.g. siRNA or miRNA), antisense therapy and in vitro transcribed mRNA (IVT-mRNA) therapy. The diagnostic agent may include radiodiagnostics (e.g. diagnostic radionuclides), contrast agents or a nucleic acid or protein for use as a molecular probe (e.g. oligonucleotides and antibodies). Cell engineering agents may include nucleases (e.g. Cas9, Cpf1), proteases, lipases, and co-factors.

The therapeutically active agent may be a CFTR modulator, an antibiotic, an antifungal, an antiviral, an cytotoxic chemotherapy agent, an angiogenesis inhibitor, an anti-cancer monoclonal antibody, a radioimmunotherapeutic, an immunostimulatory agent, an immunosuppressant, a corticosteroid, a non-steroidal anti-inflammatory drug (NSAID), a bronchodilator, an oral antidiabetic drug, or a radiopharmaceutical.

CFTR modulators are small molecules which can redress, at least partially, CFTR dysfunction. CFTR modulators may be classed as CFTR potentiators, CFTR correctors and read-through agents.

CFTR potentiators are CFTR modulators which increase the activity of the CFTR ion channel present on the epithelial cell surface (e.g. by increasing the open probability (the gate opening time and/or the gating probability) or conductance of the channel). This may take the form of increasing ion channel activity from a reduced level in a defective CFTR or increasing the ion channel activity above normal levels in a population of normal CFTR of reduced size.

CFTR correctors are CFTR modulators which increase the amount of CFTR protein delivered or retained at the epithelial cell surface. These molecules may achieve this effect in a variety of ways in view of the variety of defects in the processing of CFTR that can cause reduced quantities of CFTR at the epithelial cell surface. For instance, certain CFTR correctors can act as a chaperone facilitating proper folding and post-translational modification of CFTR, protecting CFTR from premature degradation, facilitating intracellular targeting of CFTR and reversing accelerated turnover of CFTR at the cell membrane. This may take the form of increasing the amount of normal CFTR protein delivered or to retained at the epithelial cell surface to levels reflecting healthy cells or increasing the amount of partially defective CFTR protein delivered or to retained at the epithelial cell surface, e.g. to levels greater than that seen with wild type CFTR in healthy cells.

Read-through agents are CFTR modulators which cause the translation machinery of the cell to pass over any premature termination codons in the CFTR mRNA transcript thereby increasing the amount of substantially full length and preferably functional CFTR produced.

In certain embodiments the CFTR modulator is selected from those disclosed in WO2006/002421, WO2007/056341 WO2007134279, WO2009038683, WO2009064959, WO2009073757, WO2009076141, WO2009076142, WO2010019239, WO2010037066, WO2010048526, WO2010053471, WO2010054138, WO2010138484, WO2011019413, WO2011050325, WO2011072241, WO2011127241, WO2011127290, WO2011133751, WO2011133951, WO2011133953, WO2011133956, WO2011146901, Pedemonte, N., et al., J Clin Invest. 2005; 115(9):2564-2571, Van Goor, F. et al., Am J Physiol Lung Cell Mol Physiol 2006, 290: L1117-L1130, and Pedemonte, N., et al., Molecular Pharmacology, 2005 vol. 67 no. 5 1797-1807 the content of which is incorporated herein by reference.

Particular mention may be made of potentiators in the phenylglycine, sulphonamide (as reported by Pedemonte et al., Molecular Pharmacology, 2005), pyrazole (e.g. [4-methyl-2-(5-phenyl-1H-pyrazol-3-yl)phenol] as reported Van Goor, F. et al, Am J Physiol Lung Cell Mol Physiol 2006), flavone (e.g. the isoflavones and benzoflavones, in particular genistein and apigenin), xanthine (e.g. isobutylmethylxamine (IBMX), 8-cyclopentyl-1,3-dipropylxanthine (CPX), 1-isobutylxanthine (XC-33)), benzothiophene (e.g. tetrahydrobenzothiophene), benzimidazolone (e.g. NS004, 5-trifluoromethyl-1-(5-chloro-2-hydroxyphenyl)1,3-dihydro-2H-benzimi-dazol-2-one; NS1619, 1,3-dihydro-1-[2-hydroxy-5-(trifluoromethyl)phenyl]-5-(trifluoromethyl)-2H-benzimidazol-2-one), capsaicin, fluorescein (e.g. phloxine B), phenantroline, benzoquinoline, dihydropyridine (e.g. the 1,4-dihydropyridines, in particularfelodipine), isoquinoline, and benzo[c]quinolizinium (e.g. MPB-27 (6-hydroxy-7-chlorobenzo[c]quinolizinium), MPB-07 (6-hydroxy-10-chlorobenzo[c]quinolizinium), MPB-91 (5-butyl-10-chloro-6-hydroxybenzo[c]quinolizinium chloride), MPB-104 (5-butyl-7-chloro-6-hydroxybenzo[c]quinolizinium chloride) as reported in Norez et al, J. Pharmacology and Experimental Therapeutics, 2008, 325, 89-99)) classes. Further modulators and corresponding molecular structures of use in the invention are shown in FIG. 10.

CFTR correctors include 4-phenylbutyrate (4-PBA), 1,2,3,4-tetrahydroisoquinoline-3-carboxylic acid diamides, compounds in the isoquinoline, cycloalkylcarboxamido-pyridine benzoic acid and benzo[c]quinolizinium classes (e.g. MPB-07, MPB-80 (10-fluoro-6-hydroxybenzo[c]quinolizinium chloride) MPB-91 and MPB 104) and compounds in various other structural classes as reported by Pedemonte et al. J. Clin. Invest. (2005) and Van Goor, F. et al. Am J Physiol Lung Cell Mol Physiol (2006) and shown in FIG. 3 (aminobenzothiazoles (e.g. 2-aminobenzothiazoles), aminoarylthiazoles (e.g. 2-amino-4-arylthiazoles), quinazolinones (e.g. quinazolinylaminopyrimidones (in particular 2-quinazolinyl-4-aminopyrimidinones), bisaminomethylbithiazoles, N-phenylaminoquinolines (e.g. (N-phenylamino)quinolones)).

Representative CFTR modulators include N-(2,4-di-tert-butyl-5-hydroxyphenyl)-1,4-dihydro-4-oxoquinoline-3-carboxamide (ivacaftor; VX-770), [4-methyl-2-(5-phenyl-1H-pyrazol-3-yl)phenol] (VRT-532), VRT-422, 4-cyclohexyloxy-2-{1-[4-(4-methoxy-benzenesulfonyl)-piperazin-1-yl]-ethyl}-quinazoline (VRT-325) (both in Van Goor, F. et al. Am J Physiol Lung Cell Mol Physiol (2006) and FIG. 3), 3-[6-[[1-(2,2-difluoro-1,3-benzodioxol-5-yl) cyclopropanecarbonyl]amino]-3-methylpyridin-2-yl]benzoic acid (lumacaftor; VX-809), VX-661 (tezacaftor; 1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide), N6022 (3-[1-(4-carbamoyl-2-methylphenyl)-5-(4-imidazol-1-ylphenyl)pyrrol-2-yl]propanoic acid), ataluren, 1,2,3,4-tetrahydroisoquinoline-3-carboxylic acid diamides, 4-phenylbutyrate (4-PBA), genistein, apigenin, MPB-07, MPB-27, MPB-91, MPB-104, felodipine, NS004, phloxine B, IBMX, CPX, XC-33, capsaicin and gentamicin, preferably ivacaftor, lumacaftor, VX-661, and ataluren and most preferably ivacaftor and lumacaftor.

Of the above mentioned CFTR modulators, the following are considered potentiators: VX-770, VTR-532, genistein, apigenin, MPB-07, MPB-27, MPB-91, MPB-104, felodipine, NS004, phloxine B, IBMX, CPX, XC-33, capsaicin and genistein. Of the above mentioned CFTR modulators, the following are considered correctors: VRT-422, VRT-325, VX-809, VX-661, N6022, 1,2,3,4-tetrahydroisoquinoline-3-carboxylic acid diamides, 4-phenylbutyrate (4-PBA), MPB-07, MPB 80, MPB-91 and MPB-104. Of the above mentioned CFTR modulators, the following are considered read through agents: ataluren and gentamicin.

The antibiotic may be selected from the aminoglycosides (e.g. amikacin, gentamicin, kanamycin, neomycin, netilmicin, streptomycin, tobramycin); the β-lactams (e.g. the carbecephems (e.g. loracarbef); the 1st generation cephalosporins (e.g. cefadroxil, cefazolin, cephalexin); 2nd generation cephalosporins (e.g. cefaclor, cefamandole, cephalexin, cefoxitin, cefprozil, cefuroxime); 3rd generation cephalosporins (e.g. cefixime, cefdinir, cefditoren, cefoperazone, cefotaxime, cefpodoxime, ceftazidime, ceftibuten, ceftizoxime, ceftriaxone); 4th generation cephalosporins (e.g. cefepime); the monobactams (e.g. aztreonam); the macrolides (e.g. azithromycin, clarithromycin, dirithromycin, erythromycin, troleandomycin); the monobactams (e.g. aztreonam); the penicillins (e.g. amoxicillin, ampicillin, carbenicillin, cloxacillin, dicloxacillin, nafcillin, oxacillin, penicillin G, penicillin V, piperacillin, ticarcillin); the polypeptide antibiotics (e.g. bacitracin, colistin, polymyxin B); the quinolones (e.g. ciprofloxacin, enoxacin, gatifloxacin, levofloxacin, lomefloxacin, moxifloxacin, norfloxacin, ofloxacin, trovafloxacin); the sulfonamides (e.g. mafenide, sulfacetamide, sulfamethizole, sulfasalazine, sulfisoxazole, trimethoprim-sulfamethoxazole); the tetracyclines (e.g. demeclocycline, doxycycline, minocycline, oxytetracycline, tetracycline); the glycylcyclines (e.g. tigecycline); the carbapenems (e.g. imipenem, meropenem, ertapenem, doripenem, panipenem/betamipron, biapenem, PZ-601); other antibiotics include chloramphenicol; clindamycin, ethambutol; fosfomycin; isoniazid; linezolid; metronidazole; nitrofurantoin; pyrazinamide; quinupristin/dalfopristin; rifampin; spectinomycin; and vancomycin.

More preferably the antibiotic is selected from amikacin, gentamicin, kanamycin, neomycin, netilmicin, streptomycin, tobramycin, cefixime, cefdinir, cefditoren, cefoperazone, cefotaxime, cefpodoxime, ceftazidime, ceftibuten, ceftizoxime, ceftriaxone, cefepime, aztreonam, amoxicillin, ampicillin, carbenicillin, cloxacillin, dicloxacillin, nafcillin, oxacillin, penicillin G, penicillin V, piperacillin, ticarcillin, ciprofloxacin, enoxacin, gatifloxacin, levofloxacin, lomefloxacin, moxifloxacin, norfloxacin, ofloxacin, trovafloxacin, azithromycin, clarithromycin, dirithromycin, erythromycin, roxithromycin, telithromycin, CarbomycinA, josamycin, kitasamycin, midecamicine, oleandomycin, spiramycin, troleandromycin, tylosin, imipenem, meropenem, ertapenem, doripenem, panipenem/betamipron, biapenem, PZ-601, bacitracin, colistin, polymyxin B, demeclocycline, doxycycline, minocycline, oxytetracycline and tetracycline.

More preferably the antibiotic is selected from aztreonam, ciprofloxacin, gentamicin, tobramycin, amoxicillin, colistin, ceftazidime, azithromycin, clarithromycin, dirithromycin, erythromycin, roxithromycin, spiramycin, oxytetracycline, and imipenem.

In particularly preferred embodiments the antibiotic is selected from aztreonam, ciprofloxacin, gentamicin, tobramycin, amoxicillin, colistin and ceftazidime.

Representative antifungals include, but are not limited to the polyenes (e.g. natamycin, rimocidin, filipin, nystatin, amphotericin B, candicin; the imidazoles (e.g. miconazole, ketoconazole, clotrimazole, econazole, bifonazole, butoconazole, fenticonazole, isoconazole, oxiconazole, sertaconazole, sulconazole, tioconazole); the triazoles (e.g. fluconazole, itraconazole, isavuconazole, ravuconazole, posaconazole, voriconazole, terconazole); the allylamines (e.g. terbinafine, amorolfine, naftifine, butenafine); and the echinocandins (e.g. anidulafungin, caspofungin, micafungin).

Representative antivirals include, but are not limited to abacavir, acyclovir, adefovir, amantadine, amprenavir, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, nelfinavir, nevirapine, nexavir, oseltamivir, penciclovir, peramivir, pleconaril, podophyllotoxin, raltegravir, ribavirin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

Representative immunostimulatory agents include, but are not limited to cytokines e.g. TNF, IL-1, IL-6, IL-8.

Representative NSAIDs include, but are not limited to, the salicylates (e.g. aspirin (acetylsalicylic acid), choline magnesium trisalicylate, diflunisal, salsalate, the propionic acid derivatives (e.g. ibuprofen, dexibuprofen, dexketoprofen, fenoprofen, flurbiprofen, ketoprofen, loxoprofen, naproxen, oxaprozin), the acetic acid derivatives (e.g. aceclofenac, diclofenac, etodolac, indomethacin, ketorolac, nabumetone, tolmetin, sulindac), the enolic acid derivatives (e.g. droxicam, isoxicam, lornoxicam, meloxicam, piroxicam, tenoxicam), the anthranilic acid derivatives (e.g. flufenamic acid, meclofenamic acid, mefenamic acid, tolfenamic acid) and the selective COX-2 inhibitors (Coxibs; e.g. celecoxib, etoricoxib, lumiracoxib, parecoxib, rofecoxib, valdecoxib). The propionic acid derivatives (e.g. ibuprofen, dexibuprofen, dexketoprofen, fenoprofen, flurbiprofen, ketoprofen, loxoprofen, naproxen, oxaprozin) are preferred, ibuprofen being most preferred.

Representative examples of suitable bronchodilators include but are not limited to the β2 agonists (e.g. the short-acting β2 agonists (e.g. pirbuterol, epinephrine, salbutamol, levosalbutamol, clenbuterol, terbutaline, procaterol, metaproterenol, fenoterol, bitolterol mesylate, ritodrine, isoprenaline); the long-acting β2 agonists (e.g. salmeterol, formoterol, bambuterol, clenbuterol); and the ultra-long-acting β2 agonists (e.g. indacaterol)), the anticholinergics (e.g. ipratropium, oxitropium, tiotropium) and theophylline.

Representative examples of suitable corticosteroids include but are not limited to prednisone, flunisolide, triamcinolone, fluticasone, budesonide, mometasone, beclomethasone, amcinonide, budesonide, desonide, fluocinonide, fluocinolone, halcinonide, hydrocortisone, cortisone, tixocortol, prednisolone, methylprednisolone, prednisone, betamethasone, dexamethasone, fluocortolone, aclometasone, prednicarbate, clobetasone, clobetasol, and fluprednidene.

Representative examples of suitable oral antidiabetic drugs include, but are not limited to, the sulfonylureas (e.g. carbutamide, acetohexamide, chlorpropamide, tolbutamide, glipizide, gliclazide, glibenclamide, glibornuride, gliquidone, glisoxepide, glyclopyramide, glimepiride), the biguanides (e.g. metformin, phenformin, buformin, proguanil), the thiazolidinediones (e.g. rosiglitazone, pioglitazone, troglitazone), the alpha-glucosidase inhibitors (e.g. acarbose, miglitol, voglibose), the meglitinides (e.g. nateglinide, repaglinide, mitiglinide), and the glycosurics (e.g. dapagliflozin, ganagliflozin, ipragliflozin, tofogliflozin, empagliflozin, sergliflozin etabonate, remogliflozin etabonate).

Representative examples of suitable cytotoxic chemotherapy agents include, but are not limited to, bleomycin, capecitabine, carboplatin, cisplatin, cyclophosphamide, dacarbazine, docetaxel, doxorubicin, pegylated liposomal doxorubicin, epirubicin, eribulin, etoposide, fluorouracil, gemcitabine, ixabepilone, methotrexate, mechlorethamine, oxaliplatin, paclitaxel, procarbazine, prednisolone, protein-bound paclitaxel, vinorelbine, vinblastine and vincristine.

Representative examples of suitable angiogenesis inhibitors include, but are not limited to, bevacizumab, everolimus, lenalidomide, ramucirumab sorafenib, sunitinib and thalidomide.

Representative examples of suitable anti-cancer monoclonal antibody include, but are not limited to, alemtuzumab, bevacizumab, cetuximab, ofatumumab, panitumumab, rituximab, and trastuzumab and the checkpoint inhibitors ipilimumab, nivolumab, pembrolizumab, atezolizumab, avelumab, durvalumab, and cemiplimab.

Representative examples of suitable radioimmunotherapeutics include, but are not limited to, ibritumomab and tositumomab.

Representative examples of therapeutic radionuclides include, but are not limited to, Indium (e.g. $^{111}$In), Technetium (e.g. $^{99m}$Tc), Gallium (e.g. $^{67}$Ga, $^{68}$Ga), Rhenium (e.g. $^{188}$Re, $^{186}$Re), Lutetium (e.g. $^{177}$Lu), Actinium (e.g. $^{22}$Ac), Yttrium (e.g. $^{90}$Y), Antimony (e.g. $^{119}$Sb), Tin (e.g. $^{117}$Sn, $^{113}$Sn), Dysprosium (e.g. $^{159}$Dy), Cobalt (e.g. $^{56}$Co, $^{60}$Co), Iron (e.g. $^{59}$Fe), Copper (e.g. $^{61}$Cu, $^{64}$Cu, and $^{67}$Cu), Ruthenium (e.g. $^{97}$Ru, $^{103}$Ru, $^{106}$Ru), Palladium (e.g. $^{103}$Pd), Cadmium (e.g. $^{115}$Cd), Tellurium (e.g. $^{18}$Te, $^{123}$Te), Barium (e.g. $^{131}$Ba, $^{140}$Ba), Gadolinium (e.g. $^{149}$Gd, $^{151}$Gd), Terbium (e.g. $^{160}$Tb), Gold (e.g. $^{198}$Au, $^{199}$Au), Lanthanum (e.g. $^{140}$La), Radium (e.g. $^{223}$Ra, $^{224}$Ra), Strontium (e.g. $^{89}$Sr), Samarium (e.g. $^{153}$Sm), Ytterbium (e.g. $^{169}$Yb), Thallium (e.g. $^{201}$T), Caesium (e.g. $^{137}$Cs), Iridium (e.g. $^{192}$Ir) and Rubidium (e.g. $^{82}$Rb).

Representative examples of diagnostic radionuclides include, but are not limited to Indium (e.g. $^{111}$In), Technetium (e.g. $^{99m}$Tc), Gallium (e.g. $^{67}$Ga, $^{68}$Ga), Rubidium (e.g. $^{82}$Rb) and Thallium (e.g. $^{201}$T).

The above mentioned radionuclide may appear in any of the existing oxidation states for the metal. These oxidation states include monovalent cations, divalent cations, trivalent cations, tetravalent cations, pentavalent cations, hexavalent cations and heptavalent cations.

Representative examples of suitable immunosuppressants include, but are not limited to, cyclosporine, rapamycin, tacrolimus, dactinomycin, mitomycin c, bleomycin, mithramycin, azathioprine, hydrocortisone, cortisone, prednisone, prednisolone, methylprednisolone, bexamethasone, betamethasone, triamcinolone, beclomethasone, fludrocortisone acetate, deoxycorticosterone acetate and aldosterone.

In certain embodiments the therapeutic nucleic acid may comprise a gene encoding a functional version of a protein which is dysfunctional in a subject, e.g. the CFTR gene. In other embodiments the nucleic acid may be an IVT-mRNA molecule, or encode or be an siRNA molecule, an miRNA molecule, or an antisense RNA molecule, which targets a dysfunctional gene or a gene which is being overexpressed, e.g. an oncogene. In other embodiments the nucleic acid may encode or be some or all of the components (e.g. the nuclease, the sgRNA, the crRNA, the tracrRNA or a DNA repair template) of a CRISPR system, e.g. CRISPR-Cas9, CRISPR-Cas13, and CRISPR-Cpf1. Asa diagnostic, the nucleic acid may be complimentary to the nucleotide sequence of a nucleic acid biomarker indicative of a disease or condition or the progress thereof. In other contexts, e.g. in vitro cell or tissue culture, such nucleic acids may be used to engineer the properties of cells or products cells produce.

As noted above, alginates typically occur as polymers of an average molecular mass of at least 35,000 Daltons, i.e. approximately 175 to approximately 190 monomer residues, although typically much higher and an alginate oligomer according to the present invention may be defined as a material obtained by fractionation (i.e. size reduction) of an alginate polymer, commonly a naturally occurring alginate. An alginate oligomer can be considered to be an alginate of an average molecular weight of less than 35,000 Daltons (i.e. less than approximately 190 or less than approximately 175 monomer residues), in particular an alginate of an average molecular weight of less than 30,000 Daltons (i.e. less than approximately 175 or less than approximately 150 monomer residues) more particularly an average molecular weight of less than 25,000 or 20,000 Daltons (i.e. less than approximately 135 or 125 monomer residues or less than approximately 110 or 100 monomer residues).

Viewed alternatively, an oligomer generally comprises 2 or more units or residues and an alginate oligomer for use according to the invention will typically contain 2 to 100 monomer residues, more typically 3, 4, 5 or 6 to 100, and may contain 2, 3, 4, 5 or 6 to 75, 2, 3, 4, 5 or 6 to 50, 2, 3, 4, 5 or 6 to 40, 2, 3, 4, 5 or 6 to 35 or 2, 3, 4, 5 or 6 to 30 residues. Thus, an alginate oligomer for use according to the invention will typically have an average molecular weight of 350, 550, 700, 900 or 1000 to 20,000 Daltons, 350, 550, 700, 900 or 1000 to 15,000 Daltons, 350, 550, 700, 900 or 1000 to 10,000 Daltons, 350, 550, 700, 900 or 1000 to 8000 Daltons, 350, 550, 700, 900 or 1000 to 7000 Daltons, or 350, 550, 700, 900 or 1000 to 6,000 Daltons.

Alternatively put, the alginate oligomer may have a degree of polymerisation (DP), or a number average degree of polymerisation (DPn) of 2 to 100, preferably 2 to 75, preferably 2 to 50, more preferably 2 to 40, 2 to 35, 2 to 30, 2 to 28, 2 to 25, 2 to 22, 2 to 20, 2 to 18, 2 to 17, 2 to 15 or 2 to 12.

Other representative ranges (whether for the number of residues, DP or DPn) include any one of 3, 4, 5, 6, 7, 8, 9, 10 or 11 to any one of 50, 45, 40, 39, 38, 37, 36, 35, 34, 33, 32, 31, 30, 29, 28, 27, 26, 25, 24, 23, 22, 21, 20, 19, 18, 17, 16, 15, 14, 13 or 12.

Other representative ranges (whether for the number of residues, DP or DPn) include anyone of 8, 9, 10, 11, 12, 13, 14 or 15 to any one of 50, 45, 40, 39, 38, 37, 36, 35, 34, 33, 32, 31, 30, 29, 28, 27, 26, 25, 24, 23, 22, 21, 20, 19, 18, 17 or 16.

Other representative ranges (whether for the number of residues, DP or DPn) include any one of 11, 12, 13, 14, 15, 16, 17 or 18 to any one of 50, 45, 40, 39, 38, 37, 36, 35, 34, 33, 32, 31, 30, 29, 28, 27, 26, 25, 24, 23, 22, 21, 20 or 19.

The alginate oligomer of use in the invention is preferably a 3- to 35-mer, more preferably a 3- to 28-mer, in particular a 4- to 25-mer, e.g. a 5- to 20-mer, especially a 6- to 22-mer, in particular an 8- to 20-mer, especially a 10- to 15-mer, e.g. having a molecular weight in the range 350 to 6400 Daltons or 350 to 6000 Daltons, preferably 550 to 5500 Daltons, preferably 750 to 5000 Daltons, and especially 750 to 4500 Daltons or 2000 to 3000 Daltons or 900 to 3500 Daltons. Other representative alginate oligomers include, as mentioned above, oligomers with 5, 6, 7, 8, 9, 10, 11, 12 or 13 to 50, 45, 40, 35, 28, 25, 22 or 20 residues.

The alginate oligomer of the invention may have a degree of polymerisation (DP), or a number average degree of polymerisation (DPn), of 3-28, 4-25, 6-22, 8-20 or 10-15, or 5-18 or 7-15 or 8-12, especially 10.

The alginate oligomer of the invention may have a degree of polymerisation (DP), or a number average degree of polymerisation (DPn), of 3-24, 4-23, 5-22, 6-21, 7-20, 8-19, 9-18, 10-17, 11-16, 12-15 or 13-14 (e.g. 13 or 14).

The alginate oligomer of the invention may have a degree of polymerisation (DP), or a number average degree of polymerisation (DPn), of 4-25, 5-24, 6-23, 7-22, 8-21, 9-20, 10-19, 11-18, 12-17, 13-16, 14-15 (e.g. 14 or 15).

The alginate oligomer of the invention may have a degree of polymerisation (DP), or a number average degree of polymerisation (DPn), of 5-26, 6-25, 7-24, 8-23, 9-22, 10-21, 11-20, 12-19, 13-18, 14-17 or 15-16 (e.g. 15 or 16).

The alginate oligomer of the invention may have a degree of polymerisation (DP), or a number average degree of polymerisation (DPn), of 4-50, 4-40, 4-35, 4-30, 4-28, 4-26, 4-22, 4-20, 4-18, 4-16 or 4-14.

The alginate oligomer of the invention may have a degree of polymerisation (DP), or a number average degree of polymerisation (DPn), of 5-50, 5-40, 5-25, 5-22, 5-20, 5-18, 5-23, 5-20, 5-18, 5-16 or 5-14.

The alginate oligomer of the invention may have a degree of polymerisation (DP), or a number average degree of polymerisation (DPn), of 6-50, 6-40, 6-35, 6-30, 6-28, 6-26, 6-24, 6-20, 6-19, 6-18, 6-16 or 6-14.

The alginate oligomer of the invention may have a degree of polymerisation (DP), or a number average degree of polymerisation (DPn), of 8-50, 8-40, 8-35, 8-30, 8-28, 8-25, 8-22, 8-20, 8-18, 8-16 or 8-14.

The alginate oligomer of the invention may have a degree of polymerisation (DP), or a number average degree of polymerisation (DPn), of 9-50, 9-40, 9-35, 9-30, 9-28, 9-25, 9-22, 9-20, 9-18, 9-16 or 9-14.

The alginate oligomer of the invention may have a degree of polymerisation (DP), or a number average degree of polymerisation (DPn), of 10-50, 10-40, 10-35, 10-30, 10-28, 10-25, 10-22, 10-20, 10-18, 10-16 or 10-14.

The alginate oligomer of the invention may have a degree of polymerisation (DP), or a number average degree of polymerisation (DPn), of 11-50, 11-40, 11-35, 11-30, 11-28, 11-25, 11-22, 11-20, 11-18, 11-16 or 11-14.

The alginate oligomer of the invention may have a degree of polymerisation (DP), or a number average degree of polymerisation (DPn), of 12-50, 12-40, 12-35, 12-30, 12-28, 12-25, 12-22, 12-20, 12-18, 12-16 or 12-14.

The alginate oligomer of the invention may have a degree of polymerisation (DP), or a number average degree of polymerisation (DPn), of 13-50, 13-40, 13-35, 13-30, 13-28, 13-25, 13-22, 13-20, 13-18, 13-16 or 13-14.

The alginate oligomer of the invention may have a degree of polymerisation (DP), or a number average degree of polymerisation (DPn), of 14-50, 14-40, 14-35, 14-30, 14-28, 14-25, 14-22, 14-20, 14-18, 14-16 or 14-15.

The alginate oligomer of the invention may have a degree of polymerisation (DP), or a number average degree of polymerisation (DPn), of 15-50, 15-40, 15-35, 15-30, 15-28, 15-25, 15-22, 15-20, 15-18 or 15-16.

The alginate oligomer of the invention may have a degree of polymerisation (DP), or a number average degree of polymerisation (DPn), of 18-50, 18-40, 18-35, 18-30, 18-28, 18-25, 18-22 or 18-20.

The alginate oligomer is preferably a linear oligomer. It may be a single compound or it may be a mixture of compounds, e.g. of a range of degrees of polymerization. Preferably the alginate oligomer of the invention is substantially free, preferably essentially free, of alginate oligomers having a degree of polymerisation outside of the ranges disclosed herein. This may be expressed in terms of the molecular weight distribution of the alginate oligomer of the invention, e.g. the percentage of each mole of the alginate oligomer being used in accordance with the invention which has a DP outside the relevant range. The molecular weight distribution is preferably such that no more than 10%, preferably no more than 9, 8, 7, 6, 5, 4, 3, 2, or 1% mole has a DP of three, two or one higher than the relevant upper limit for DPn. Likewise it is preferred that no more than 10%, preferably no more than 9, 8, 7, 6, 5, 4, 3, 2, or 1% mole has a DP below a number three, two or one smaller than the relevant lower limit for DPn.

An alginate oligomer will, as noted above, contain (or comprise) guluronate or guluronic acid (G) and/or mannuronate or mannuronic acid (M) residues or units. An alginate oligomer according to the invention will preferably be composed solely, or substantially solely (i.e. consist essentially of) uronate/uronic acid residues, more particularly solely or substantially solely of G and/or M residues. Alternatively expressed, in the alginate oligomer of use in the present invention, at least 80%, more particularly at least 85, 90, 95 or 99% of the monomer residues may be uronate/uronic acid residues, or, more particularly G and/or M residues. In other words, preferably the alginate oligomer will not comprise other residues or units (e.g. other saccharide residues, or more particularly other uronic acid/uronate residues).

As noted above, the monomeric residues in the alginate oligomer, may be the same or different and not all need carry electrically charged groups although it is preferred that the majority (e.g. at least 60%, preferably at least 80% more preferably at least 90%) do. It is preferred that a substantial majority, e.g. at least 80%, more preferably at least 90% of the charged groups have the same polarity. In the alginate oligomer, the ratio of hydroxyl groups to charged groups is preferably at least 2:1, more especially at least 3:1.

In accordance with the invention at least 70% of the monomer residues of the alginate oligomer are M residues (i.e. mannuronate or mannuronic acid). In other words the alginate oligomer will contain at least or alternatively more than 70% mannuronate (or mannuronic acid) residues. Specific embodiments thus include alginate oligomers with (e.g. containing) 70 to 100% M (mannuronate) residues. Further specific embodiments also include oligomers containing 71 to 85% M residues or 85 to 100% M residues. Thus, a representative alginate oligomer for use according to this embodiment of the present invention will contain more than 70% M residues (i.e. more than 70% of the monomer residues of the alginate oligomer will be M residues).

In other embodiments at least or 75, 80, 85, 90, 95 or 99% of the monomer residues are mannuronate. In one embodiment the alginate oligomer may be an oligomannuronate (i.e. a homooligomer of M, or 100% M).

In a further embodiment, the above described alginates of the invention have a primary structure wherein the majority of the M residues are in so called M-blocks. In this embodiment preferably at least 50%, more preferably at least 70 or 75%, and most preferably at least 80, 85, 90 or 95% of the M residues are in M-blocks. An M block is a contiguous sequence of at least two M residues, preferably at least 3 contiguous M residues, more preferably at least 4 or 5 contiguous M residues, most preferably at least 7 contiguous M residues.

In particular, at least 80%, e.g. at least 85% or 90% of the M residues are linked 1-4 to another M residue. More particularly at least 95%, more preferably at least 98%, and most preferably at least 99% of the M residues of the alginate are linked 1-4 to another M residue.

Other preferred oligomers are alginate oligomers wherein at least 70% of the monomer residues in the oligomer are M residues linked 1-4 to another M-residue, or more preferably at least 75%, and most preferably at least 80, 85, 90, 92, 93, 94, 95, 96, 97, 98, 99% of the monomers residues of the oligomer are M residues linked 1-4 to another M residue. This 1-4 linkage of two M residues can be alternatively expressed as a mannuronic unit bound to an adjacent mannuronic unit.

In a still further embodiment, the alginate oligomers of the invention comprise a sequence of alternating M and G residues. A sequence of at least three, preferably at least four, alternating M and G residues represents an MG block. In other words, the alginate oligomers of the invention comprise an MG block. Expressed more specifically, an MG block is a sequence of at least three contiguous residues consisting of G and M residues and wherein each non-terminal (internal) G residue in the contiguous sequence is linked 1-4 and 4-1 to an M residue and each non-terminal (internal) M residue in the contiguous sequence is linked 1-4 and 4-1 to a G residue. Preferably the MG block is at least 5 or 6 contiguous residues, more preferably at least 7 or 8 contiguous residues.

In a further embodiment any G residues in the alginate oligomer are found predominantly in MG blocks. In this embodiment preferably at least 50%, more preferably at least 70 or 75% and most preferably at least 80, 85, 90 or 95% of the guluronate monomers in the alginate oligomer are present in MG blocks. In another embodiment the alginate oligomer is arranged such that at least 50%, at least 60%, at least 70%, at least 80%, at least 85%, at least 90%, at least 95%, at least 99%, e.g. 100% of the G residues in the oligomer are arranged in MG blocks.

In certain embodiments the terminal uronic acid residues of the oligomers of the invention do not have a double bond, especially a double bond situated between the $C_4$ and $C_5$ atom. Such oligomers may be described as having saturated terminal uronic acid residues. The skilled man would be able to prepare oligomers with saturated terminal uronic acid residues without undue burden. This may be through the use of production techniques which yield such oligomers, or by converting (saturating) oligomers produced by processes that yield oligomers with unsaturated terminal uronic acid residues.

The alginate oligomer will typically carry a charge and so counter ions for the alginate oligomer may be any physiologically tolerable ion, especially those commonly used for charged drug substances, e.g. sodium, potassium, ammonium, chloride, mesylate, meglumine, etc. Ions which promote alginate gelation e.g. group 2 metal ions may also be used.

While the alginate oligomer may be a synthetic material generated from the polymerisation of appropriate numbers of guluronate and mannuronate residues, the alginate oligomers of use in the invention may conveniently be obtained, produced or derived from natural sources such as those mentioned above, namely natural alginate source materials.

Polysaccharide to oligosaccharide cleavage to produce the alginate oligomer useable according to the present invention may be performed using conventional polysaccharide lysis techniques such as enzymatic digestion and acid hydrolysis. In one favoured embodiment acid hydrolysis is used to prepare the alginate oligomers on the invention. In other embodiments enzymatic digestion is used with an additional processing step(s) to saturate the terminal uronic acids in the oligomers.

Oligomers may then be separated from the polysaccharide breakdown products chromatographically using an ion exchange resin or by fractionated precipitation or solubilisation or filtration. U.S. Pat. No. 6,121,441 and WO2008/125828, which are explicitly incorporated by reference herein in their entirety, describe a process suitable for preparing the alginate oligomers of use in the invention. Further information and discussion can be found in for example in "Handbooks of Hydrocolloids", Ed. Phillips and Williams, CRC, Boca Raton, Florida, USA, 2000, which textbook is explicitly incorporated by reference herein in its entirety.

The alginate oligomers may also be chemically modified, including but not limited to modification to add charged groups (such as carboxylated or carboxymethylated glycans) and alginate oligomers modified to alter flexibility (e.g. by periodate oxidation).

Alginate oligomers (for example oligoguluronic acids) suitable for use according to the invention may conveniently be produced by acid hydrolysis of alginic acid from, but not limited to, *Laminaria* hyperbora and *Lessonia nigrescens*, dissolution at neutral pH, addition of mineral acid reduce the pH to 3.4 to precipitate the alginate oligomer (oligoguluronic acid), washing with weak acid, resuspension at neutral pH and freeze drying.

The alginates for production of alginate oligomers of the invention can also be obtained directly from suitable bacterial sources e.g. *Pseudomonas aeruginosa* or *Azotobacter vinelandii.*

The molecular apparatus involved in alginate biosynthesis in *Pseudomonas fluorescens* and *Azotobacter vinelandii* has been cloned and characterised (WO 94/09124; Ertesvåg, H., et al, Metabolic Engineering, 1999, Vol 1, 262-269; WO 2004/011628; Gimmestad, M., et al (supra); Remminghorst and Rehm, Biotechnology Letters, 2006, Vol 28, 1701-1712; Gimmestad, M. et al, Journal of Bacteriology, 2006, Vol 188(15), 5551-5560) and alginates of tailored primary structures can be readily obtained by manipulating these systems.

The G content of alginates (for example an algal source material) can be increased by epimerisation, for example with mannuronan C-5 epimerases from *A. vinelandii* or other epimerase enzymes. Thus, for example in vitro epimerisation may be carried out with isolated epimerases from *Pseudomonas* or *Azotobacter*, e.g. AlgG from *Pseudomonas fluorescens* or *Azotobacter vinelandii* or the AlgE enzymes (AlgE1 to AlgE7) from *Azotobacter vinelandii*. The use of epimerases from other organisms that have the capability of producing alginate, particularly algae, is also specifically contemplated. The in vitro epimerisation of low G alginates with *Azotobacter vinelandii* AgE epimerases is described in detail in Ertesvag et al (supra) and Strugala et al (Gums and Stabilisers for the Food Industry, 2004, 12, The Royal Society of Chemistry, 84-94).

To obtain G-block containing alginates or alginate oligomers, epimerisation with one or more *Azotobacter vinelandii* AlgE epimerases other than AlgE4 is preferred as these enzymes are capable of producing G block structures. On the other hand AlgE4 epimerase can be used to create alginates or alginate oligomers with alternating stretches of M/G sequence or primary structures containing single G residue as it has been found that this enzyme seems preferentially to epimerise individual M residues so as to produce single G residues linked to M residues rather than producing G blocks. Particular primary structures can be obtained by using different combinations of these enzymes.

Mutated versions of these enzymes or homologues from other organisms are also specifically contemplated as of use. WO 94/09124 describes recombinant or modified mannuronan C-5 epimerase enzymes (AgE enzymes) for example encoded by epimerase sequences in which the DNA sequences encoding the different domains or modules of the epimerases have been shuffled or deleted and recombined. Alternatively, mutants of naturally occurring epimerase enzymes, (AlgG or AgE) may be used, obtained for example by site directed or random mutagenesis of the AlgG or AlgE genes.

A different approach is to create *Pseudomonas* and *Azotobacter* organisms that are mutated in some or all of their epimerase genes in such a way that those mutants produce alginates of the required structure for subsequent alginate oligomer production, or even alginate oligomers of the required structure and size (or molecular weight). The generation of a number of *Pseudomonas fluorescens* organisms with mutated AlgG genes is described in detail in WO 2004/011628 and Gimmestad, M., et al, 2003 (supra). The generation of a number of *Azotobacter vinelandii* organisms with mutated AgE genes is disclosed in Gimmestad, M., et al, 2006 (supra).

A further approach is to delete or inactivate the endogenous epimerase genes from an *Azotobacteror* a *Pseudomonas* organism and then to introduce one or more exogenous epimerase genes, which may or may not be mutated (i.e. may be wild-type or modified) and the expression of which may be controlled, for example by the use of inducible or other "controllable promoters". By selecting appropriate combinations of genes, alginates of predetermined primary structure can be produced.

A still further approach would be to introduce some or all of the alginate biosynthesis machinery of *Pseudomonas* and/or *Azotobacter* into a non-alginate producing organism (e.g. *E. coli*) and to induce the production of alginate from these genetically modified organisms.

When these culture-based systems are used, the primary structure of the alginate or alginate oligomer products can be influenced by the culture conditions. It is well within the capabilities of the skilled man to adjust culture parameters such as temperature, osmolarity, nutrient levels/sources and atmospheric parameters in order to manipulate the primary structure of the alginates produced by a particular organism.

References to "G residues/G" and "M residues/M" or to guluronic acid or mannuronic acid, or guluronate or mannuronate are to be read interchangeably as references to guluronic acid/guluronate and mannuronic acid/mannuronate (specifically α-L-guluronic acid/guluronate and β-D-mannuronic acid/mannuronate), and further include derivatives thereof in which one or more available side chains or groups have been modified without resulting in a capacity to enhance the translocation of a cationic micro/nanoparticle or a micro/nanoparticle formed of self-assembling micro/nanoparticle forming components, wherein at least one self-assembling micro/nanoparticle forming component is a cationic micro/nanoparticle forming component, across a mucus layer that is substantially lower than that of the unmodified oligomer. Common saccharide modifying groups would include acetyl, sulphate, amino, deoxy, alcohol, aldehyde, ketone, ester and anhydro groups. The alginate oligomers may also be chemically modified to add charged groups (such as carboxylated or carboxymethylated glycans), and to alter flexibility (e.g. by periodate oxidation). The skilled person would be aware of still further chemical modifications that can be made to the monosaccharide subunits of oligosaccharides and these can be applied to the alginate oligomers of the invention.

The invention encompasses the use of a single alginate oligomer or a mixture (multiplicity/plurality) of different alginate oligomers. Thus, for example, a combination of different alginate oligomers (e.g. two or more) may be used.

In more specific embodiments the invention provides a method for treating or preventing a disease or condition or complication thereof which is responsive to, or which is prevented by, a therapeutically active molecule when administered to a mucosal surface, said method comprising (a) administering to a mucus layer of a mucosal surface of a subject, which has, is suspected of having, or is at risk of said disease or condition or complication thereof, a cationic micro/nanoparticle comprising said therapeutically active molecule together with an alginate oligomer having at least 70% mannuronate residues; or (b)(i) contacting a cationic micro/nanoparticle comprising said therapeutically active molecule with at least one alginate oligomer having at least 70% mannuronate residues thereby forming a micro/nanoparticle carrying said alginate oligomer, and (b)(ii) administering the micro/nanoparticle formed in step (b)(i) to a mucus layer of a mucosal surface of a subject, which has, is suspected of having, or is at risk of said disease or condition or complication thereof.

The invention still further embodiments, the invention provides a method for treating or preventing a disease or condition or complication thereof which is responsive to, or which is prevented by, a therapeutically active molecule when administered to a mucosal surface, said method comprising contacting a mucus layer of a mucosal surface of a subject, which has, is suspected of having, or is at risk of said disease or condition or complication thereof, with a micro/nanoparticle which is (i) formed of self-assembling micro/nanoparticle forming components, wherein at least one is a cationic micro/nanoparticle forming component and at least one is an alginate oligomer which has at least 70% mannuronate residues, and (ii) further comprises said therapeutically active molecule, optionally wherein the therapeutically active molecule is covalently bound to one or more of the self-assembling micro/nanoparticle forming components.

The invention further provides an alginate oligomer, wherein said alginate oligomer has at least 70% mannuronate residues, for use in a method for treating or preventing a disease or condition or complication thereof which is responsive to, or which is prevented by, a therapeutically active molecule when administered to a mucosal surface, said method comprising (a) administering to a mucus layer of a mucosal surface of a subject, which has, is suspected of having, or is at risk of said disease or condition or complication thereof, a cationic micro/nanoparticle comprising said therapeutically active molecule together with an alginate oligomer having at least 70% mannuronate residues; or (b)(i) contacting a cationic micro/nanoparticle comprising said therapeutically active molecule with at least one alginate oligomer having at least 70% mannuronate residues thereby forming a micro/nanoparticle carrying said alginate oligomer, and (b)(ii) administering the micro/nanoparticle formed in step (b)(i) to a mucus layer of a mucosal surface of a subject, which has, is suspected of having, or is at risk of said disease or condition or complication thereof.

The invention further provides an alginate oligomer, wherein said alginate oligomer has at least 70% mannuronate residues, for use in a method for treating or preventing a disease or condition or complication thereof which is responsive to, or which is prevented by, a therapeutically active molecule when administered to a mucosal surface, said method comprising (a) preparing a micro/nanoparticle formed of self-assembling micro/nanoparticle forming components, wherein at least one self-assembling micro/nanoparticle forming component is a cationic micro/nanoparticle forming component and at least one is said alginate oligomer, said micro/nanoparticle further comprising the therapeutically active molecule, optionally wherein the therapeutically active molecule is covalently bound to one or more of the self-assembling micro/nanoparticle forming components and (b) administering to a mucus layer of a mucosal surface of a subject, which has, is suspected of having, or is at risk of said disease or condition or complication thereof, with a micro/nanoparticle prepared in step (a).

The invention still further provides the use of an alginate oligomer, wherein said alginate oligomer has at least 70% mannuronate residues, in the manufacture of a medicament for use in the above described methods. In certain embodiments, the medicament may be a micro/nanoparticle carrying an alginate oligomer or a micro/nanoparticle formed of self-assembling micro/nanoparticle forming compounds described herein.

The invention still further provides the use of a cationic micro/nanoparticle comprising a therapeutically active molecule in the manufacture of a medicament for use in the above described methods. In certain embodiments, the medicament may be a micro/nanoparticle carrying an alginate oligomer or a micro/nanoparticle formed of self-assembling micro/nanoparticle forming compounds described herein.

The above described features relating to the use of an alginate oligomer, wherein said alginate oligomer has at least 70% mannuronate residues, and/or a therapeutic cationic micro/nanoparticle in the manufacture of medicaments for use in the methods of the invention presented in the context of more general embodiments of the invention above, in particular those concerning combination products, apply mutatis mutandis to the more specific embodiments of the invention described immediately above and thus all combinations of features and principles described in that section may be applied here with appropriate adaptation where necessary.

The therapeutically active molecule may be referred to as a pharmaceutical or a drug and may, for instance, be any of the therapeutic molecules of interest described herein.

As used herein the term "condition" includes any deleterious physiological disorder which may be experienced by a subject, whether arising due to a genetic defect or mutation, or in any other way, including an acquired condition, e.g. due to environmental and/or pathogen exposure.

The disease or condition may, for instance, be a respiratory disease or condition, an infection, a hyperproliferative or neoplastic disease, an autoimmune disease or an inflammatory bowel disease.

The respiratory disease or condition may be an obstructive respiratory disorder, more particularly a respiratory condition which may be characterised by a chronic inflammatory state, airway remodelling and/or exacerbations due to respiratory tract infections. Such disorders may include COPD (and its subtypes chronic bronchitis and emphysema), bronchiectasis, idiopathic pulmonary fibrosis, primary cillary dyskinesia, pneumonia, asthma, and chronic sinusitis. Such disorders may also include a condition arising from or associated with CFTR dysfunction, e.g. cystic fibrosis, non-compound CFTR gene mutation heterozygosity, abnormal mucus clearance in the respiratory tract and/or breathing difficulties resulting from chronic particulate inhalation, and/or a chronic inflammatory respiratory disorder, e.g. COPD (and its subtypes chronic bronchitis and emphysema), bronchiectasis, asthma and/or chronic sinusitis. Such disorders may also include mucus stasis and breathing difficulties in tobacco smokers and other subjects exposed to the chronic inhalation of particulate irritants, e.g. smoke particles (tobacco, wood etc.), pollution, dust (asbestos, cotton, coal, stone, animal droppings etc.) and spores. In other embodiments the condition may be a mucus-related complication of the above-listed conditions.

COPD, also referred to as chronic obstructive lung disease (COLD) and chronic obstructive airway disease (COAD), is a collective term for chronic obstructive lung diseases characterised by chronic inflammation of the airways without dilation, chronically poor airflow and enhanced sputum production. It is generally accepted that the conditions of chronic bronchitis (inflammation of the mucous membranes of the bronchi) and emphysema (breakdown of the lung tissue, specifically the alveoli) are subtypes of COPD. COPD is usually diagnosed as chronically poor lung function that is not improved by administration of bronchodilators and a chronic productive cough. Imaging of the chest, e.g. with MRI and high resolution computerised tomography (HRCT) may also reveal physiologies characteristic of COPD and to rule out other respiratory conditions.

The enhanced sputum production observed in COPD and its similar characteristics to CF mucus mean the respiratory complications observed in CF as discussed below are common in COPD patients, in particular the complications linked to infection of the airways.

Bronchiectasis is a disease characterised by chronic enlargement and subsequent breakdown of the bronchi as a result of an inflammatory response, chronically poor lung function that may improve by administration of bronchodilators and a chronic productive cough. Diagnosis is usually based on lung function tests and imaging of the chest, e.g. with MRI and high resolution computerised tomography (HRCT) to reveal the enlarged bronchi characteristic of the disease.

The enhanced sputum production observed in bronchiectasis and its similar characteristics to CF mucus mean the respiratory complications observed in CF as discussed above are common in bronchiectasis patients, in particular the complications linked to infection of the airways.

Idiopathic pulmonary fibrosis is characterised by a progressive and irreversible decline in lung function. Complications include heart failure, pulmonary hypertension, pneumonia and pulmonary embolism. The chronic inflammatory processes and tissue remodelling of the airways associated with idiopathic pulmonary fibrosis mean the respiratory complications observed in CF as discussed below may be seen in subject with idiopathic pulmonary fibrosis.

Chronic sinusitis is the long term, more than three months, inflammation of the paranasal sinuses. The cause of that inflammation may be infection, allergy (usually to particulates including dust, pollution, pollen, spores and microorganisms) or an autoimmune response. The inflammation leads to increased mucus production and impaired sinus drainage and secondary bacterial infections, which further contribute to the inflammatory response. That the sinus mucus of a patient with chronic sinusitis has similar characteristics to CF mucus means the respiratory, and especially the paranasal sinus, complications observed in CF as discussed above are common in patients with chronic sinusitis. A diagnosis of chronic sinusitis is usually confirmed with nasal endoscopy.

The sinus mucus of a patient with chronic sinusitis has similar characteristics to CF mucus and this means the respiratory, and especially the paranasal sinus, complications observed in CF as discussed below are common in patients with chronic sinusitis, in particular the complications linked to infection of the airways.

Asthma is a chronic airway disease that manifests as acute episodes of air flow obstruction due to transient bronchoconstriction resulting from the tightening of smooth muscle surrounding the airways, predominantly the bronchioles. Such exacerbations are often triggered by exposure to external stimuli. Bronchial inflammation also leads to tissue swelling and oedema thus causing further obstruction. Underlying the overt episodes of bronchoconstriction and airway obstruction are chronic symptoms of airway thickening and remodelling due to scarring and inflammation and overdeveloped mucus glands.

The chronic inflammatory processes and tissue remodelling of the airways associated with asthma long term, including enhanced sputum production, mean the respiratory complications observed in CF as discussed below may be seen in asthma patients, in particular the complications linked to infection of the airways.

Cystic fibrosis is a human disease characterised by mucus and/or exocrine secretions from the lung, pancreas and liver that have abnormal physical properties, typically increased viscosity and, in the case of mucus, adherence to the epithelium of the mucosal surface. These underlying factors manifest in, amongst other conditions, breathing difficulties, respiratory tract infections (chronic and acute, e.g. of the bronchi or of the lungs), respiratory tract inflammation (e.g. bronchial inflammation (termed bronchitis, if due to infection) or pulmonary inflammation/pneumonitis (termed pneumonia, if due to infection)), pulmonary hypertension, heart failure, respiratory failure, lung remodelling, sinus infection, sinusitis (acute, subacute and chronic), facial pain, headaches, abnormal nasal drainage, thickened faeces, constipation, bowel obstruction, nutrient malabsorption, pancreatic inflammation, pancreatitis, diabetes, gallstones, liver cirrhosis, and infertility. Decreased response to antibiotics, especially in the lungs, is also seen. The abnormal mucus and exocrine secretions arise from mutations in CFTR which affect the ability of this protein to transport chloride and bicarbonate ions across epithelial membranes and thereby regulate the balance of other ions such as sodium. Many such mutations of CFTR have been identified, some resulting in a more pronounced CF phenotype than others. A subject can therefore be considered to be suffering from CF if the subject has one or more, preferably 2, 3, 4, 5, 6 or more or all of the above mentioned conditions, abnormal mucus (e.g. dense, intractable mucus which, in some instances may be attached to epithelium at at least one mucosal surface), hyperviscous sputum or other secretions and/or exocrine secretions and a mutation in each of his/her CFTR genes.

Conveniently CF may be diagnosed by the "sweat test". This is a routine test familiar to the person skilled in the art. Briefly, pilocarpine is placed on the skin and uptake induced by electric current. Sweat released at the treatment site in response to the pilocarpine is collected (e.g. absorbed onto a piece of filter paper) and is then analysed for its salt content. A person with CF will have salt concentrations that are one-and-one-half to two times greater than normal. More specifically, for infants up to and including 6 months of age, a chloride level of equal to or less than 29 mmol/L means CF is very unlikely; levels of 30-59 mmol/L mean that CF is possible; and levels greater than or equal to 60 mmol/L mean CF is likely. For people older than 6 months of age, a chloride level of equal to or less than 39 mmol/L means CF is very unlikely; levels of 40-59 mmol/L mean that CF is possible; and levels greater than or equal to 60 mmol/L mean CF is likely.

In accordance with the invention an infant subject (6 months old or younger) to which the treatment of the invention will be applied will have a sweat chloride level of greater than 25 mmol/L, preferably greater than 29 mmol/L, 35 mmol/L, 40 mmol/L, 45 mmol/L, 50 mmol/L, 55 mmol/L or 60 mmol/L and all other patients will have a sweat chloride level of greater than 35 mmol/L, preferably greater than 39 mmol/L, 45 mmol/L, 50 mmol/L, 55 mmol/L or 60 mmol/L.

CFTR dysfunction has been recognised as being an underlying factor in conditions other than CF. Such dysfunction may be inherited through the inheritance of one mutated CFTR allele or may be acquired through, for example, chronic inhalation of particulates (in particular tobacco and wood smoke) and the chronic inflammation of the respiratory tract (e.g. in COPD and its subtypes CB and emphysema, bronchiectasis and chronic sinusitis).

Non-compound CFTR gene mutation heterozygosity is a clinical condition in which a subject has one CFTR allele that does not carry a mutation which effects the intracellular processing and/or cell surface ion channel activity of the protein expressed therefrom and one allele that does have a mutation that is detrimental to the intracellular processing and/or cell surface ion channel activity of the protein expressed therefrom. Such subjects do not display overt CF as defined above in so far as several of the various complications of CF are clearly seen at any one time, but heterozygous subjects will have, at least at times, a mild form of the abnormal mucus which characterises CF and so may present with mild forms of one or of the complications of CF without being sufficient severe as prompting a clear diagnosis of CF. Specifically subjects with CFTR heterozygosity have been observed as having recurrent "idiopathic" pancreatitis, congenital bilateral absence of the vas deferens, chronic sinusitis, and idiopathic bronchiectasis, but such patients may present with any of the CF complications described herein.

The CF sweat test can be used to identify patients with suspected non-compound CFTR gene mutation heterozygosity as such patients will fall between the "very unlikely" and "likely" ranges of sweat chloride levels. For an infant patient (6 months old or younger) this may be a sweat chloride level of greater than 25 mmol/L, preferably greater than 29 mmol/L, 35 mmol/L, 40 mmol/L, 45 mmol/L, 50 mmol/L, 55 mmol/L, but less than 60 mmol/L and all other patients will have a sweat chloride level of greater than 35 mmol/L, preferably greater than 39 mmol/L, 45 mmol/L, 50 mmol/L, 55 mmol/L, but less than 60 mmol/L. Genetic testing of suspected patients can then confirm the diagnosis.

CFTR dysfunction can also be assessed directly by performing intestinal current measurements (ICM) on rectal biopsies or nasal potential difference (NPD) measurements in vivo, as described in the literature (e.g. De Boeck, K., et al, Journal or Cystic Fibrosis, 2011, Vol 10 (Suppl 2), S53-S66). Comparison of the results from test subjects to those from normal subject controls provides an indication of CFTR dysfunction. As described more specifically in the Examples, sequential exposure of rectal biopsies to the ion channel modulators indomethacin, amiloride, forskolin/IBMX, genistein, carbachol and histamine allows the isolation of CFTR activity during ICM.

It has also been recognised that inhalation of particulate irritants, e.g. smoke particles (tobacco, wood etc.), pollution, dust (asbestos, cotton, coal, stone, animal droppings etc.) and spores can result in defective CFTR ion channel function (and thereby CFTR dysfunction) through the inhibition of CFTR ion transport activity and/or through promoting the internalisation of CFTR from epithelial cell surfaces. Over prolonged periods of exposure this can lead to the formation of mucus characteristic of CF and thus abnormal mucus clearance and/or breathing difficulties in subjects who do not present with overt symptoms of a chronic inflammatory respiratory disorder. The abnormal mucus clearance (or mucus stasis) seen in such subjects mean the respiratory complications observed in CF as discussed above are common in such subjects, e.g. smokers, in particular the complications linked to infection and inflammation of the airways.

The methods and medical uses of the invention can also be considered to be methods of, or medical uses for, treating the complications (especially the mucus-related complications) of the above described conditions associated with or arising from CFTR dysfunction in an patient with the above described condition, which includes preventing, reducing or delaying the development or onset of further complications of the condition, or reducing the risk of a patient with CFTR dysfunction developing or acquiring further complications of the condition. Specifically, this applies to any of the conditions mentioned or discussed above, e.g. CF, non-compound CFTR gene mutation heterozygosity, abnormal mucus clearance in the respiratory tract and/or breathing difficulties resulting from a chronic particulate inhalation, and/or a chronic inflammatory respiratory disorder, e.g. COPD, CB, emphysema, bronchiectasis, asthma and/or chronic sinusitis.

Such complications may be any of those recited in the following sections. For convenience, in the following such conditions are expressed by reference to CFTR dysfunction-associated conditions, but such terms may be interpreted, where context permits, as a condition (or complication) associated with any of the above-listed conditions, e.g. CF, non-compound CFTR gene mutation heterozygosity, etc. as listed above. Thus, such conditions (complications) may be CFTR dysfunction-associated respiratory tract conditions (e.g. respiratory tract infections, respiratory tract inflammations, breathing difficulties, respiratory failure and lung remodelling), CFTR dysfunction-associated cardiovascular conditions (e.g. pulmonary hypertension and heart failure); CFTR dysfunction-associated paranasal sinus conditions (e.g. paranasal sinus infection, sinusitis facial pain, headaches, abnormal nasal drainage, nasal polyps); CFTR dysfunction-associated GI conditions (e.g. constipation, bowel obstruction (e.g. meconium ileus in neonatal subjects and intussusception and DIOS in older patients), nutrient malabsorption); CFTR dysfunction-associated pancreatic conditions (e.g. pancreatic duct obstruction, nutrient malabsorption, pancreatic inflammation, pancreatitis (acute and chronic), diabetes); CFTR dysfunction-associated hepatic conditions (e.g. bile duct obstruction, gallstones, liver cirrhosis); and CFTR dysfunction-associated infertility.

The present invention is therefore also useful prophylactically, since by combating CFTR dysfunction and restoring a more normal mucus phenotype in a subject with an alginate oligomer and a CFTR modulator, the development of CFTR dysfunction-associated conditions, e.g. infections and/or inflammation (most notably in the respiratory tract, GI tract, pancreas and/or liver) may be avoided (i.e. reduced or prevented).

More generally the invention may be considered to be methods of, or medical uses for, treating the above mentioned CFTR dysfunction-associated conditions. The treatment of CFTR dysfunction-associated pulmonary, GI, pancreatic and hepatic conditions (e.g. those specified above) is preferred.

In the treatment or prevention of the above described respiratory diseases or conditions or complications thereof, the therapeutically active agent may be a CFTR modulator, an antibiotic, an antifungal, an antiviral, an immunostimulatory agent, a corticosteroid, a non-steroidal anti-inflammatory drug (NSAID), a bronchodilator, or an oral antidiabetic drug, e.g. any of those disclosed above, a peptide hormone, a cytokine, a peptide growth factor, a peptide antigen or a nucleic acid for use in the gene therapy, gene editing, RNA interference therapy (e.g. siRNA or miRNA), antisense therapy or in vitro transcribed mRNA (IVT-mRNA) therapy of a genetic mediator of such diseases or conditions. In particular, the nucleic acid may encode a functional CFTR protein.

The disease or condition may be an infection, e.g. a bacterial, fungal or viral infection, in particular an infection of the respiratory system, e.g. the lower respiratory tract (e.g. in the bronchi or in the lungs). The infection may be a chronic infection. Such infections may commonly be caused by *Staphylococcus aureus, Haemophilus influenzae, Pseudomonas aeruginosa, Mycobacterium avium* complex, *Mycobacterium tuberculosis* (the causative agent of pulmonary tuberculosis) and *Aspergillus fumigatus* although the infections/inflammations may be caused by any infectious agent, e.g. by bacteria, fungus, virus and parasites. In addition to those already mentioned, common infectious agents found in the respiratory tract include, but are not limited to, *Chlamydophila pneumonia, Bordetella pertussis, Mycoplasma pneumonia, Moraxella catarrhalis, Legionella pneumophila, Streptococcus pneumonia, Chlamydia psittaci, Coxiella burnetti*, rhinovirus, coronavirus, influenza virus, respiratory syncytial virus (RSV), adenovirus, metapneumovirus, parainfluenza virus, *Histoplasma capsulatum, Cryptococcus neoformans, Pneumocystis jiroveci, Coccidioides immitis, Toxoplasma gondii, Strongyloides stercoralis, Ascaris lumbricoides*, and *Plasmodium malariae.*

In further embodiments the infection may be in the upper respiratory tract e.g. the nose, nasal passages, pharynx, larynx and trachea. The disease or condition may therefore be rhinitis, nasopharyngitis, rhinopharyngitis, pharyngitis, epiglottitis, supraglottitis, laryngitis, laryngotracheitis, tracheitis or tonsillitis. These conditions are sometimes collectively termed upper respiratory tract infections and may be caused by any of the infectious agents mentioned above.

In certain embodiments the infection is in a subject with CFTR dysfunction.

In the treatment or prevention of the above described infections, the therapeutically active agent may be a CFTR modulator, an antibiotic, an antifungal, an antiviral, an immunostimulatory agent, a corticosteroid, a non-steroidal anti-inflammatory drug (NSAID), or a bronchodilator, e.g. any of those disclosed above, a peptide hormone, a cytokine, a peptide growth factor, a peptide antigen or a nucleic acid for use in the gene therapy, gene editing, RNA interference therapy (e.g. siRNA or miRNA), antisense therapy or in vitro transcribed mRNA (IVT-mRNA) therapy of a genetic mediator of such infections. In particular, the nucleic acid may encode a functional CFTR protein.

The hyperproliferative or neoplastic disease or condition may be any disease or condition caused by any malignant, pre-malignant or non-malignant (benign) neoplastic entities. The term therefore encompasses, inter alia, cancers, tumours, malignancies, sarcomas, carcinomas, germinomas, lymphomas, leukaemias, blastomas, papillomas and adenomas. In these various embodiments the hyperproliferative or neoplastic disease or condition may be selected from colorectal cancer (also known as colon cancer, rectal cancer or bowel cancer), prostate cancer, kidney (renal) cancer (e.g. Wilm's tumour), pancreatic cancer, testicular cancer, skin cancer (e.g. melanoma and non-melanoma (e.g. basal-cell cancer, squamous-cell cancer)), breast cancer, ovarian cancer, stomach (gastric) cancer, intestinal cancer (e.g. duodenal cancer, ileal cancer, jejunal cancer, small intestine cancer), liver (hepatic) cancer, lung (pulmonary) cancer, oesophageal cancer, oral cancer, throat cancer, brain cancer (e.g. glioblastoma, medulloblastoma), adrenal cancer (e.g. adrenocortical cancer), thyroid cancer (e.g. anaplastic thyroid carcinoma), uterine cancer (e.g. uterine carcinosarcoma), haematological cancer (also known as the haematological malignancies) (e.g. haematopoietic and lymphoid cancer malignancies, e.g. leukaemia, lymphoma and myeloma), including metastatic forms thereof, and non-malignant neoplasm or tumour in these anatomical sites (e.g. colorectal polyps, pilomatrixoma, hemangioma, osteoma, chondroma, lipoma, fibroma, lymphangioma, leiomyoma, rhabdomyoma, astrocytoma, meningioma, ganglioneuroma, papilloma, adenoma).

In the treatment or prevention of the above described hyperproliferative or neoplastic disease or condition or complication thereof, the therapeutically active agent may be a cytotoxic chemotherapy agent, an angiogenesis inhibitor, an anti-cancer monoclonal antibody, a radioimmunotherapeutic, an immunostimulatory agent, an immunosuppressant, a corticosteroid, or a radiopharmaceutical, e.g. any of those disclosed above, a peptide hormone, a cytokine, a peptide growth factor, a peptide antigen or a nucleic acid for use in the gene therapy, gene editing, RNA interference therapy (e.g. siRNA or miRNA), antisense therapy or in vitro transcribed mRNA (IVT-mRNA) therapy of a genetic mediator of such infections, e.g. an oncogene, a tumour suppressor gene of an angiogenesis factor.

The autoimmune disease may be Addison disease, haemolytic autoimmune anaemia, anti-glomerular basement membrane disease, anti-neutrophil cytoplasmic antibody-associated vasculitis, antiphospholipid syndrome, arthritis, juvenile, rheumatoid arthritis, Felty syndrome, rheumatoid vasculitis, Sjogren's syndrome, Still's disease, anti-n-methyl-d-aspartate receptor encephalitis, Lambert-Eaton myasthenic syndrome, myasthenia gravis, polyradiculoneuropathy, Guillain-Barre syndrome, stiff-person syndrome, uveomeningoencephalitic syndrome, central nervous system vasculitis, autoimmune hypophysitis, autoimmune lymphoproliferative syndrome, dermatitis herpetiformis, diabetes mellitus type 1, glomerulonephritis, Graves' disease, autoimmune hepatitis, linear IgA bullous dermatosis, systemic lupus erythematosus, sympathetic ophthalmia, autoimmune polyendocrinopathies, idiopathic thrombocytopenic purpura, autoimmune thyroiditis, microscopic colitis (collagenous colitis and lymphocytic colitis), diversion colitis or Behcet's disease.

In the treatment or prevention of the above described autoimmune diseases or conditions or complications thereof, the therapeutically active agent may be an immunosuppressant, a corticosteroid, a non-steroidal anti-inflammatory drug (NSAID) or an oral antidiabetic drug, e.g. any of those disclosed above, a cytokine, a growth factor, a peptide hormone, or a nucleic acid for use in the gene therapy, gene editing, RNA interference therapy (e.g. siRNA or miRNA), antisense therapy or in vitro transcribed mRNA (IVT-mRNA) therapy of a genetic mediator of such diseases or conditions.

The inflammatory bowel disease may be ulcerative colitis, Crohn's disease, microscopic colitis (collagenous colitis and lymphocytic colitis), diversion colitis or Behcet's disease.

In the treatment or prevention of the above described inflammatory bowel diseases the therapeutically active agent may be a an antibiotic, an immunostimulatory agent, an immunosuppressant, a corticosteroid, a non-steroidal anti-inflammatory drug (NSAID), e.g. any of those disclosed above, a cytokine, a growth factor, a peptide hormone, or a nucleic acid for use in the gene therapy, gene editing, RNA interference therapy (e.g. siRNA or miRNA), antisense therapy or in vitro transcribed mRNA (IVT-mRNA) therapy of a genetic mediator of such diseases or conditions.

"Treatment" when used generally in relation to the treatment of a disease or medical condition in a subject in accordance with the invention is used broadly herein to include any therapeutic effect, i.e. any beneficial effect in relation to the disease or on the condition. Thus, not only included is eradication or elimination of the disease or condition, or cure of the subject, but also an improvement in the disease or condition of the subject. Thus included for example, is an improvement in any symptom or sign of the disease or condition, or in any clinically accepted indicator of the disease/condition. Treatment thus includes both curative and palliative therapy, e.g. of a pre-existing or diagnosed disease/condition, i.e. a reactionary treatment.

"Prevention" as used generally herein refers to any prophylactic or preventative effect. It thus includes delaying, limiting, reducing or preventing the disease or condition or the onset of the disease or condition, or one or more symptoms or indications thereof, for example relative to the disease or condition or symptom or indication prior to the prophylactic treatment. Prophylaxis thus explicitly includes both absolute prevention of occurrence or development of the disease or condition, or symptom or indication thereof, and any delay in the onset or development of the disease or condition or symptom or indication, or reduction or limitation on the development or progression of the disease condition or symptom or indication.

In the more specific context of conditions or disorders arising from or associated CF and non-compound CFTR gene mutation heterozygosity and their complications, because these diseases are genetic diseases which are characterised in each subject by the unique collection of CF- and non-compound CFTR gene mutation heterozygosity-associated disorders and conditions displayed by the subject at the time of receiving the treatments of the invention, the terms "treatment of CF" and "treatment of non-compound CFTR gene mutation heterozygosity" can be considered to be the treatment of any or all of the disorders and conditions of the subject, or their complications, or the treatment of a subset thereof.

Thus, although certain treatments provided by the invention do not address correction of the underlying genetic defect of CF or non-compound CFTR gene mutation heterozygosity, they do relate to treatment of the effects in the body which arise from the defect, e.g. an alleviation of the effects thereof, e.g. effects arising from the abnormal mucus, and so include the treatment of an associated disorder or condition and also an improvement in the clinical effects of the disorder or condition or overall well-being of the subject.

In this context, a "cure" of CF or non-compound CFTR gene mutation heterozygosity would amount to complete alleviation of the various CF- or non-compound CFTR gene mutation heterozygosity-associated disorders and conditions displayed by the subject at the time of receiving the treatments of the invention; however the genetic basis for the disease (the CFTR mutation) would still remain. Nonetheless, "treatment" in these contexts does not require such a "cure" and as noted above, includes an improvement in any effect which the CF or non-compound CFTR gene mutation heterozygosity has on the body. Thus included, for example, is an improvement in any symptom or sign of a CF- or non-compound CFTR gene mutation heterozygosity-associated disorder or condition, or in any clinically accepted indicator of a CF- or non-compound CFTR gene mutation heterozygosity-associated disorder or condition in the subject (for example, increasing mucociliary clearance in the lungs, reduced incidence of constipation, improvement in nutrient absorption and increased bioavailability of pharmaceuticals and nutritional or digestive enzyme supplements, which in specific embodiments may be seen as increased responsiveness of lung infections to antibiotics and improved digestive health). In these contexts it may be that a pre-existing CF- or non-compound CFTR gene mutation heterozygosity-associated disorder or condition is not fully eradicated or the onset of a new CF- or non-compound CFTR gene mutation heterozygosity-associated disorder or condition is not completely halted, but the treatments are sufficient to inhibit these processes to such an extent that the target CF- or non-compound CFTR gene mutation heterozygosity-associated disorder or condition is fully resolved, or at least resolved to some extent, preferably to an extent acceptable to the subject. Treatment thus includes both curative and palliative therapy, e.g. of a pre-existing or diagnosed CF- or non-compound CFTR gene mutation heterozygosity-associated disorder or condition, i.e. a reactionary treatment.

"Prevention" in the context of CF and non-compound CFTR gene mutation heterozygosity thus relates to preventing an effect in the body which arises as a result of the underlying genetic defect, or as a result of the abnormal mucus. In these contexts, because these diseases are genetic diseases which are characterised in each subject by the unique collection of CF- or non-compound CFTR gene mutation heterozygosity-associated disorders and conditions displayed by the subject at the time of receiving the treatments of the invention, the term "prevention of CF or non-compound CFTR gene mutation heterozygosity or a CF- or non-compound CFTR gene mutation heterozygosity-associated disorder or condition" can be considered to be the prevention of any CF- or non-compound CFTR gene mutation heterozygosity-associated disorder or condition or complication thereof that the subject has yet to acquire or which the subject has acquired previously but has overcome prior to receiving the claimed treatments.

Prophylaxis explicitly includes both absolute prevention of occurrence or development of an effect of a condition arising from or associated with CFTR ion channel dysfunction, as defined above, or symptom or indication thereof, and any delay in the onset or development of an effect of a condition arising from or associated with a CFTR dysfunction, as defined above, or symptom or indication thereof, or reduction or limitation of the development or progression of a condition arising from or associated with CFTR dysfunction, as defined above, or symptom or indication thereof. The preventative treatments can also be considered as treatments that reduce the risk of a patient acquiring or developing a condition arising from or associated with CFTR dysfunction, as defined above, or symptom or indication thereof.

In other embodiments the treatments act at the genetic (nucleic acid) level and so may be able to address correction of the underlying genetic defect of CF or non-compound CFTR gene mutation heterozygosity. In these contexts, "treatment" and "prevention" may be interpreted in line with its more general use as explained above.

The treatment or prevention of other diseases and conditions which have a genetic cause, e.g. neoplastic disease, may be interpreted analogously.

In more specific embodiments the invention provides a method for diagnosing, prognosing or monitoring a disease or condition, the characteristics of which may be determined by a diagnostically effective indicator molecule when administered to a mucosal surface, said method comprising (a) administering to a mucus layer of a mucosal surface of a subject, which has, is suspected of having, or is at risk of said disease or condition or complication thereof, a cationic micro/nanoparticle comprising said diagnostically effective indicator molecule together with an alginate oligomer having at least 70% mannuronate residues; or (b)(i) contacting a cationic micro/nanoparticle comprising said diagnostically effective indicator molecule with at least one alginate oligomer having at least 70% mannuronate residues thereby forming a micro/nanoparticle carrying said alginate oligomer, and (b)(ii) administering the micro/nanoparticle formed in step (b)(i) to a mucus layer of a mucosal surface of a subject, which has, is suspected of having, or is at risk of said disease or condition, and (c) detecting signals, directly or indirectly, from the diagnostically effective indicator molecule which are indicative of a characteristic of the disease or condition, wherein a property of said signals indicates whether or not the subject has said disease or condition, the state of the disease or condition in the subject, the risk the subject has of developing the disease or condition, or the risk of the disease or condition progressing in the subject.

In still further embodiments, the invention provides a method for diagnosing, prognosing or monitoring a disease or condition, the characteristics of which may be determined by a diagnostically effective indicator molecule when administered to a mucosal surface, said method comprising contacting a mucus layer of a mucosal surface of a subject, which has, is suspected of having, or is at risk of said disease or condition, with a micro/nanoparticle which is (i) formed of self-assembling micro/nanoparticle forming components, wherein at least one is a cationic micro/nanoparticle forming component and at least one is an alginate oligomer which has at least 70% mannuronate residues, and (ii) further comprises said diagnostically effective indicator, optionally wherein the diagnostically effective indicator is covalently bound to one or more of the self-assembling micro/nanoparticle forming components, and (iii) detecting signals, directly or indirectly, from the diagnostically effective indicator molecule which are indicative of a characteristic of the disease or condition, wherein a property of said signals indicates whether or not the subject has said disease or condition, the state of the disease or condition in the subject, the risk the subject has of developing the disease or condition, or the risk of the disease or condition progressing in the subject.

The invention further provides an alginate oligomer, wherein said alginate oligomer has at least 70% mannuronate residues, for use in a method for diagnosing, prognosing or monitoring a disease or condition, the characteristics of which may be determined by a diagnostically effective indicator molecule when administered to a mucosal surface, said method comprising (a) administering to a mucus layer of a mucosal surface of a subject, which has, is suspected of having, or is at risk of said disease or condition or complication thereof, a cationic micro/nanoparticle comprising said diagnostically effective indicator molecule together with an alginate oligomer having at least 70% mannuronate residues; or (b)(i) contacting a cationic micro/nanoparticle comprising said diagnostically effective indicator molecule with at least one alginate oligomer having at least 70% mannuronate residues thereby forming a micro/nanoparticle carrying said alginate oligomer, and (b)(ii) administering the micro/nanoparticle formed in step (b)(i) to a mucus layer of a mucosal surface of a subject, which has, is suspected of having, or is at risk of said disease or condition, and (c) detecting signals, directly or indirectly, from the diagnostically effective indicator molecule which are indicative of a characteristic of the disease or condition, wherein a property of said signals indicates whether or not the subject has said disease or condition, the state of the disease or condition in the subject, the risk the subject has of developing the disease or condition, or the risk of the disease or condition progressing in the subject.

The invention further provides an alginate oligomer, wherein said alginate oligomer has at least 70% mannuronate residues, for use in a method for diagnosing, prognosing or monitoring a disease or condition, a characteristic of which may be indicated by a diagnostically effective indicator molecule when administered to a mucosal surface, said method comprising (a) preparing a micro/nanoparticle formed of self-assembling micro/nanoparticle forming components, wherein at least one self-assembling micro/nanoparticle forming component is a cationic micro/nanoparticle forming component and at least one is said alginate oligomer, said micro/nanoparticle further comprising the diagnostically effective indicator, optionally wherein the diagnostically effective indicator is covalently bound to one or more of the self-assembling micro/nanoparticle forming components and (b) administering to a mucus layer of a mucosal surface of a subject, which has, is suspected of having, or is at risk of said disease or condition, with a micro/nanoparticle prepared in step (a), and (c) detecting signals, directly or indirectly, from the diagnostically effective indicator molecule which are indicative of a characteristic of the disease or condition, wherein a property of said signals indicates whether or not the subject has said disease or condition, the state of the disease or condition in the subject, the risk the subject has of developing the disease or condition, or the risk of the disease or condition progressing in the subject.

The invention still further provides the use of an alginate oligomer, wherein said alginate oligomer has at least 70% mannuronate residues, in the manufacture of a medicament for use in the above described methods. In certain embodiments, the medicament may be a micro/nanoparticle carrying an alginate oligomer or a micro/nanoparticle formed of self-assembling micro/nanoparticle forming compounds described herein.

The invention still further provides the use of a cationic micro/nanoparticle comprising a diagnostically effective indicator molecule in the manufacture of a medicament for use in the above described methods. In certain embodiments, the medicament may be a micro/nanoparticle carrying an alginate oligomer or a micro/nanoparticle formed of self-assembling micro/nanoparticle forming compounds described herein.

The above described features relating to the use of an alginate oligomer, wherein said alginate oligomer has at least 70% mannuronate residues, and/or a diagnostic cationic micro/nanoparticle in the manufacture of medicaments for use in the methods of the invention presented in the context of more general embodiments of the invention above, in particular those concerning combination products, apply mutatis mutandis to the more specific embodiments of the invention described immediately above and thus all combinations of features and principles described in that section may be applied here with appropriate adaptation where necessary. The property of the signal detected in accordance with the invention may be its absence or presence, the relative or absolute strength of the signal or a variation in the signal over time.

In these embodiments the methods may comprise a further step in which the subject is diagnosed as having said disease or condition, the state of the disease or condition in the subject is determined, the risk the subject has of developing the disease or condition is determined, the risk of the disease or condition progressing in the subject is determined, or the prognosis for the disease or condition in the subject is determined.

The diagnostically effective molecule (diagnostic agent) may include radiodiagnostics, contrast agents or a nucleic acid or protein for use as a molecular probe (e.g. oligonucleotides and antibodies).

As shown in the Examples, alginate oligomers which have at least 70% mannuronate residues are able to reduce the cytotoxicity of cationic micro/nanoparticles and micro/nanoparticles formed of cationic micro/nanoparticle forming components. Thus, in certain embodiments the methods and uses described herein may be associated with reduced, or less, cytotoxicity as compared to the method or use when performed with an equivalent micro/nanoparticle in the absence of an alginate oligomer which has at least 70% mannuronate residues. In these embodiments the relevant cytotoxicity is that of the cells immediately underlying the mucus layer, or region thereof, contacted with the micro/nanoparticle.

The subject may be any human or non-human animal subject, but more particularly may be a human or non-human vertebrate, e.g. a non-human animal selected from mammals, birds, amphibians, fish and reptiles. The non-human animal may be a livestock or a domestic animal or an animal of commercial value, including laboratory animals or an animal in a zoo or game park. Representative non-human animals therefore include dogs, cats, horses, pigs, sheep, goats, cows, chickens, turkeys, guinea fowl, ducks and geese. Veterinary uses of the invention are thus covered. The subject may be viewed as a patient. In certain embodiments the subject is a human patient with CFTR ion channel dysfunction, more specifically a pathological phenotype, e.g. abnormal mucus and mucus clearance, associated with CFTR dysfunction. In particular embodiments the subject will be a human patient with CF. The terms "subject with CF", subject suffering from CF", "subject having CF" and "CF subject" are considered to be equivalent and are used interchangeably herein. The subject may be of any age, e.g. may be a new-born, an infant, a child, a juvenile, an adolescent or an adult. Expressed differently, the subject is at least 5 years old, e.g. at least 6, 7, 8, 9, 10, 11, 12, 13, 14, 15, 16, 17 or 18 years old. In certain embodiments the subject has a well-established CFTR dysfunction phenotype which includes symptoms of the condition to be treated in accordance with the invention (e.g. one including chronic infection, chronic inflammation and/or airway remodelling). By "well-established" it is meant that the phenotype has been observed in the subject for at least 2 years, e.g. at least 3, 4, 5, 6, 7, 8, 9 or 10 years.

The micro/nanoparticles of use in the invention may be administered to a subject in any convenient form or by any convenient means in order to deliver effective amounts of the micro/nanoparticle to the mucosal surface to be treated. This may be by enteral (e.g. oral, buccal, sublingual, rectal) or topical routes or by inhalation (including nasal inhalation). Administration may achieve systemic distribution or localised distribution, by which it is meant that delivery is effected to the target site or location, but essentially no other location in the patient. The skilled person would be able to select an appropriate administration means to suit any particular target site or location. As discussed above, in certain embodiments the micro/nanoparticles of use in accordance with the invention may be targeted to a target site by a receptor affinity molecule.

The alginate oligomers of use in the invention may be administered to a subject in any convenient form or by any convenient means in order to deliver effective amounts of the alginate oligomer to the mucosal surface to be treated. This may be by parenteral (e.g. intravenous, intraspinal, intramuscular, subcutaneous), enteral (e.g. oral, buccal, sublingual, rectal) or topical routes or by inhalation (including nasal inhalation). Administration may achieve systemic distribution or localised distribution, by which it is meant that delivery is effected to the target site or location, but essentially no other location in the patient. The skilled person would be able to select an appropriate administration means to suit any particular target site or location. Systemic administration, particularly achieved by parenteral administration, may be preferred for convenience.

The skilled person will be able to formulate the micro/nanoparticles and alginate oligomers of use in the invention into pharmaceutical compositions that are adapted for these routes of administration and body distribution according to any of the conventional methods known in the art and widely described in the literature. More specifically, the micro/nanoparticles and alginate oligomers of use in the invention may be incorporated, optionally together with other active agents, with one or more conventional carriers, diluents and/or excipients, to produce conventional galenic preparations such as tablets, pills, granules (e.g. in free form or enclosed in capsules), powders (e.g. inhalable powders), lozenges, sachets, cachets, elixirs, suspensions, emulsions, solutions, syrups, aerosols (as a solid or in a liquid medium), sprays (e.g. nasal sprays), compositions for use in nebulisers, ointments, creams, salves, soft and hard gelatine capsules, suppositories, pessaries, sterile injectable solutions, sterile packaged powders, and the like. Enteric coated solid or liquid compositions, e.g. enteric coated tablets and enteric coated granules (which may be provided in an enteric-coated capsule or in a non-enteric-coated capsule i.e. in which the coating may or may not be an enteric coating); sterile injectable compositions are of particular note.

Examples of suitable carriers, excipients, and diluents are lactose, dextrose, sucrose, sorbitol, mannitol, starches, gum acacia, calcium phosphate, inert alginate polymers, tragacanth, gelatine, calcium silicate, microcrystalline cellulose, polyvinylpyrrolidone, cellulose, water syrup, water, water/ethanol, water/glycol, water/polyethylene, hypertonic salt water, glycol, propylene glycol, methyl cellulose, methylhydroxybenzoates, propyl hydroxybenzoates, talc, magnesium stearate, mineral oil or fatty substances such as hard fat or suitable mixtures thereof. Excipients and diluents of note are mannitol and hypertonic salt water (saline).

The compositions may additionally include lubricating agents, wetting agents, emulsifying agents, suspending agents, preserving agents, sweetening agents, flavouring agents, and the like.

Parenterally administrable forms, e.g. solutions suitable for delivery intravenously, should be sterile and free from physiologically unacceptable agents, and should have low osmolarity to minimize irritation or other adverse effects upon administration and thus solutions should preferably be isotonic or slightly hypertonic, e.g. hypertonic salt water (saline). Suitable vehicles include aqueous vehicles customarily used for administering parenteral solutions such as sterile water for injection, Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405-1412 and 1461-1487 (1975) and The National Formulary XIV, 14th ed. Washington: American Pharmaceutical Association (1975)), which is explicitly incorporated by reference herein in its entirety. The solutions can contain preservatives, antimicrobial agents, buffers and antioxidants conventionally used for parenteral solutions, excipients and other additives which are compatible with the micro/nanoparticles and alginate oligomers of use in the invention and which will not interfere with the manufacture, storage or use of the products.

Simple sterile liquid compositions comprising the micro/nanoparticles and/or alginate oligomers of use in the invention may be especially convenient.

Solid or liquid formulations of the micro/nanoparticles and/or alginate oligomers of use in the invention may be provided with an enteric coating that prevents degradation in the stomach and/or other parts of the upper GI tract but permits degradation in the lower GI tract, e.g. the small intestine. Such coatings are routinely prepared from polymers including fatty acids, waxes, shellac, plastics, and plant fibres. Specific examples thereof include but are not limited to methyl acrylate-methacrylic acid copolymers, methyl methacrylate-methacrylic acid copolymers, cellulose acetate succinate, hydroxypropyl methylcellulose phthalate, hydroxypropyl methylcellulose acetate succinate (hypromellose acetate succinate), polyvinyl acetate phthalate (PVAP), cellulose acetate trimellitate, and sodium alginate polymer. Enteric coated tablets and enteric coated granules (which may be provided in an enteric-coated capsule or in a non-enteric coated capsule) are of particular note. Enteric coated granules may be prepared in accordance with the teachings of WO 1989008448 and A-Khedairy, E. B. H, 2006, Iraqi J. Pharm. Sci., Vol. 15 (1) 49, the contents of which are incorporated herein by reference, although the skilled person would be aware of further alternative techniques which may be used.

For topical administration the micro/nanoparticles and/or alginate oligomers of use in the invention can be incorporated into creams, ointments, gels, salves, and the like. Further topical systems that are envisaged to be suitable are in situ drug delivery systems, for example gels where solid, semi-solid, amorphous or liquid crystalline gel matrices are formed in situ and which may comprise the micro/nanoparticles and/or alginate oligomers of use in the invention. Such matrices can conveniently be designed to control the release of the micro/nanoparticles and/or alginate oligomers from the matrix, e.g. release can be delayed and/or sustained over a chosen period of time. Such systems may form gels only upon contact with mucosal surfaces. Typically the gels are mucoadhesive.

The relative content of the micro/nanoparticles and/or alginate oligomers of use in the invention in the compositions of the invention can vary depending on the dosage required and the dosage regime being followed but will be sufficient to achieve an effective amount at the target treatment site or site, taking account of variables such as the physical size of the subject to be treated, the nature of the subject's particular ailments, and the location and identity of the target treatment area. The skilled person would know that the amounts of the micro/nanoparticles and/or alginate oligomers of use in the invention in the compositions can be reduced if a multiple dose dosing regime is followed or increased to minimise the number of administrations or applications.

A representative aqueous solution for delivery of an alginate oligomer of use in the invention by injection (e.g. by intravenous, intraspinal, intramuscular or subcutaneous injection) will be sterile and may contain 0.1 to 10%, e.g. 0.1 to 5%, 0.1 to 2%, 0.1 to 1%, 0.1 to 0.8%, 0.1 to 0.5%, 0.1 to 0.2%, 0.2 to 10%, 0.2 to 5%, 0.2 to 2%, 0.2 to 1%, 0.2 to 0.8%, 0.2 to 0.5%, 0.5 to 10%, 0.5 to 5%, 0.5 to 2%, 0.5 to 1%, 0.5 to 0.8%, 0.8 to 10%, 0.8 to 5%, 0.8 to 2%, 0.8 to 1%, 1 to 10%, 1 to 5%, 1 to 2%, 2 to 10%, 2 to 5% or 5 to 10%, w/v of the alginate oligomer the remainder being comprised of water and pharmaceutically acceptable excipients and/or other active agents if being used.

A representative inhalable solution to be used to administer a micro/nanoparticle of use in the invention to the respiratory tract typically will be sterile and may contain 0.1 to 10%, e.g. 0.1 to 5%, 0.1 to 2%, 0.1 to 1%, 0.1 to 0.8%, 0.1 to 0.5%, 0.1 to 0.2%, 0.2 to 10%, 0.2 to 5%, 0.2 to 2%, 0.2 to 1%, 0.2 to 0.8%, 0.2 to 0.5%, 0.5 to 10%, 0.5 to 5%, 0.5 to 2%, 0.5 to 1%, 0.5 to 0.8%, 0.8 to 10%, 0.8 to 5%, 0.8 to 2%, 0.8 to 1%, 1 to 10%, 1 to 5%, 1 to 2%, 2 to 10%, 2 to 5% or 5 to 10% w/v of the micro/nanoparticle, the remainder being comprised of pharmaceutically acceptable excipients, e.g. water, and/or other active agents if being used (e.g. an alginate oligomer of use in the invention).

A representative inhalable solution to be used to administer an alginate oligomer of use in the invention to the respiratory tract typically will be sterile and may contain 0.1 to 10%, e.g. 0.1 to 5%, 0.1 to 2%, 0.1 to 1%, 0.1 to 0.8%, 0.1 to 0.5%, 0.1 to 0.2%, 0.2 to 10%, 0.2 to 5%, 0.2 to 2%, 0.2 to 1%, 0.2 to 0.8%, 0.2 to 0.5%, 0.5 to 10%, 0.5 to 5%, 0.5 to 2%, 0.5 to 1%, 0.5 to 0.8%, 0.8 to 10%, 0.8 to 5%, 0.8 to 2%, 0.8 to 1%, 1 to 10%, 1 to 5%, 1 to 2%, 2 to 10%, 2 to 5% or 5 to 10% w/v of the alginate oligomer, the remainder being comprised of pharmaceutically acceptable excipients, e.g. water, and/or other active agents if being used (e.g. an micro/nanoparticle of use in the invention).

For administration of the micro/nanoparticles of use in the invention to the nose or paranasal sinuses a sterile aqueous liquid formulation may be used; administered for instance by a nasal spray device, e.g. propellant-free or propellant-assisted. A representative formulation may contain 0.1 to 10%, e.g. 0.1 to 5%, 0.1 to 2%, 0.1 to 1%, 0.1 to 0.8%, 0.1 to 0.5%, 0.1 to 0.2%, 0.2 to 10%, 0.2 to 5%, 0.2 to 2%, 0.2 to 1%, 0.2 to 0.8%, 0.2 to 0.5%, 0.5 to 10%, 0.5 to 5%, 0.5 to 2%, 0.5 to 1%, 0.5 to 0.8%, 0.8 to 10%, 0.8 to 5%, 0.8 to 2%, 0.8 to 1%, 1 to 10%, 1 to 5%, 1 to 2%, 2 to 10%, 2 to 5% or 5 to 10%, w/v of the micro/nanoparticle, the remainder being comprised of pharmaceutically acceptable excipients, e.g. water, and/or other active agents if being used (e.g. an alginate oligomer of use in the invention).

For administration of an alginate oligomer of use in the invention to the nose or paranasal sinuses a sterile aqueous liquid formulation may be used; administered for instance by a nasal spray device, e.g. propellant-free or propellant-assisted. A representative formulation may contain 0.1 to 10%, e.g. 0.1 to 5%, 0.1 to 2%, 0.1 to 1%, 0.1 to 0.8%, 0.1 to 0.5%, 0.1 to 0.2%, 0.2 to 10%, 0.2 to 5%, 0.2 to 2%, 0.2 to 1%, 0.2 to 0.8%, 0.2 to 0.5%, 0.5 to 10%, 0.5 to 5%, 0.5 to 2%, 0.5 to 1%, 0.5 to 0.8%, 0.8 to 10%, 0.8 to 5%, 0.8 to 2%, 0.8 to 1%, 1 to 10%, 1 to 5%, 1 to 2%, 2 to 10%, 2 to 5% or 5 to 10%, w/v of the alginate oligomer, the remainder being comprised of pharmaceutically acceptable excipients, e.g. water, and/or other active agents if being used (e.g. a micro/nanoparticle of use in the invention).

A representative inhalable powder to be used to administer an alginate oligomer of the invention to the lower respiratory tract may contain up to 90%, e.g. up to 85%, 80%, 75% or 70%, e.g. 50 to 90%, 55 to 90%, 60 to 90%, 65 to 90%, 70 to 90%, 75 to 90%, 80 to 90%, 85 to 90%, 50 to 85%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, 75 to 80%, 50 to 70%, 55 to 70%, 60 to 70%, or 65 to 70% w/v or w/w of the oligomer, the remainder being comprised of pharmaceutically acceptable excipients and/or other active agents if being used (e.g. a micro/nanoparticle of use in the invention).

A representative inhalable powder to be used to administer a micro/nanoparticle of use in the invention to the lower respiratory tract may contain up to 90%, e.g. up to 85%, 80%, 75% or 70%, e.g. 50 to 90%, 55 to 90%, 60 to 90%, 65 to 90%, 70 to 90%, 75 to 90%, 80 to 90%, 85 to 90%, 50 to 85%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, 75 to 80%, 50 to 70%, 55 to 70%, 60 to 70%, or 65 to 70% w/v or w/w of the micro/nanoparticle, the remainder being comprised of pharmaceutically acceptable excipients and/or other active agents if being used (e.g. an alginate oligomer of use in the invention).

A representative tablet to be used to administer an alginate oligomer of use in the invention to the lower GI tract may contain up to 99%, up to 95%, 90%, 85% or 80%, e.g. 50 to 95%, 55 to 95%, 60 to 95%, 65 to 95%, 70 to 95%, 75 to 95%, 80 to 95%, 85 to 95%, 90 to 95%, 50 to 90%, 50 to 90%, 55 to 90%, 60 to 90%, 65 to 90%, 70 to 90%, 75 to 90%, 80 to 90%, 85 to 90%, 50 to 90%, 55 to 85%, 60 to 80% or, 65 to 75% w/v or w/w of the oligomer, the remainder being comprised of pharmaceutically acceptable excipients and/or other active agents if being used (e.g. a micro/nanoparticle of use in the invention).

An enteric coated tablet may also be effective in administering an alginate oligomer of use in the invention to the lower GI tract. A representative enteric coated tablet may contain up to 95%, e.g. up to 90%, 85% or 80%, e.g. 55 to 90%, 60 to 90%, 65 to 90%, 70 to 90%, 75 to 90%, 80 to 90%, 85 to 90%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, or 75 to 80% w/v or w/w of the oligomer, the remainder being comprised of pharmaceutically acceptable excipients, including the enteric coating (e.g. polymers including fatty acids, waxes, shellac, plastics, and plant fibres) and/or other active agents if being used (e.g. a micro/nanoparticle of use in the invention).

An enteric coated tablet may also be effective in administering a micro/nanoparticle of use in the invention to the lower GI tract. A representative enteric coated tablet may contain up to 95%, e.g. up to 90%, 85% or 80%, e.g. 55 to 90%, 60 to 90%, 65 to 90%, 70 to 90%, 75 to 90%, 80 to 90%, 85 to 90%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, or 75 to 80% w/v or w/w of the micro/nanoparticle, the remainder being comprised of pharmaceutically acceptable excipients, including the enteric coating (e.g. polymers including fatty acids, waxes, shellac, plastics, and plant fibres) and/or other active agents if being used (e.g. an alginate oligomer of use in the invention).

Enteric coated granules may also be effective in administering an alginate oligomer of use in the invention to the lower GI tract. Such granules may be provided in a capsule which itself may or may not be provided with an enteric coating. A representative enteric coated granule may contain up to 95%, e.g. up to 90%, 85% or 80%, e.g. 55 to 90%, 60 to 90%, 65 to 90%, 70 to 90%, 75 to 90%, 80 to 90%, 85 to 90%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, or 75 to 80% w/v or w/w of the oligomer, the remainder being comprised of pharmaceutically acceptable excipients, including the enteric coating (e.g. polymers including fatty acids, waxes, shellac, plastics, and plant fibres) and/or other active agents if being used (e.g. a micro/nanoparticle of use in the invention).

Enteric coated granules may be effective in administering a micro/nanoparticle of use in the invention to the lower GI tract. Such granules may be provided in a capsule which itself may or may not be provided with an enteric coating. A representative enteric coated granule may contain up to 95%, e.g. up to 90%, 85% or 80%, e.g. 55 to 90%, 60 to 90%, 65 to 90%, 70 to 90%, 75 to 90%, 80 to 90%, 85 to 90%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, or 75 to 80% w/v or w/w of the micro/nanoparticle, the remainder being comprised of pharmaceutically acceptable excipients, including the enteric coating (e.g. polymers including fatty acids, waxes, shellac, plastics, and plant fibres) and/or other active agents if being used (e.g. an alginate oligomer of use in the invention).

A pessary may be used to administer an alginate oligomer and/or a micro/nanoparticle of use in the invention to the lower parts of the female reproductive tract. A representative formulation may contain 1 to 25%, 1 to 20%, e.g. 1 to 15%, 1 to 10%, 1 to 9%, 1 to 8%, 1 to 7%, 1 to 6%, 5 to 25%, 5 to 20%, 5 to 15%, 5 to 10%, 5 to 9%, 5 to 8%, 5 to 7%, 5 to 6%, 8 to 25%, 8 to 20%, 8 to 15%, 8 to 10%, 9 to 25%, 9 to 20%, or 9 to 15% w/v or w/w of the oligomer, the remainder being comprised of pharmaceutically acceptable excipients, including solid excipients (e.g. paraffin and the like), and/or other active agents if being used (e.g. a micro/nanoparticle of use in the invention). Another representative formulation may contain 1 to 25%, 1 to 20%, e.g. 1 to 15%, 1 to 10%, 1 to 9%, 1 to 8%, 1 to 7%, 1 to 6%, 5 to 25%, 5 to 20%, 5 to 15%, 5 to 10%, 5 to 9%, 5 to 8%, 5 to 7%, 5 to 6%, 8 to 25%, 8 to 20%, 8 to 15%, 8 to 10%, 9 to 25%, 9 to 20%, or 9 to 15% w/v or w/w of the micro/nanoparticle, the remainder being comprised of pharmaceutically acceptable excipients, including solid excipients (e.g. paraffin and the like), and/or other active agents if being used (e.g. an alginate oligomer of use in the invention).

A representative aqueous solution for direct delivery of an alginate oligomer of use in the invention to a mucosal surface in the liver, the pancreas or the reproductive system will be sterile and may contain 6 to 25%, e.g. 6 to 20%, 6 to 15%, 6 to 10%, 8 to 25%, 8 to 20%, 8 to 15%, 9 to 25%, 9 to 20%, 9 to 15%, 10 to 15%, 10 to 20%, 10 to 25%, 15 to 20%, or 15 to 25% w/v of the oligomer, the remainder being comprised of water and pharmaceutically acceptable excipients and/or other active agents if being used (e.g. a micro/nanoparticle of use in the invention).

A representative aqueous solution for direct delivery of a micro/nanoparticle of use in the invention to a mucosal surface in the liver, the pancreas or the reproductive system will be sterile and may contain 6 to 25%, e.g. 6 to 20%, 6 to 15%, 6 to 10%, 8 to 25%, 8 to 20%, 8 to 15%, 9 to 25%, 9 to 20%, 9 to 15%, 10 to 15%, 10 to 20%, 10 to 25%, 15 to 20%, or 15 to 25% w/v of the micro/nanoparticle, the remainder being comprised of water and pharmaceutically acceptable excipients and/or other active agents if being used (e.g. an alginate oligomer of use in the invention).

A rectal suppository may be used to administer a micro/nanoparticle of use in the invention to the lower parts of the GI tract. A representative formulation may contain 0.1 to 10%, e.g. 0.1 to 5%, 0.1 to 2%, 0.1 to 1%, 0.1 to 0.8%, 0.1 to 0.5%, 0.1 to 0.2%, 0.2 to 10%, 0.2 to 5%, 0.2 to 2%, 0.2 to 1%, 0.2 to 0.8%, 0.2 to 0.5%, 0.5 to 10%, 0.5 to 5%, 0.5 to 2%, 0.5 to 1%, 0.5 to 0.8%, 0.8 to 10%, 0.8 to 5%, 0.8 to 2%, 0.8 to 1%, 1 to 10%, 1 to 5%, 1 to 2%, 2 to 10%, 2 to 5% or 5 to 10% w/v of the micro/nanoparticle, the remainder being comprised of pharmaceutically acceptable excipients, including solid excipients, and/or other active agents if being used (e.g. an alginate oligomer of use in the invention).

A rectal suppository may be used to administer an alginate oligomer of use in the invention to the lower parts of the GI tract. A representative formulation may contain 0.1 to 10%, e.g. 0.1 to 5%, 0.1 to 2%, 0.1 to 1%, 0.1 to 0.8%, 0.1 to 0.5%, 0.1 to 0.2%, 0.2 to 10%, 0.2 to 5%, 0.2 to 2%, 0.2 to 1%, 0.2 to 0.8%, 0.2 to 0.5%, 0.5 to 10%, 0.5 to 5%, 0.5 to 2%, 0.5 to 1%, 0.5 to 0.8%, 0.8 to 10%, 0.8 to 5%, 0.8 to 2%, 0.8 to 1%, 1 to 10%, 1 to 5%, 1 to 2%, 2 to 10%, 2 to 5% or 5 to 10% w/v of the alginate oligomer, the remainder being comprised of pharmaceutically acceptable excipients, including solid excipients, and/or other active agents if being used (e.g. a micro/nanoparticle of use in the invention).

The invention will be further described with reference to the following non-limiting Examples, in which FIG. 1 shows a schematic representation of the transwell mucus RTN penetration assay of Examples 1 and 2.

Figure 6:
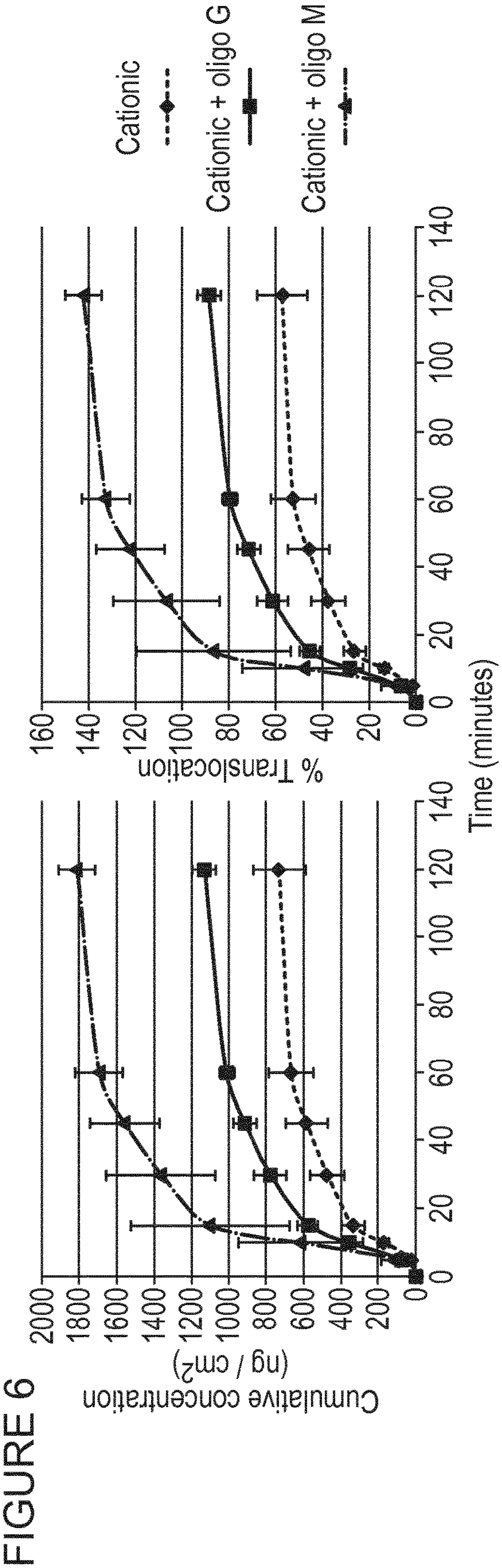

FIG. 6 shows a comparison of the average cumulative concentration ($ng/cm^2$) and % translocation of cationic RTNs in CF mucus through time (minutes) under treatment with OligoG (squares) or OligoM (triangles) or no treatment (diamonds). The mucus was treated with OligoG or OligoM and, after equilibration, the RTNs were added. Error bars represent the standard deviation.

Figure 7:
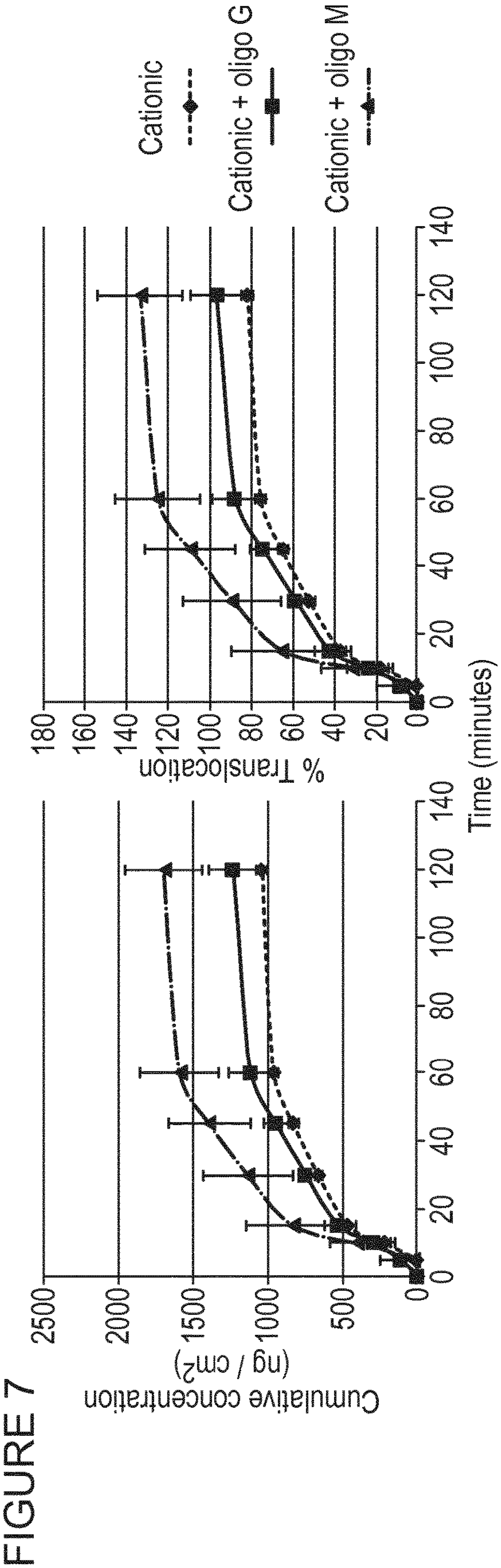
Figure 8:
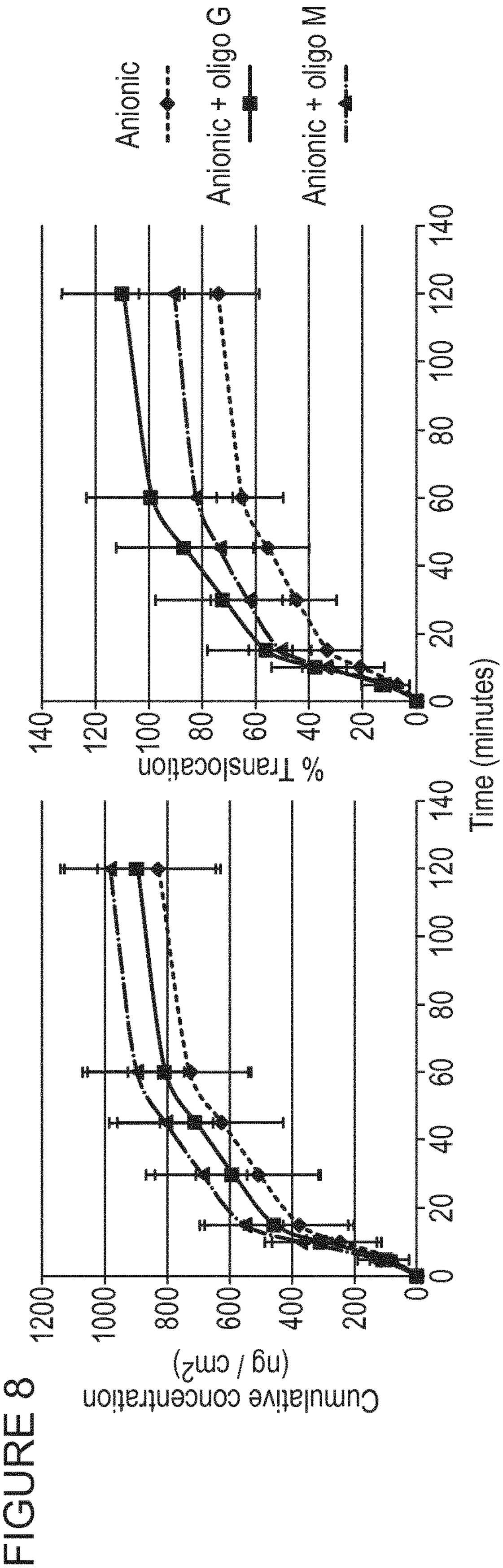

FIG. 7 shows a comparison of the average cumulative concentration ($ng/cm^2$) and % translocation of cationic RTNs in normal mucus through time (minutes) under treatment with OligoG (squares) or OligoM (triangles) or no treatment (diamonds). The mucus was treated with OligoG or OligoM and, after equilibration, the RTNs were added. Error bars represent the standard deviation FIG. 8 shows a comparison of the average cumulative concentration ($ng/cm^2$) and % translocation of anionic RTNs in CF mucus through time (minutes) under treatment with OligoG (squares) or OligoM (triangles) or no treatment (diamonds). The mucus was treated with OligoG or OligoM and, after equilibration, the RTNs were added. Error bars represent the standard deviation.

Figure 9:
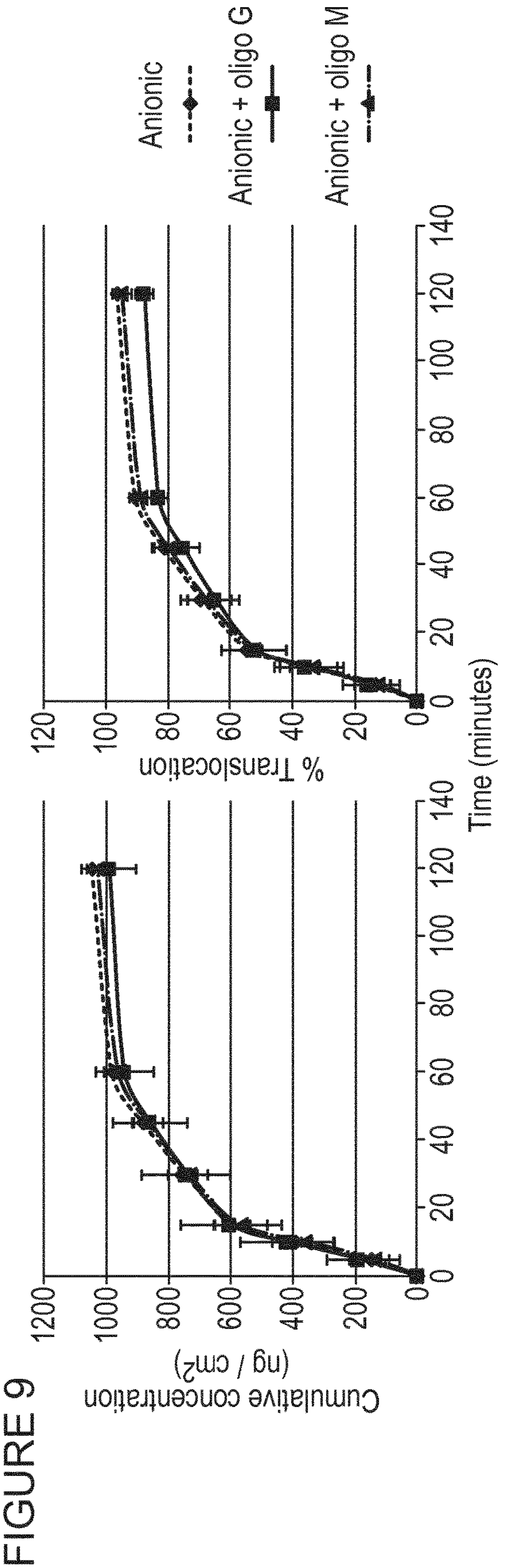

FIG. 9 shows a comparison of the average cumulative concentration ($ng/cm^2$) and % translocation of anionic RTNs in normal mucus through time (minutes) under treatment with OligoG (squares) or OligoM (triangles) or no treatment (diamonds). The mucus was treated with OligoG or OligoM and, after equilibration, the RTNs were added. Error bars represent the standard deviation.

Figure 10:
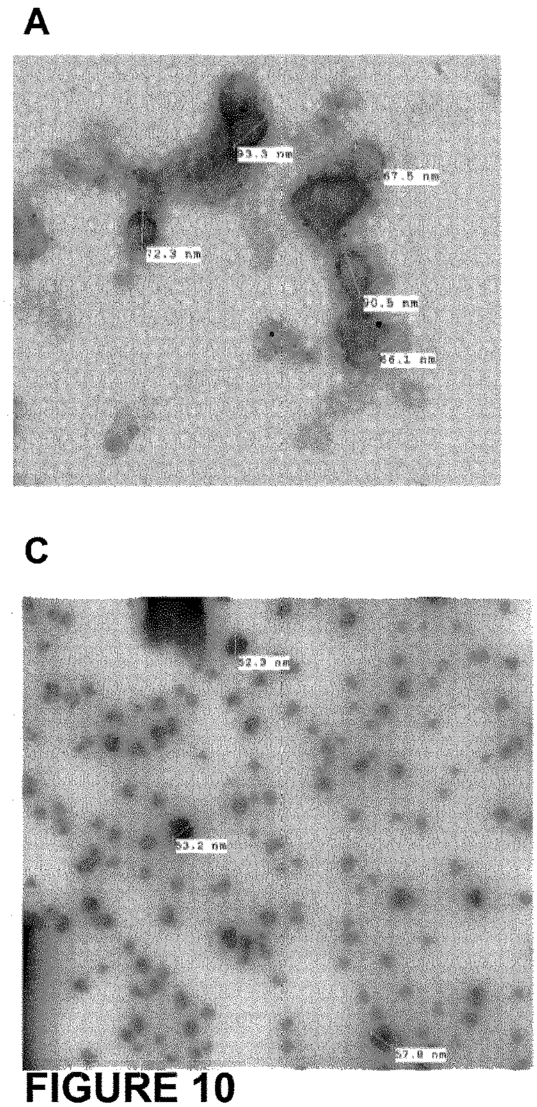

FIG. 10 shows TEM photos of cationic RTNs prior to translocation (A) and following translocation through CF mucus (B) and CF mucus treated with OligoM.

Figure 11:
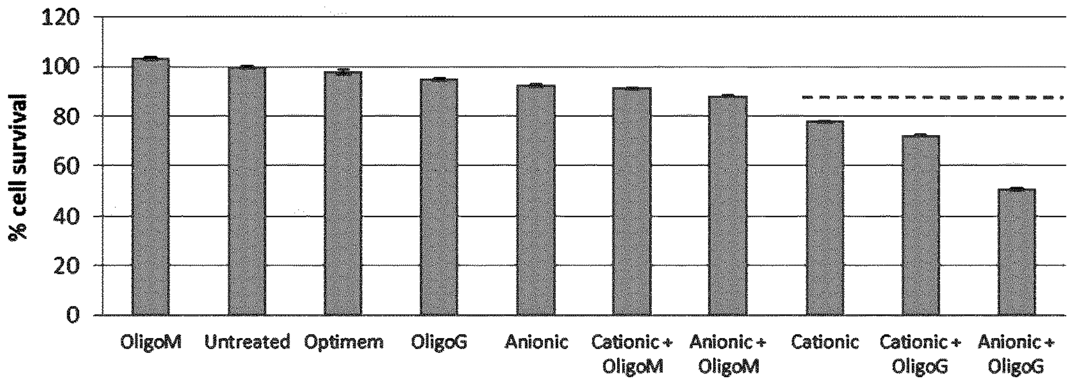

FIG. 11 shows a the percentage of 16HBE cell survival after transfection with cationic and anionic RTNs, with or without OligoG and OligoM, or with OligoG and OligoM alone. Untreated cells are also shown at 100% survival. T-tests with a significance cut-off of $p<0.05$ were conducted, and the conditions that were significantly different from the untreated control are shown with an dashed line. Error bars represent the standard deviation.

Figure 12:
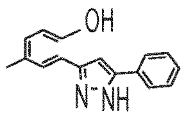
Figure 12:
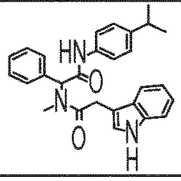
Figure 12:
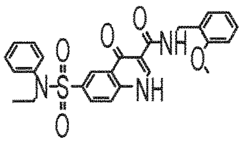
Figure 12:
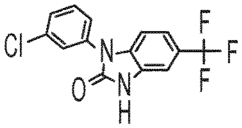
Figure 12:
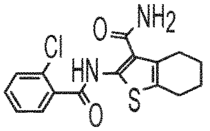
Figure 12:
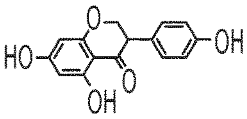
Figure 12:
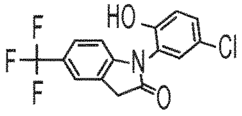
Figure 12:
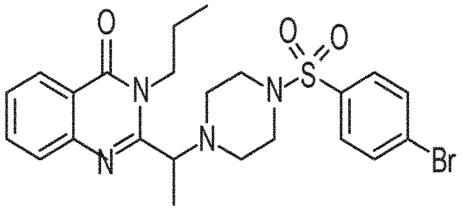
Figure 12:
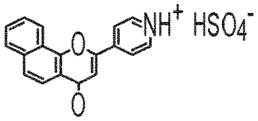
Figure 12:
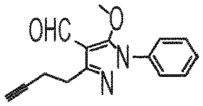
Figure 12:
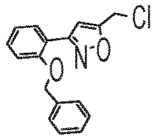
Figure 12:
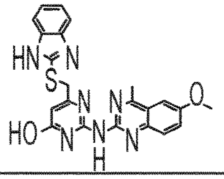
Figure 12:
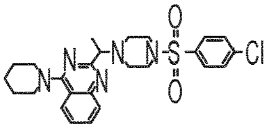
Figure 12:
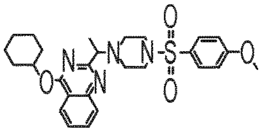
Figure 12:
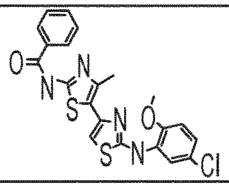
Figure 12:
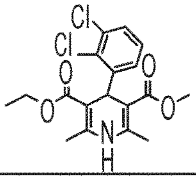
Figure 12:
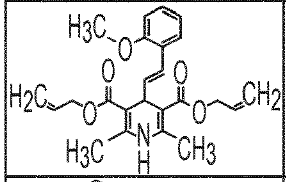
Figure 12:
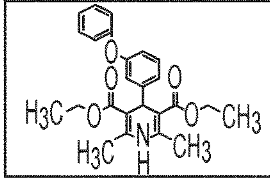

FIG. 12 shows the chemical structures of a variety of CFTR modulators.

EXAMPLES

Example 1—Translocation of Cationic and Anionic Nanoparticles Across Normal and Cystic Fibrosis Mucus and the Effects of Alginate Oligomers

Materials and Methods

Materials

Receptor-Targeted Nanocomplex (RTN) formulations included the liposomes DOTMA/DOPE or DOPG/DOPE (Avanti Polar Lipids, Inc., Alabaster, AL, USA) peptide Y (ChinaPeptides, Shanghai, China), and Cy-3 silencer GAPDH siRNA (Thermo Fisher Scientific, Northumberland, UK).

RTNs used for in vitro transfections were prepared in OPTIMEM (Life Technology, Paisley, UK), while the rest in DNAse/RNAse free water (Thermo Fisher Scientific, Northumberland, UK). All RTNs were incubated at room temperature, while THOSE containing fluorescently labelled siRNA (Cy-3) were kept in the dark.

Cationic siRNA RTNs were made at a 1:4:1 (liposome:peptide:siRNA) weight ratio, by adding peptide Y solution to a solution of DOTMA/DOPE, and lastly Cy-3 siRNA with rapid mixing, and incubating for 30 minutes. Anionic siRNA RTNs were made at a 20:2.7:1 (liposome:peptide:siRNA) weight ratio, by adding the siRNA into the peptide with rapid mixing and incubating it for 30 minutes. Then DOPG/DOPE was added and incubated for another 30 minutes.

The stock concentrations (μg/μl) and an example of the Peptide Y and DOTMA/DOPE dilution factors and the final amounts that were mixed to make the three RTNs, are shown in Tables 1 and 2.

TABLE 1

The dilution factors and amount of components mixed to make the final RTN formulations.

| Ratio | Component | Stock Concentration (μg/μl) | Dilution | Amount mixed (μl) |
|---|---|---|---|---|
| | | Cationic RTN | | |
| 1 | SiRNA | 0.5 | no | 6.3 |
| 4 | PeptideY | 20 | 1 in 10 | 6.3 |
| 1 | DOTMA/DOPE | 0.5 | 1 in 4 | 6.3 |
| | | Anionic RTN | | |
| 1 | SiRNA | 0.5 | no | 6 |
| 2.7 | PeptideY | 20 | 1 in 10 | 4.05 |
| 20 | DOPG/DOPE | 4 | no | 15 |

TABLE 2

Detailed chemical names and structures of the lipid and peptide components used for the RTN formulations

| RTN component | Chemical Name | Structure |
|---|---|---|
| DOPE | 1,2-dioleoyl-sn-glycero-3-phosphoethanolamine | 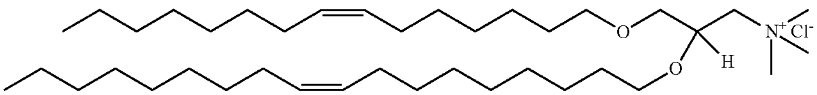 [SMILES: CCCCCCC/C=C\CCCCCCOCC(C[N+](C)(C)C)OCCCCCCCC/C=C\CCCCCCCC ; [Cl-]] |
| DOPG | dioleoyl-phosphatidyl-glycerol | 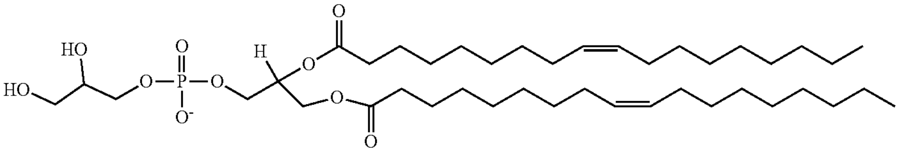 [SMILES: CCCCCCCC/C=C\CCCCCCCC(=O)OCC(COP(=O)([O-])OCC(O)CO)OC(=O)CCCCCCC/C=C\CCCCCCCC] |
| DOTMA | 1,2-di-O-octadecenyl-3-trimethyl-ammonium propane | 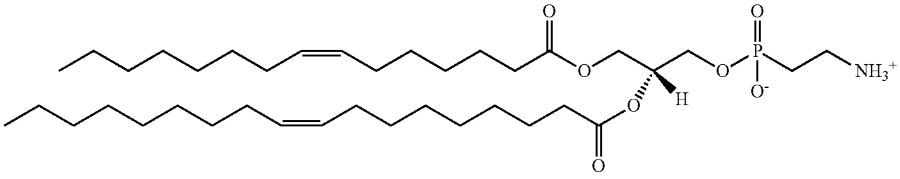 [SMILES: CCCCCCC/C=C\CCCCCC(=O)OC[C@H](COP(=O)([O-])CC[NH3+])OC(=O)CCCCCCC/C=C\CCCCCCCC] |
| PeptideY | Y | $K_{16}$GACYGLPHKFCG |

Alginate oligomers—OligoG (alginate oligomer, DP 5 to 20, average molecular weight 3200 Da, 90-95% G residues) and OligoM (alginate oligomer, 12mer, 100% M) were provided by AlgiPharma AS, Norway.

Transwell Mucus RTN Penetration Assay

The transwell mucus RTN penetration assay was carried out in 24-well plates with transwells (6.5 mm, 3.0 μm pore polyester membrane insert, Corning, UK), in replicates of 2 or 3, placed in a lidded container with water and kept in a 37° C. incubator (FIG. 8). Tris-buffer was prepared using Trizma-Base (Sigma Aldrich, Dorset, UK) at 50 mM and pH 7.4. 600 μl of the Tris-buffer were added in each well and the transwell was placed on top. 1 μl of CF or non-CF (normal) mucus (Epithelix Sarl, Geneva, Switzerland) was added on top and spread across each transwell. 2 μl of 5 mg/ml of OligoG or OligoM (AlgiPharma AS, Norway) were also added in some cases and mixed with the mucus. The plate was incubated for 30 minutes to equilibrate the mucus. 140 ng/μl siRNA RTNs were prepared and 3 μl added on each transwell. A positive control of Tris-buffer with 3 μl of 140 ng/μl siRNA and a negative control of plain Tris-buffer were also included. After 5, 10, 15, 30, 45, 60 and 120 minutes, 200 μl of the Tris-buffer were collected and pipetted into 96-well plates (Nunc MicroWell, 96-Well, Optical-Bottom, Coverglass Base, Thermo-Fisher Scientific). 200 μl of Tris-buffer were replaced in the well after each collection. SiRNA fluorescence was measured in a FLUOstar OPTIMA Microplate Reader (BMG, Labtech) (560±10 nm excitation, 590±10 nm emission wavelength).

Determining RTN Size and Charge

RTN formulations were diluted with DNAse/RNAse-free water to 1 mL at a 1 μg/mL siRNA concentration and their size and charge (ζ-potential) were determined using a Malvern Nano ZS Zetasizer (Malvern, UK) with 10 measurements per sample automatic sampling, 1.330 refractive index, 78.5 dielectric constant, 0.8871 cP viscosity and 25° C. temperature, processed using the manufacturer's DTS program (v5.03).

Cumulative Concentration and Percentage Translocation Calculations

Initially the percentage translocation of the RTNs through the mucus needs to be calculated. Raw fluorescence data for the RTN assay through mucus are obtained from the fluorimeter. The negative control values (Tris buffer) are subtracted from their respective sample data and positive control (siRNA in Tris buffer). Cumulative data are calculated by adding the 5 minute data to the 10 minute data, the 10 minute data to the 15 minute data and so on. The sum of the positive control is also calculated. Percentage translocation of the RTN through mucus is calculated by multiplying the cumulative data with 100 and dividing them by the sum of the positive control.

To calculate the cumulative concentration, the percentage penetration data are initially divided by 100. These data are now multiplied by 420—that is the concentration of the siRNA inside the cationic RTN in ng (140 ng/μl siRNA×3 μl added in each well=420 ng/well). This is different for the anionic formulations where the data would need to be multiplied by 358.4 ng/well. Finally, these data are divided by 0.33 that is the surface area of the transwells used in the assay, in $cm^2$.

Significance was determined by two-sample T-tests with a p-value significance cut-off of $p<0.05$.

RTN Diffusion Through Mucus

The diffusion of RTNs through mucus is calculating using Fick's second Law;

$$\frac{dM}{dt} = \frac{DC}{h}$$ Formula I (Fick's second Law)

dM/dt is the flux (F) per $ng/s/cm^2$ (identified by the equation of the linear trendline of the plotted RTN cumulative concentrations to calculate the rate of transport at a steady state), D is the diffusion coefficient in $cm^2\ s^{-1}$, C is the concentration of the SiRNA on the mucus in $ng/cm^3$, and h is the thickness of the mucus on the transwell in cm.

To find the flux, a scatter XY graph of the cumulative concentration data points is plotted, with a selection of points before the graph's curve reaches a plateau. The plotted graph needs to have as straight of a line as possible before adding a linear trendline that displays its equation and $R^2$ value. The $R^2$ value needs to be as close to 1 as possible to obtain the best theoretical flux value.

In the present Example the flux is 9.86 ng/cm$^2$/min.

In order for the flux to be applied on Fick's equation, in needs to be calculated in seconds. To do that, the flux is divided by 60.

Flux=9.86/60=0.16 ng/cm$^2$/s h=barrier (transwell) thickness in cm=0.0035 cm $C_0$=the concentration of the SiRNA inside the RTN in ng/cm$^3$=140000 ng/cm$^3$ for cationic RTNs, 119800 ng/cm$^3$ for anionic RTNs Solving for D will result in the diffusion of the RTNs through mucus ($D_m$) in cm$^2$ s$^{-1}$.

RTN Diffusion Through Water

The diffusion of RTNs through water is calculated using Formula II (Stoke's Law);

$$D = \frac{KT}{6\pi\eta r} \qquad \text{Formula II (Stoke's Law)}$$

D is the diffusion coefficient in cm$^2$ s$^{-1}$, K is the Boltzman constant, T is the temperature in Kelvin, $\eta$ is the viscosity in gs$^{-1}$ nm$^{-1}$, and r the radius of the RTN.

Boltzman constant=1.38E-02 nm$^2$ gs$^{-2}$ k$^{-1}$

Temperature=310 Kelvin

Pi=3.1416

Viscosity=6.92E-10 gs$^{-1}$ nm$^{-1}$

Radius=The measured size of the RTN in nm (diameter), divided by 2.

Solving for D will result in the diffusion of the RTNs through watwe ($D_w$) in nm$^2$ s$^{-1}$.

This value needs to be transformed in cm$^2$ s$^{-1}$ by multiplying $D_w$ with $10^{-8}$.

Transmission Electron Microscopy (TEM)

For the electron microscopy investigations, the RTNs prepared as described above were applied onto a 300-mesh copper grid coated with a Formvar/carbon support film (Agar Scientific). Prior to preparation, the grids were "glow discharged" in an Emitech K350G system (Emitech Ltd.) for 15 s at 30 mA (negative polarity). After a few seconds, the grid was dried by blotting with filter paper. The sample (nanoparticles) was then negatively stained with 1% uranyl acetate for 2-3 s, before blotting with filter paper and air-dried. Imaging was performed with a Philips CM120 BioTwin transmission electron microscope and operated at an accelerating voltage of 120 kV. The images were captured using an AMT 5MP digital TEM camera (Deben UK Limited, Bury St. Edmunds, Suffolk).

MTS Cell Viability Assay

Cell viability of siRNA RTNs and OligoG or OligoM was tested. RTN siRNA formulations at 100 ng/well, 15 µl of 5 mg/ml OligoG and OligoM and 15 µl of either OligoG or OligoM combined with the different siRNA RTN formulations were all made up to 150 µl with OPTIMEM. These were added to 16HBE cells in 96 well plates (Greiner Bio-One, microplate, PS, flat-bottom, clear) and left for four hours. The cells were washed with PBS and 150 µl fresh media was replaced. After 24 hours, the media was removed and 100 µl of fresh media with 20 µl of MTS assay reagent (Promega) was added. After four hours of incubation the absorbance was measured using the FLUOstar OPTIMA Microplate Reader at 490 nm (BMG, Labtech).

Results

Cationic and Anionic RTN Translocation Across Cystic Fibrosis Mucus

Cy3-tagged siRNA-containing cationic and anionic RTNs were prepared and measured for size and charge. Their average values are reported in Table 3 and remain the same throughout all of the transwell mucus penetration assays conducted on CF mucus.

TABLE 3

Size and charge measurements of the RTN formulations for assays with CF mucus

| | Size | Charge |
|---|---|---|
| Cationic | 158.7 | 46.6 |
| Anionic | 169.8 | −38.48 |

Figure 1:
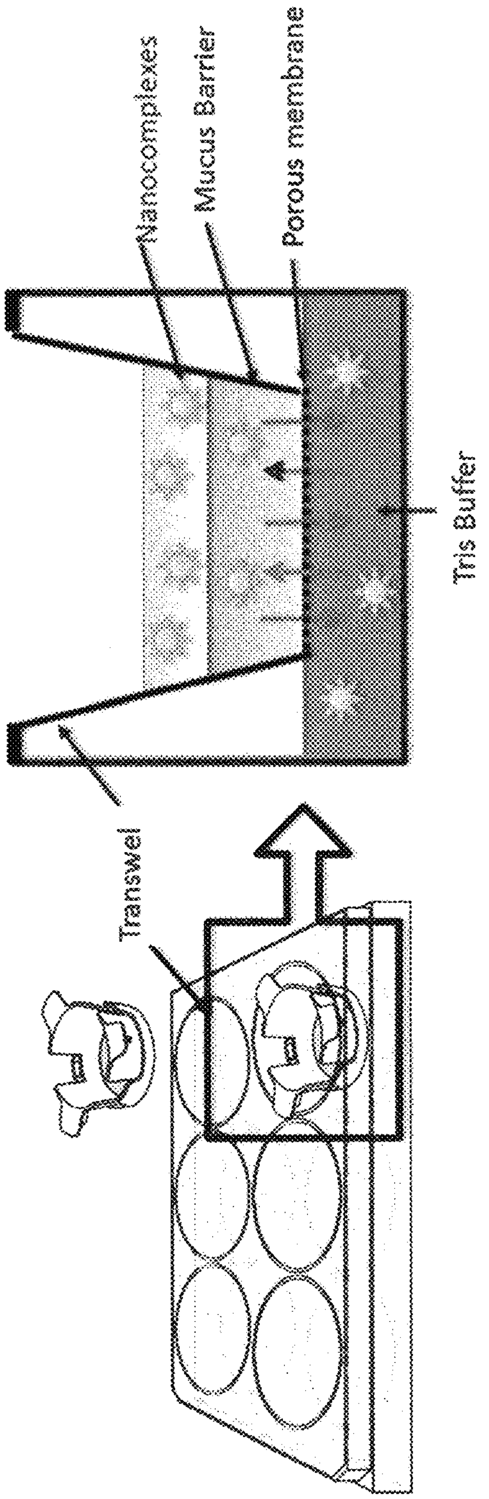

These RTNs were added on top of a mucus layer on transwells (FIG. 1) to mimic the mucus barrier of the airway epithelia—allowed to translocate through the membrane and deposited into a buffer solution (Tris buffer). Buffer samples with the translocated RTNs were collected at specific time points of 5, 10, 15, 30, 45, 60 and 120 minutes. RTN fluorescence was measured and compared to a siRNA positive control to determine the cumulative RTN translocation after the specific time points. The percentage (%) translocation and cumulative concentration of the RTNs was then calculated, normalizing for the differences in siRNA concentrations in the different RTN formulations. The average % translocations and cumulative concentrations from all the experiments conducted were also calculated. The % translocation can show the extent of the RTN penetration through to the collection buffer as it is calculated compared to its respective 100% siRNA positive controls, and can determine whether the RTN is mobile through the mucus. Finally, by applying Fick's and Stoke's laws for the diffusion of nanoparticles through mucus and water respectively, the diffusion rates of the RTNs were determined and compared (Table 12).

Figure 2:
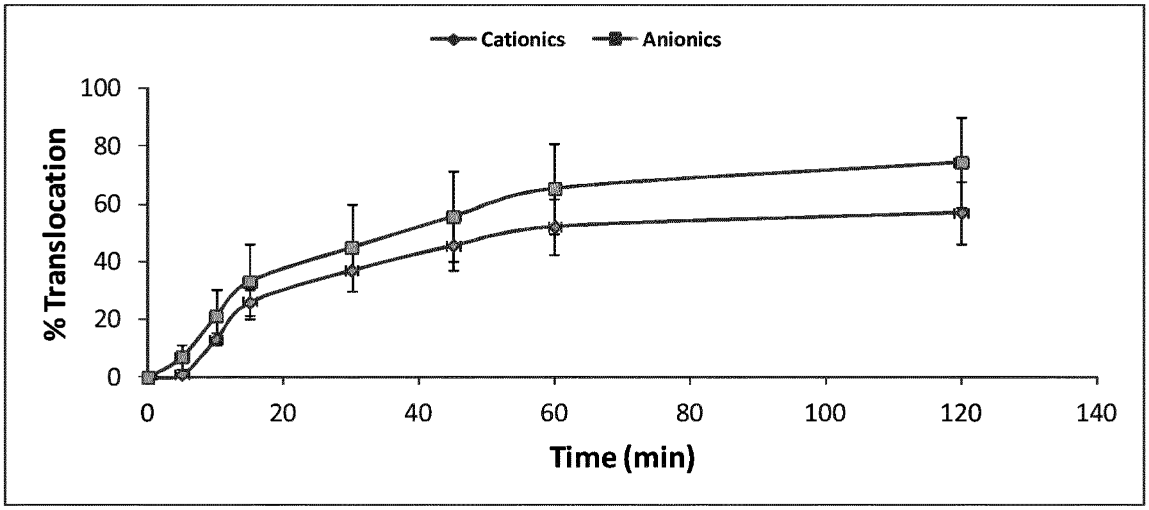
FIG. 2 shows the % translocation of anionic (squares) and cationic (diamonds) RTNs in CF mucus through time (minutes). Error bars represent the standard deviation.
Figure 3:
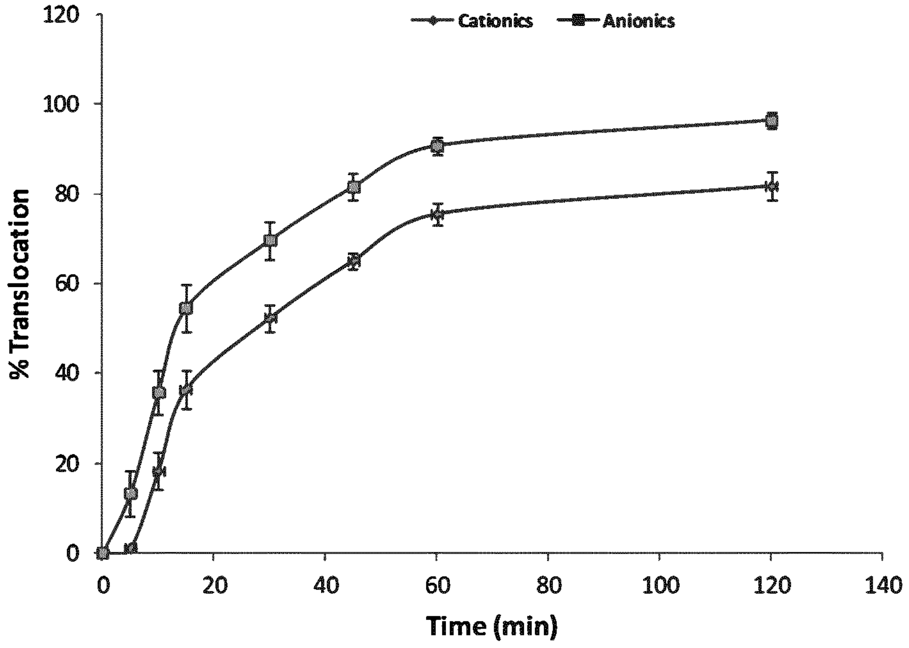
FIG. 3 shows the % translocation of anionic (squares) and cationic (diamonds) RTNs in normal mucus through time (minutes). Error bars represent the standard deviation.

FIG. 2 shows that anionic RTNs have a higher % translocation than cationic RTNs.

Cationic and Anionic RTN Translocation Across Normal Mucus

Similarly to the experiments with CF mucus, experiments using mucus from healthy donors (referred to as 'normal mucus') were conducted. Average size and charge values of the formulations used, are depicted in Table 4 and remain the same throughout all of the transwell mucus penetration assays conducted on normal mucus.

TABLE 4

Size and charge measurements of the RTN formulations for assays with normal mucus.

| | Size | Charge |
|---|---|---|
| Cationic | 121.3 | 48.1 |
| Anionic | 160.5 | −40.9 |

The RTN formulations have an acceptable size around 140±50 nm that is the pre-determined pore size of CF mucus and were used for the transwell mucus penetration assay, this time with normal mucus as a barrier on the transwell membrane. The samples were collected and their fluorescence from Cy3-siRNA was determined. The percentage (%) translocation and cumulative concentration of the RTNs was then calculated, normalizing for the differences in siRNA concentrations in the different RTN formulations. The average % translocations and cumulative concentrations from all the experiments conducted were also calculated. by applying Fick's and Stoke's laws for the diffusion of nanoparticles through mucus and water respectively, the diffusion rates of the RTNs were determined and compared (Table 12).

Anionic RTNs have the higher percentage translocation than cationic RTNs. T-tests on the % translocations show that the cationic RTNs are significantly different from the anionic RTNs (Table 5).

TABLE 5

T-test p-values of combinations of the % translocations of RTN formulations in normal mucus, through time. Significance is indicated in italics with a cut-off of $p < 0.05$.

T-test on % translocation of RTNs formulations in CF mucus (p-values)

| Time (minutes) | 5' | 10' | 15' | 30' | 45' | 60' | 120' |
|---|---|---|---|---|---|---|---|
| Cationic:Anionic | 0.003 | 0.002 | 0.002 | 0.001 | 0.0001 | 0.0001 | 0.0001 |

Figure 4:
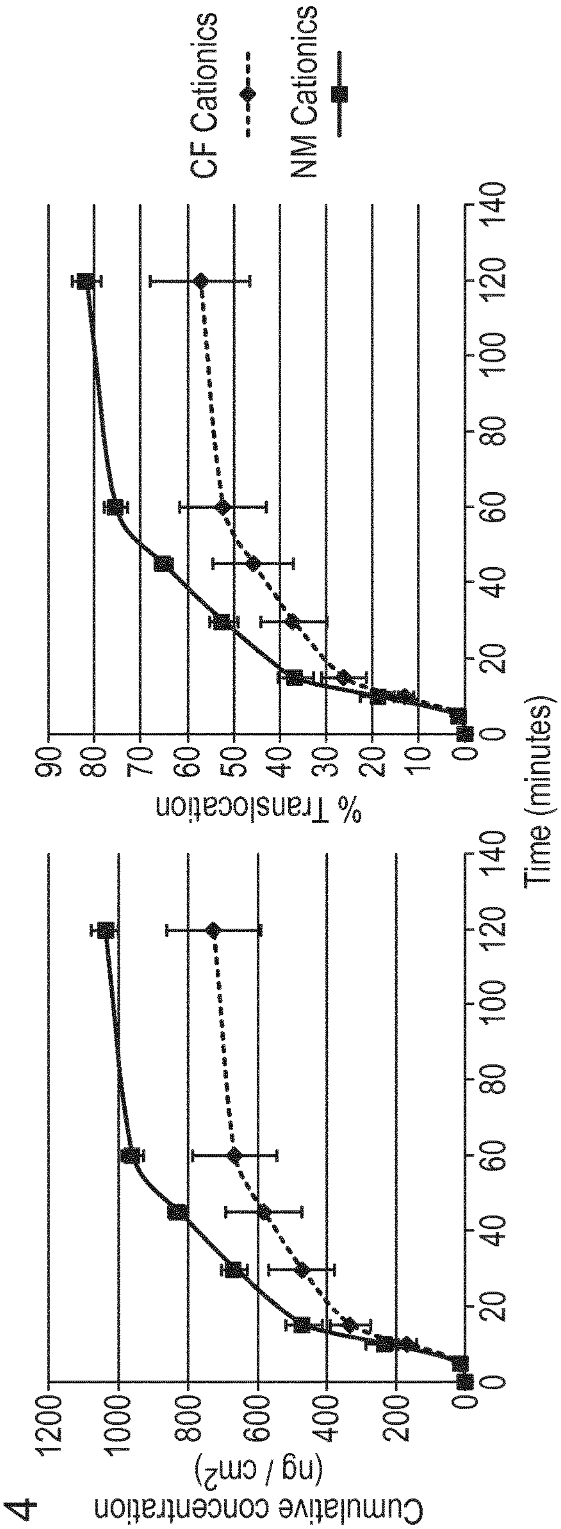
FIG. 4 shows a comparison of the cumulative concentration ($ng/cm^2$) and the % translocation of cationic RTN formulations through CF (diamonds) and normal mucus (NM; squares). Error bars represent the standard deviation.
Figure 5:
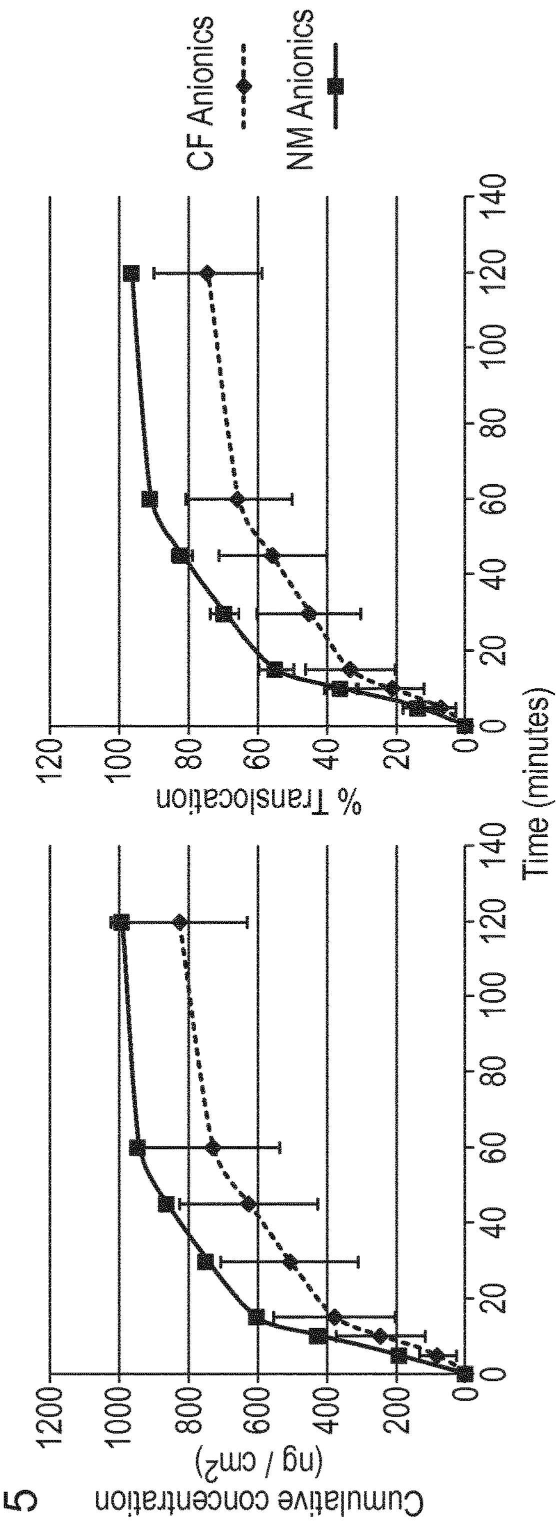
FIG. 5 shows a comparison of the cumulative concentration ($ng/cm^2$) and the % translocation of anionic RTN formulations through CF (diamonds) and normal (squares) mucus. Error bars represent the standard deviation.

Comparison of the Translocation of Cationic and Anionic RTNs Across CF and Normal Mucus Comparing the translocation of different RTN formulations in CF or normal mucus would determine if CF mucus does indeed slow RTNs down, and the extent of this cumulative FIGS. 4 and 5 show that when applied to CF mucus both RTN formulations have a decreased RTN cumulative concentration and % translocation, as compared to normal mucus. In the cationic and anionic formulations the cumulative concentration is 30 and 20% lower in CF mucus respectively. T-tests determined that the translocation rates of cationic and anionic RTNs on CF and normal mucus is significantly different (Table 6).

TABLE 6

T-tests comparing CF and normal mucus cumulative concentrations for cationic and anionic RTNs at various timepoints. Significance is indicated in italics with a cut-off of $p < 0.05$.

CF vs Normal mucus T-test on all RTNs (p-values)

| Time (minutes) | 0' | 5' | 10' | 15' | 30' | 45' | 60' | 120' |
|---|---|---|---|---|---|---|---|---|
| Cationics | 0.00 | 0.46 | 0.13 | 0.01 | 0.00 | 0.00 | 0.00 | 0.00 |
| Anionics | 0.00 | 0.09 | 0.07 | 0.04 | 0.04 | 0.03 | 0.03 | 0.05 |

The Effects of OligoG and OligoM on RTN Translocation Across Mucus Layers

Having established the trend of RTN translocation through mucus, OligoG and OligoM were used to determine if they could enhance RTN translocation efficiency and increase their cumulative concentration. OligoG and OligoM are tested with the same transwell mucus penetration assays as described above for both cationic and anionic RTN formulations.

Cationic RTNs

FIG. 6 shows the effects of OligoG and OligoM on cationic RTN translocation across CF mucus layers. Untreated cationic RTNs have the lowest translocation efficiency while both OligoG and OligoM increase the cumulative concentration and % translocation of the cationic RTN formulations. OligoM shows a significantly higher RTN final concentration compared to OligoG, an observation backed up by T-tests (Table 7) and ANOVA.

TABLE 7

T-test values of the cumulative concentrations of cationic RTNs in untreated or Oligo treated CF mucus. Cationic RTNs in CF mucus (None) are compared to cationic RTNs in CF mucus treated with OligoG or OligoM. Cationic RTNs in CF mucus treated with OligoG are compared to cationic RTNs in CF mucus treated with OligoM. Significance is indicated in italics with a cut-off of $p < 0.05$.

Untreated vs Oligoc treated CF mucus T-test on cationic RTNs (p-values)

| Time (minutes) | | 5' | 10' | 15' | 30' | 45' | 60' | 120' |
|---|---|---|---|---|---|---|---|---|
| None | OligoG | 2.4E−05 | 0.0015 | 0.0087 | 0.0186 | 0.01989 | 0.0185 | 0.0195 |
| None | OligoM | 0.0683 | 0.0377 | 0.0155 | 0.0035 | 0.00109 | 0.0006 | 0.0006 |
| OligoG | OligoM | 0.7984 | 0.3843 | 0.2256 | 0.1123 | 0.04332 | 0.0193 | 0.0147 |

The cumulative concentration of the cationic RTNs translocating through CF mucus treated with OligoG and OligoM, is significantly different from that of untreated CF mucus for all the time points. Similarly, OligoM has a significantly better effect at cationic RTN translocation compared to OligoG especially after the 45 minute collection time point and the % translocation even exceeds notional 100% penetration. ANOVA multiple comparison tests on the final 120 minute time point similarly show that both Oligos have a significantly different RTN cumulative concentration effect, compared to untreated mucus and that OligoM has a significantly increased effect on the RTNs' penetration efficiency and rate as compared to OligoG.

A similar trend to that seen in CF mucus can be detected when using normal mucus for this assay (FIG. 7). As seen in CF mucus, OligoM increases the RTN translocation efficiency the most, compared to OligoG or untreated normal mucus. OligoG still shows a higher cumulative concentration to untreated normal mucus but not as high as that of OligoM that also exceeds 100% translocation, as observed in CF mucus. The significance of these observations is highlighted by T-tests seen below (Table 8).

TABLE 8

T-test values of the cumulative concentrations of cationic RTNs in untreated or Oligo treated normal mucus. Cationic RTNs in normal mucus (None) are compared to cationic RTNs in normal mucus treated with OligoG or OligoM. Cationic RTNs in normal mucus treated with OligoG are compared to cationic RTNs in normal mucus treated with OligoM. Significance is indicated in italics with a cut-off of $p < 0.05$.
Untreated vs Oligo treated normal mucus T-test on cationic RTNs (p-values)

| Time (minutes) | | 5' | 10' | 15' | 30' | 45' | 60' | 120' |
|---|---|---|---|---|---|---|---|---|
| None | OligoG | 0.216 | 0.459 | 0.285 | 0.019 | 0.041 | 0.099 | 0.077 |
| None | OligoM | 0.077 | 0.133 | 0.061 | 0.021 | 0.007 | 0.003 | 0.002 |
| OligoG | OligoM | 0.304 | 0.424 | 0.178 | 0.080 | 0.046 | 0.039 | 0.043 |

OligoM has a significant effect on increasing the cationic RTN's cumulative concentration after the 30 minute time point, but the same is true for OligoG only at the 30 and 45 minute time points. OligoM shows a significant enhancement of the rate of translocation of the RTN, compared to that of OligoG in time points after 45 minutes, with a steeper increase of the RTN cumulative concentration. In contrast, mucus treatment with OligoG seems to show the same translocation profile to the untreated mucus, albeit with a consistently higher cumulative RTN concentration. ANOVA tests also validate the t-test results at the final time point.

Anionic RTNs

FIG. 8 shows the effects of OligoG and OligoM on anionic RTN translocation across CF mucus layers. Both Oligos show a tendency for a higher cumulative concentration and % translocation, compared to untreated CF mucus but these differences were found not to be significant (Table 9) and confirmed by ANOVA tests (not shown).

TABLE 9

T-test values of the cumulative concentrations of anionic RTNs in untreated or Oligo treated CF mucus. Anionic RTNs in CF mucus (None) are compared to anionic RTNs in CF mucus treated with OligoG or OligoM. Anionic RTNs in CF mucus treated with OligoG are compared to anionic RTNs in CF mucus treated with OligoM. Significance is indicated in italics with cut-off of $p < 0.05$ is used.
Untreated vs Oligo treated CF mucus T-test on anionic RTNs (p-values)

| Time (minutes) | | 5' | 10' | 15' | 30' | 45' | 60' | 120' |
|---|---|---|---|---|---|---|---|---|
| None | OligoG | 0.533 | 0.514 | 0.534 | 0.573 | 0.575 | 0.596 | 0.633 |
| None | OligoM | 0.168 | 0.160 | 0.155 | 0.192 | 0.206 | 0.225 | 0.254 |
| OligoG | OligoM | 0.667 | 0.587 | 0.557 | 0.596 | 0.614 | 0.615 | 0.602 |

The same experiment was conducted in normal mucus treated (or not) with OligoG or OligoM. Results are shown in FIG. 9. Here, the ineffectiveness of the Oligos is more evident, as all the plotted lines are extremely close to each other and show almost the same trend. There is a slight differentiation in the final time points of 120 minutes, showing that the mucus treated with OligoG has a marginally lower cumulative RTN concentration, while the untreated mucus has a slightly higher one. However, all conditions are statistically non-significant, something validated by the t-test (Table 10) and ANOVA values (not shown).

TABLE 10

T-test values of the cumulative concentrations of anionic RTNs in untreated or Oligo treated normal mucus. Anionic RTNs in normal mucus (None) are compared to anionic RTNs in normal mucus treated with OligoG or OligoM. Anionic RTNs in normal mucus treated with OligoG are compared to anionic RTNs in normal mucus treated with OligoM. Significance is indicated in italics with a cut-off of $p < 0.05$.
Untreated vs Oligo treated normal mucus T-test on anionic RTNs (p-values)

| Time (minutes) | | 5' | 10' | 15' | 30' | 45' | 60' | 120' |
|---|---|---|---|---|---|---|---|---|
| None | OligoG | 0.489 | 0.718 | 0.936 | 0.876 | 0.670 | 0.370 | 0.251 |
| None | OligoM | 0.914 | 0.721 | 0.698 | 0.657 | 0.534 | 0.453 | 0.456 |
| OligoG | OligoM | 0.571 | 0.671 | 0.805 | 0.938 | 0.936 | 0.715 | 0.514 |

The Effect of OligoG and OligoM on RTN Size and Charge

After determining that mucus treatment with OligoG and OligoM shows significant differences in the translocation of RTN formulations, mainly cationic RTNs, an attempt was made to discover if this is caused as a result of altering the RTNs' charges. Anionic and cationic RTN formulations were made and divided in three equal eppendorfs. Two were treated for 2 minutes with OligoG or OligoM. Their size and charges were measured (Table 11).

TABLE 11

Size and charge measurements for cationic and anionic RTNs that are untreated, or treated with OligoG or OligoM). The effect of OligoG and OligoM on RTN size & charge

| | untreated | OligoG | OligoM |
|---|---|---|---|
| cationic | | | |
| size | 176.2 | 131.4 | 125.1 |
| charge | 36.2 | −37.6 | −36.6 |
| anionic | | | |
| size | 145.8 | 165.7 | 155.1 |
| charge | −45.7 | −65.8 | −59.4 |

Table 11 shows that both Oligos change the charge of the cationic and the anionic RTNs, making it more negative. This is mostly evident with the cationic RTNs, were their charge completely changes from positive to negative, almost to a similar level of charge as the untreated anionic RTNs. It is also evident that, especially in cationic formulations, their size decreases after each measurement. The untreated one was measured first, while the OligoG and OligoM treated ones were measured afterwards, with each measurement lasting around 20 minutes. Even though OligoM seems to create slightly smaller charge differences from OligoG, the values are not significantly different from one another.

Fold-Impedance of RTNs in CF and Normal Mucus

Using Fick's and Stoke's laws, the diffusion coefficients of the RTNs in CF and normal mucus that was treated or not with OligoG or OligoM along with their fold impedance were calculated (Table 12). These calculations take into account the size of the nanocomplexes and can determine the fold-impedance of those RTNs in mucus, when compared to their diffusion in water, which acts as a control for optimal obstacle-free diffusivity.

TABLE 12

The diffusion rates ($D_m$) of cationic and anionic RTNs in CF and normal mucus (NM), treated or not with OligoG or OligoM. $D_w$ represents the diffusion of the RTNs in water. Fold-impedance represents the retardation of the RTNs through mucus when compared to water.

| | CF MUCUS | | | |
|---|---|---|---|---|
| RTN (+/−Oligo) | Diffusion in CF ($cm^2\ s^{-1}$) | Diffusion in water ($cm^2\ s^{-1}$) | $D_m/D_w$ (CF) | Fold-impendance |
| Cationic | 6.08E−09 | 4.13E−08 | 1.47E−01 | 6.79 |
| Cationic + OligoG | 8.92E−09 | 4.13E−08 | 2.16E−01 | 4.64 |
| Cationic + OligoM | 1.58E−08 | 4.13E−08 | 3.82E−01 | 2.62 |
| Anionic | 6.79E−09 | 3.86E−08 | 1.76E−01 | 5.69 |
| Anionic + OligoG | 7.54E−09 | 3.86E−08 | 1.95E−01 | 5.13 |
| Anionic + OligoM | 8.50E−09 | 3.86E−08 | 2.20E−01 | 4.54 |

TABLE 12-continued

The diffusion rates ($D_m$) of cationic and anionic RTNs in CF and normal mucus (NM), treated or not with OligoG or OligoM. $D_w$ represents the diffusion of the RTNs in water. Fold-impedance represents the retardation of the RTNs through mucus when compared to water.

| | NORMAL MUCUS | | | |
|---|---|---|---|---|
| RTN (+/−Oligo) | Diffusion in NM ($cm^2\ s^{-1}$) | Diffusion in water ($cm^2\ s^{-1}$) | $D_m/D_w$ (NM) | Fold-impendance |
| Cationic | 8.72E−09 | 5.41E−08 | 1.61E−01 | 6.20 |
| Cationic + OligoG | 8.89E−09 | 5.41E−08 | 1.64E−01 | 6.08 |
| Cationic + OligoM | 1.46E−08 | 5.41E−08 | 2.70E−01 | 3.71 |
| Anionic | 9.31E−09 | 4.09E−08 | 2.28E−01 | 4.39 |
| Anionic + OligoG | 8.42E−09 | 4.09E−08 | 2.06E−01 | 4.85 |
| Anionic + OligoM | 9.15E−09 | 4.09E−08 | 2.24E−01 | 4.47 |

In both CF and normal mucus, the cationic RTN's fold-impedance is significantly reduced after treatment with OligoM when compared to untreated mucus (2.6 and 1.7-fold respectively). OligoM has a 1.8 fold-difference in decreasing mucus impedance in CF mucus, and 1.7 fold-difference in normal mucus, compared to OligoG. In the case of anionic RTN's the Oligos do not have a significant effect on increasing or decreasing the translocation efficiency.

Transmission Electron Microscopy (TEM) of RTNs Recovered from the Transwell

As shown in FIG. 10 cationic RTNs recovered from the lower transwell chamber following translocation across CF mucus layers both in the presence or absence of OligoM are structurally intact and substantially unchanged as compared to their form prior to translocation.

Cytotoxicity of OligoG, OligoM and RTNs

An MTS assay was carried out to determine if the RTNs and/or OligoG or OligoM alone or together cause toxicity to 16HBE cells cells (immortalized human bronchial epithelial cells). 16HBE cells were seeded on 96-well plates at a 60-70% confluency and left to incubate overnight. RTN formulations were applied at 100 ng/well. The Oligos were either mixed with the RTNs or with OPTIMEM alone, at the time of the transfection. After 4 hours, the test media was removed and replaced with fresh media and the MTS solution for another 4 hours. Then, their absorbance was read and compared to the untransfected controls to calculate the % survival of the cells under each tested condition. The results are shown in FIG. 11.

As can be seen, OligoG alone is more toxic to the cells compared to OligoM alone. Moreover, anionic RTNs are less toxic than the cationic RTNs. T-tests between cationic and anionic RTN formulations, indicated that cationic RTNs have a significantly higher toxicity compared to the anionic RTNs (p-value 0.0276; a p-value cut-off significance is $p<0.05$). The highest and most significant toxicity is seen in RTNs combined with OligoG. On the other hand, OligoM renders cationic RTNs less toxic than cationic RTNs alone and has no effect on anionic RTN toxicity.

DISCUSSION

The following conclusions may be drawn from this study:

1. CF mucus inhibits the translocation of RTNs more than normal mucus.
2. Anionic RTNs translocate more effectively than cationic RTNs in both normal and CF mucus.
3. Oligo M enhances cationic RTN translocation through normal and CF mucus to a much greater extent than OligoG.

4. OligoM has no significant effect on the translocation of anionic RTNs.
5. Cationic RTNs when used with OligoM have the highest diffusion rates in all systems tested herein.
6. Cationic RTNs remain structurally intact and substantially unchanged as compared to their form prior to translocation through CF mucus in the presence or absence of OligoM.
7. OligoM renders cationic RTNs less cytotoxic to 16HBE cells.

Example 2—the Effects of PEGylation on the Translocation of Cationic Nanocomplexes Through Normal and CF Human Airway Mucus Methods Cationic Nanocomplex Formulation Cationic nanocomplexes made of DOTMA/DOPE liposome (0.5 μg/μL) with 0, 5 or 10% PEG (each PEG at 2.5 μg/μL), peptide Y (2 μg/μL) and Cy3-labelled siRNA (0.5 μg/μL, Thermo Fisher Scientific) at a 1:4:1 weight ratio, respectively, were formulated. For example, liposome (1 μg) and peptide Y (4 μg) were added to nuclease-free water (1 μL). Cy3-labelled siRNA (1 μg) was then added to the mixture with rapid mixing. The nanocomplexes were incubated at room temperature away from light for 30-40 min to allow complex formation.

Cationic Nanocomplex Characterisation

The size and zeta potential of each nanocomplex were measured using the Zetasizer Nano ZS. Nanocomplexes (10 μL for cationic with 0% PEG or 16.7 μL for those with 5 or 10% PEG) were diluted in MilliQ water (volume required to make solution up to 940 μL). 920 μL of each diluted nanocomplex sample were transferred to a cuvette and placed into the Zetasizer Nano ZS to measure its size and then zeta potential.

Transwell Assay

As described in Example 1

Results

Cationic nanocomplexes made of DOTMA/DOPE with 0, 5 or 10% PEG, peptide Y and Cy3-labelled siRNA at a 1:4:1 weight ratio, respectively, were formulated. Cy3-labelled siRNA allowed for the quantification of nanocomplex translocation through normal and CF human mucus by measuring the fluorescence. The cumulative penetrations and concentrations of translocated nanocomplexes were quantified and plotted. The size and zeta potential of each nanocomplex were also measured. This was done to calculate the diffusion rates of translocated nanocomplexes in mucus and water using Fick's and Stokes' laws, respectively. Taken together, these data allowed for the effects of PEGylation on cationic nanocomplex translocation through normal and CF mucus to be investigated.

TABLE 13

The characterisation of cationic nanocomplexes with 0, 5 and 10% PEG

| Nanocomplex Formulation | Average Size (nm) of Nanocomplex | Average Zeta Potential (mV) of Nanocomplex |
|---|---|---|
| 0% PEG | 143.8 | +50.5 |
| 5% PEG | 116.2 | +9.4 |
| 10% PEG | 110.4 | +26.1 |

TABLE 14

The diffusion rates of translocated nanocomplexes with 0, 5 and 10% PEG in mucus (Dm) and water (Dw).

| | Normal Mucus | | | CF Mucus | | |
|---|---|---|---|---|---|---|
| | Diffusion ($cm^2s^{-1}$) | Dm/Dw | Fold-impedance | Diffusion (cm2s-1) | Dm/Dw | Fold-impedance |
| Cationic 0% PEG | 7.25 × 10-9 | 1.53 × 10-1 | 6.54 | 9.80 × 10-10 | 2.15 × 10-2 | 46.5 |
| Cationic 5% PEG | 6.00 × 10-9 | 1.25 × 10-1 | 8.00 | 1.40 × 10-9 | 2.48 × 10-2 | 40.3 |
| Cationic 10% PEG | 4.50 × 10-9 | 9.33 × 10-2 | 10.7 | 1.38 × 10-9 | 2.32 × 10-2 | 43.1 |

The diffusion rates of translocated cationic nanocomplexes with 0, 5 and 10% PEG (excluding those described in Section 3.2.) were calculated using Fick's and Stokes' laws, respectively.

Table 14 shows that the diffusion of cationic nanocomplexes was generally more impeded in CF mucus compared to normal mucus. Cationic nanocomplexes with 0, 5 and 10% PEG diffused 6.54-, 8- and 10.7-fold more slowly in normal mucus compared to water, respectively. This suggests that PEGylation marginally hinders the translocation of cationic nanocomplexes through normal mucus. Cationic nanocomplexes with 0, 5 and 10% PEG diffused 46.5-, 40.3- and 43.1-fold more slowly in CF mucus compared to water, respectively. This suggests that PEGylation, unlike OligoM treatment, only very marginally improves the translocation of cationic nanocomplexes through CF mucus.

The invention claimed is:

1. A method for translocating a cationic micro/nanoparticle across a mucus layer said method comprising contacting the mucus layer with at least one alginate oligomer and a cationic micro/nanoparticle, wherein said at least one alginate oligomer has at least 70% mannuronate residues, and wherein said at least one alginate oligomer and said cationic micro/nanoparticle are separate from one another.

2. The method of claim 1 comprising delivering a molecule of interest to an epithelial cell of a mucosal surface, wherein said mucus layer is the mucus layer of the mucosal surface.

3. The method of claim 2, wherein said micro/nanoparticle carries the molecule of interest or said molecule is provided in a micro/nanoparticulate form thereof.

4. The method of claim 3, wherein the molecule of interest is covalently bound to another component of the micro/nanoparticle or may be distinct from other components of the micro/nanoparticle.

5. The method of claim 2, wherein said molecule of interest is a molecule of therapeutic and/or diagnostic utility.

6. The method of claim 1, wherein the mucus layer is the mucus layer of a mucosal surface (i) affected by CFTR dysfunction, (ii) of the respiratory system, (iii) of the gastrointestinal tract, (iv) of the pancreatic and/or bile ducts, (v) of the female reproductive system, or (vi) of the male reproductive system.

7. The method of claim 1, wherein said micro/nanoparticle is (i) a microparticle of about 1 μm to about 500 μm or (ii) a nanoparticle of about 1 nm to about 1000 nm.

8. The method of claim 1, wherein the micro/nanoparticle is a vesicle, micelle, virus, virus like particle, dendrimer, metal/metallic micro/nanoparticle, carbon nanotube, silica micro/nanoparticle, or polymeric micro/nanoparticle.

9. The method of claim 8, wherein the micro/nanoparticle is a liposome or lipoplex comprising a cationic lipid selected from the group consisting of N,N-dioleyl-N,N-dimethylammonium chloride (DODAC), N,N-distearyl-N,N-dimethylammonium bromide (DDAB), 2,3-dioleoyloxy trimethylammonium propane (DOTAP), 2,3-di-(oleyloxy) propyl trimethyl ammonium (DOTMA), N-[1-(2,3,-ditetradecyloxy) propyl]-N,N-dimethyl-N-hydroxyethylammonium bromide (DMRIE), N-[1-(2,3,dioleyloxy) propyl]-N,N-dimethyl-N-hydroxy ethylammonium bromide (DORIE), 3B-[N—(N',N'-dimethylaminoethane) carbamoyl]cholesterol (DC-Choi), dimethyldioctadecylammonium (DDAB), dioctadecylamidoglycyl spermine (DOGS) and 2,3-dioleyloxy-1-(dimethylamino) propane (DODMA).

10. The method of claim 8, wherein the micro/nanoparticle is a virus carrying a nucleic acid vector or a heterologous peptide or an oncolytic virus.

11. The method of claim 8, wherein the polymeric micro/nanoparticle comprises polystyrene, polylactic acid, polyacrylamide, melamine, poly(D-L-lactide), poly-D-L-glycolide, polyalkylcyanoacrylate, poly(lactide-co-glycolide) PLA, polycaprolactone, chitosan, gelatine, albumin, dextran, agarose, poly-L-glutamic acid and/or poly L-lysine.

12. The method of claim 8, wherein the metal/metallic micro/nanoparticle comprises gold, silver, platinum, iron, copper, gadolinium, indium, technetium, gallium, rhenium, lutetium, actinium, yttrium, antimony), tin, dysprosium, cobalt, ruthenium, palladium, cadmium, tellurium, barium, terbium, lanthanum, radium, strontium, samarium, ytterbium, thallium, caesium, iridium and rubidium.

13. The method of claim 2, wherein the molecule of interest is a therapeutically active agent, a diagnostic agent, an imaging agent, or an agent for engineering the properties of a cell or the products a cell produces.

14. The method of claim 13, wherein the therapeutically active agent is a small molecule pharmaceutical, a biological therapeutic or a radiopharmaceutical.

15. The method of claim 14 wherein the biological therapeutic is an antibody, a peptide hormone, a cytokine, a peptide growth factor, a peptide antigen or a nucleic acid.

16. The method of claim 13, wherein the therapeutically active agent is a CFTR modulator, an antibiotic, an antifungal, an antiviral, a cytotoxic chemotherapy agent, an angiogenesis inhibitor, an anti-cancer monoclonal antibody, a radioimmunotherapeutic, an immunostimulatory agent, an immunosuppressant, a corticosteroid, a non-steroidal anti-inflammatory drug (NSAID), a bronchodilator, or an oral antidiabetic drug.

17. The method of claim 13, wherein the therapeutically active agent is a nucleic acid for use in gene therapy, gene editing, RNA interference therapy, antisense therapy or an in vitro transcribed mRNA therapy.

18. The method of claim 13, wherein the diagnostic agent is a radiodiagnostic, a contrast agent or a nucleic acid or protein for use as a molecular probe.

19. The method of claim 13, wherein the cell engineering agent is a nuclease, a protease, a lipase, a co-factor, a precursor compound or a substrate.

20. The method of claim 1, wherein said alginate oligomer has an average molecular weight of less than 35,000 Daltons.

21. The method of claim 1, wherein the alginate oligomer has a degree of poplymerization (DP), or a number average degree of poplymerization (DPn) of 2 to 100.

22. The method of claim 1, wherein the alginate oligomer has at least 80% M residues.

23. The method of claim 1, wherein the alginate oligomer has a degree of polymerization (DP), or a number average degree of polymerization (DPn) of 2 to 28.

* * * * *